US011077228B2

(12) United States Patent
Kourtis et al.

(10) Patent No.: US 11,077,228 B2
(45) Date of Patent: Aug. 3, 2021

(54) INTERPENETRATING POLYMER NETWORKS

(71) Applicant: Hyalex Orthopaedics, Inc., Lexington, MA (US)

(72) Inventors: Lampros Kourtis, Cambridge, MA (US); Iraklis Kourtis, Arlington, MA (US); Jun Li, Winchester, MA (US); Gary Li, Cambridge, MA (US)

(73) Assignee: Hyalex Orthopaedics, Inc., Lexington, MA (US)

( * ) Notice: Subject to any disclaimer, the term of this patent is extended or adjusted under 35 U.S.C. 154(b) by 0 days.

(21) Appl. No.: 16/251,966

(22) Filed: Jan. 18, 2019

(65) Prior Publication Data
US 2019/0224367 A1    Jul. 25, 2019

Related U.S. Application Data

(63) Continuation-in-part of application No. 15/752,168, filed as application No. PCT/US2016/046350 on Aug. 10, 2016, now abandoned.
(Continued)

(51) Int. Cl.
*A61L 27/34* (2006.01)
*C08L 75/04* (2006.01)
(Continued)

(52) U.S. Cl.
CPC ............ *A61L 27/34* (2013.01); *A61F 2/28* (2013.01); *A61L 27/26* (2013.01); *A61L 27/52* (2013.01);
(Continued)

(58) Field of Classification Search
CPC ........ B29K 2105/0091; C08G 2700/00; C08G 18/83; C08G 18/48; C08G 2270/00;
(Continued)

(56) References Cited

U.S. PATENT DOCUMENTS 3,030,327 A    4/1962   Hosch
3,053,251 A    9/1962   Black et al.
(Continued)

FOREIGN PATENT DOCUMENTS

EP    0650707 A1    5/1995
EP    1779875 A1    5/2007
(Continued)

OTHER PUBLICATIONS

Balamurugan et al.; Development and spectral characterization of poly(methyl methacrylate) /hydroxyapatite composite for biomedical applications; Trenads Biomater. Artif. Organs; 18(1); pp. 41-45; Jul. 2004.
(Continued)

*Primary Examiner* — Brian A Dukert
*Assistant Examiner* — Rebecca Lynee Zimmerman
(74) *Attorney, Agent, or Firm* — Clark & Elbing LLP

(57) ABSTRACT

IPN compositions and methods of making the same are provided. The IPN compositions can include a water swellable, water permeable IPN or semi-IPN member with a first polymer network including a hydrophobic thermoset or thermoplastic polymer, a second polymer network including a non-ionic polymer, and a third polymer network including an ionic polymer containing sulfonic acid functional groups that are otherwise difficult to form composites with hydrophobic polymers. The IPN compositions can be used in orthopedic implants or in mechanical applications as a bearing material.

17 Claims, 38 Drawing Sheets

Related U.S. Application Data

(60) Provisional application No. 62/619,036, filed on Jan. 18, 2018, provisional application No. 62/202,921, filed on Aug. 10, 2015.

(51) Int. Cl.

| | | |
|---|---|---|
| *C08L 33/26* | (2006.01) | |
| *A61L 27/26* | (2006.01) | |
| *A61F 2/28* | (2006.01) | |
| *A61L 27/52* | (2006.01) | |
| *C08L 101/14* | (2006.01) | |
| *C08G 18/83* | (2006.01) | |
| *C08F 283/00* | (2006.01) | |
| *C08J 3/24* | (2006.01) | |
| *C08L 33/06* | (2006.01) | |
| *C08G 18/48* | (2006.01) | |
| *A61F 2/42* | (2006.01) | |
| *A61F 2/40* | (2006.01) | |
| *A61F 2/38* | (2006.01) | |
| *A61F 2/32* | (2006.01) | |

(52) U.S. Cl.
CPC .......... *C08F 283/006* (2013.01); *C08G 18/48* (2013.01); *C08G 18/83* (2013.01); *C08J 3/246* (2013.01); *C08L 33/066* (2013.01); *C08L 33/26* (2013.01); *C08L 75/04* (2013.01); *C08L 101/14* (2013.01); *A61F 2/32* (2013.01); *A61F 2/38* (2013.01); *A61F 2/40* (2013.01); *A61F 2/42* (2013.01); *A61L 2400/10* (2013.01); *C08G 2270/00* (2013.01)

(58) Field of Classification Search
CPC .......... C08J 2300/208; C08J 2400/208; C08J 3/246; C08L 2205/04; C08L 33/066; C08L 75/04; C08L 33/26; C08L 101/14; A61L 27/34; A61L 27/26; A61L 27/48; A61L 27/18; A61L 2400/10; A61L 27/52; A61F 2/30756; A61F 2/4225; A61F 2/3872; A61F 2/4081; A61F 2/32; A61F 2/0095; A61F 2/389; A61F 2/3099; A61F 2/4241; A61F 2/4405; A61F 2/4202; A61F 2/442; A61F 2/3877; A61F 2/3804; A61F 2/4261; C08F 285/00; C08F 283/006
See application file for complete search history.

(56) References Cited

U.S. PATENT DOCUMENTS

| | | |
|---|---|---|
| 3,702,611 A | 11/1972 | Fishbein |
| 3,826,678 A | 7/1974 | Hoffman et al. |
| 3,833,404 A | 9/1974 | Sperling et al. |
| 3,939,049 A | 2/1976 | Ratner et al. |
| 4,035,848 A | 7/1977 | Wagner |
| 4,128,600 A | 12/1978 | Skinner et al. |
| 4,192,827 A | 3/1980 | Mueller et al. |
| 4,224,699 A | 9/1980 | Weber |
| 4,302,553 A | 11/1981 | Frisch et al. |
| 4,312,079 A | 1/1982 | Dorre et al. |
| 4,320,709 A | 3/1982 | Hladun |
| 4,391,797 A | 7/1983 | Folkman et al. |
| 4,423,099 A | 12/1983 | Mueller et al. |
| 4,439,583 A | 3/1984 | Gould et al. |
| 4,452,925 A | 6/1984 | Kuzma et al. |
| 4,468,499 A | 8/1984 | Siegfried et al. |
| 4,477,604 A | 10/1984 | Oechsle, III |
| 4,487,865 A | 12/1984 | Balazs et al. |
| 4,500,676 A | 2/1985 | Balazs et al. |
| 4,502,161 A | 3/1985 | Wall |
| 4,536,554 A | 8/1985 | Lim et al. |
| 4,575,539 A | 3/1986 | DeCrosta et al. |
| 4,621,637 A | 11/1986 | Fishbein |
| 4,657,941 A | 4/1987 | Blackwell et al. |
| 4,678,468 A | 7/1987 | Hiroyoshi |
| 4,680,336 A | 7/1987 | Larsen et al. |
| 4,693,715 A | 9/1987 | Abel, Jr. |
| 4,693,721 A | 9/1987 | Ducheyne |
| 4,816,495 A | 3/1989 | Blackwell et al. |
| 4,836,884 A | 6/1989 | McAuslan |
| 4,846,841 A | 7/1989 | Oh |
| 4,865,601 A | 9/1989 | Caldwell et al. |
| 4,913,144 A | 4/1990 | Del Medico |
| 4,931,287 A | 6/1990 | Bae et al. |
| 4,966,934 A | 10/1990 | Huang et al. |
| 4,973,493 A | 11/1990 | Guire |
| 4,978,352 A | 12/1990 | Fedorov et al. |
| 5,030,230 A | 7/1991 | White |
| 5,061,270 A | 10/1991 | Aboczky |
| 5,067,961 A | 11/1991 | Kelman et al. |
| 5,087,392 A | 2/1992 | Burke et al. |
| 5,091,205 A | 2/1992 | Fan |
| 5,094,876 A | 3/1992 | Goldberg et al. |
| 5,100,689 A | 3/1992 | Goldberg et al. |
| 5,112,350 A | 5/1992 | Civerchia et al. |
| 5,115,056 A | 5/1992 | Mueller et al. |
| 5,122,133 A | 6/1992 | Evans |
| 5,133,769 A | 7/1992 | Wagner et al. |
| 5,171,318 A | 12/1992 | Gibson et al. |
| 5,258,024 A | 11/1993 | Chavel et al. |
| 5,264,495 A | 11/1993 | Irie et al. |
| 5,276,070 A | 1/1994 | Arroyo |
| 5,282,851 A | 2/1994 | Jacob-LaBarre |
| 5,290,548 A | 3/1994 | Goldberg et al. |
| 5,300,116 A | 4/1994 | Chirila et al. |
| 5,314,478 A | 5/1994 | Oka et al. |
| 5,374,515 A | 12/1994 | Parenteau et al. |
| 5,403,893 A | 4/1995 | Tanaka et al. |
| 5,476,515 A | 12/1995 | Kelman et al. |
| 5,554,665 A | 9/1996 | Tateosian et al. |
| 5,556,429 A | 9/1996 | Felt |
| 5,562,738 A | 10/1996 | Boyd et al. |
| 5,576,072 A | 11/1996 | Hostettler et al. |
| 5,587,406 A | 12/1996 | Yamamoto et al. |
| 5,589,563 A | 12/1996 | Ward et al. |
| 5,591,170 A | 1/1997 | Spievack et al. |
| 5,643,390 A | 7/1997 | Don et al. |
| 5,644,049 A | 7/1997 | Giusti et al. |
| 5,645,592 A | 7/1997 | Nicolais et al. |
| 5,656,210 A | 8/1997 | Hill et al. |
| 5,660,692 A | 8/1997 | Nesburn et al. |
| 5,674,942 A | 10/1997 | Hill et al. |
| 5,693,034 A | 12/1997 | Buscemi et al. |
| 5,716,633 A | 2/1998 | Civerchia |
| 5,733,289 A | 3/1998 | Seedhom et al. |
| 5,763,529 A | 6/1998 | Lucas |
| 5,770,669 A | 6/1998 | Robertson et al. |
| 5,800,412 A | 9/1998 | Zhang et al. |
| 5,824,079 A | 10/1998 | Siegler et al. |
| 5,834,532 A | 11/1998 | Yamamoto et al. |
| 5,836,313 A | 11/1998 | Perez et al. |
| 5,837,752 A | 11/1998 | Shastri et al. |
| 5,856,366 A | 1/1999 | Shiveley et al. |
| 5,904,927 A | 5/1999 | Amiji |
| 5,913,858 A | 6/1999 | Calandruccio et al. |
| 5,962,005 A | 10/1999 | Saga et al. |
| 5,976,648 A | 11/1999 | Li et al. |
| 6,001,894 A | 12/1999 | Ottersbach et al. |
| 6,005,160 A | 12/1999 | Hsiue et al. |
| 6,019,766 A | 2/2000 | Ling et al. |
| 6,027,742 A | 2/2000 | Lee et al. |
| 6,030,606 A | 2/2000 | Holmes |
| 6,031,017 A | 2/2000 | Waki et al. |
| 6,057,406 A | 5/2000 | Pojman et al. |
| 6,120,904 A | 9/2000 | Hostettler et al. |
| 6,160,084 A | 12/2000 | Langer et al. |
| 6,171,300 B1 | 1/2001 | Adams |
| 6,210,438 B1 | 4/2001 | Sheets, Jr. et al. |
| 6,214,044 B1 | 4/2001 | Silverstrini |
| 6,221,467 B1 | 4/2001 | Nazarova et al. |

(56) References Cited

U.S. PATENT DOCUMENTS

| | | | |
|---|---|---|---|
| 6,224,893 B1 | 5/2001 | Langer et al. |
| 6,231,605 B1 | 5/2001 | Ku |
| 6,231,611 B1 | 5/2001 | Mosseri |
| 6,239,209 B1 | 5/2001 | Yang et al. |
| 6,251,965 B1 | 6/2001 | Wang et al. |
| 6,254,637 B1 | 7/2001 | Lee et al. |
| 6,264,695 B1 | 7/2001 | Stoy |
| 6,265,016 B1 | 7/2001 | Hostettler et al. |
| 6,281,271 B1 | 8/2001 | Rumphorst et al. |
| 6,306,177 B1 | 10/2001 | Felt et al. |
| 6,306,424 B1 | 10/2001 | Vyakarnam et al. |
| 6,331,578 B1 | 12/2001 | Turner et al. |
| 6,368,315 B1 | 4/2002 | Gillis et al. |
| 6,372,815 B1 | 4/2002 | Sulc et al. |
| 6,376,742 B1 | 4/2002 | Zdrahala et al. |
| 6,388,043 B1 | 5/2002 | Langer et al. |
| 6,391,055 B1 | 5/2002 | Lkada et al. |
| 6,428,576 B1 | 8/2002 | Haldimann |
| 6,429,256 B1 | 8/2002 | Vandevoorde et al. |
| 6,437,018 B1 | 8/2002 | Gertzman et al. |
| 6,440,444 B2 | 8/2002 | Boyce et al. |
| 6,479,565 B1 | 11/2002 | Stanley |
| 6,482,209 B1 | 11/2002 | Engh et al. |
| 6,494,917 B1 | 12/2002 | McKellop et al. |
| 6,509,098 B1 | 1/2003 | Merrill et al. |
| 6,585,771 B1 | 7/2003 | Buttermilch et al. |
| 6,610,067 B2 | 8/2003 | Tallarida et al. |
| 6,629,997 B2 | 10/2003 | Mansmann |
| 6,632,235 B2 | 10/2003 | Weikel et al. |
| 6,632,246 B1 | 10/2003 | Simon et al. |
| 6,645,715 B1 | 11/2003 | Griffith et al. |
| 6,652,587 B2 | 11/2003 | Felt et al. |
| 6,673,079 B1 | 1/2004 | Kane |
| 6,673,112 B2 | 1/2004 | Nigam |
| 6,679,917 B2 | 1/2004 | Ek |
| 6,689,165 B2 | 2/2004 | Jacob et al. |
| 6,726,322 B2 | 4/2004 | Andino et al. |
| 6,733,533 B1 | 5/2004 | Lozier |
| 6,740,087 B2 | 5/2004 | Knox |
| 6,755,865 B2 | 6/2004 | Tarabishy |
| 6,759,449 B2 | 7/2004 | Kimura et al. |
| 6,846,875 B2 | 1/2005 | Pennings et al. |
| 6,852,125 B2 | 2/2005 | Simon et al. |
| 6,866,936 B2 | 3/2005 | Opolski |
| 6,911,212 B2 | 6/2005 | Gertzman et al. |
| 6,918,914 B2 | 7/2005 | Bauer |
| 6,921,264 B2 | 7/2005 | Mayer et al. |
| 6,949,251 B2 | 9/2005 | Dalai et al. |
| RE38,839 E | 10/2005 | Magnante |
| 6,953,594 B2 | 10/2005 | Lee et al. |
| 6,955,540 B2 | 10/2005 | Mayer et al. |
| 6,960,617 B2 | 11/2005 | Omidian et al. |
| 6,976,997 B2 | 12/2005 | Noolandi et al. |
| 7,008,226 B2 | 3/2006 | Mayer et al. |
| 7,008,635 B1 | 3/2006 | Coury et al. |
| 7,018,460 B2 | 3/2006 | Xu et al. |
| 7,019,192 B2 | 3/2006 | Gertzman et al. |
| 7,029,479 B2 | 4/2006 | Tallarida et al. |
| 7,037,984 B2 | 5/2006 | Lendlein et al. |
| 7,049,351 B2 | 5/2006 | Phelan et al. |
| 7,066,958 B2 | 6/2006 | Ferree |
| 7,067,194 B2 | 6/2006 | Mao et al. |
| 7,083,650 B2 | 8/2006 | Moskowitz et al. |
| 7,094,286 B2 | 8/2006 | Liu |
| 7,105,026 B2 | 9/2006 | Johnson et al. |
| 7,160,305 B2 | 1/2007 | Schmieding |
| 7,163,541 B2 | 1/2007 | Ek |
| 7,176,247 B1 | 2/2007 | Walker, Jr. |
| 7,204,897 B2 | 4/2007 | Stoy et al. |
| 7,217,294 B2 | 5/2007 | Kusanagi et al. |
| 7,220,491 B2 | 5/2007 | Rouns et al. |
| 7,235,592 B2 | 6/2007 | Muratoglu et al. |
| 7,279,174 B2 | 10/2007 | Pacetti et al. |
| 7,279,507 B2 | 10/2007 | Hu et al. |
| 7,303,814 B2 | 12/2007 | Lamberti et al. |
| 7,335,205 B2 | 2/2008 | Aeschlimann et al. |
| 7,341,593 B2 | 3/2008 | Auxepaules et al. |
| 7,371,257 B2 | 5/2008 | Sahatjian et al. |
| 7,387,810 B2 | 6/2008 | Hossainy |
| 7,468,075 B2 | 12/2008 | Lang et al. |
| 7,476,398 B1 | 1/2009 | Doillon et al. |
| 7,563,483 B2 | 7/2009 | Hossainy et al. |
| 7,618,462 B2 | 11/2009 | Ek |
| 7,678,151 B2 | 3/2010 | Ek |
| 7,713,305 B2 | 5/2010 | Ek |
| 7,824,666 B2 | 11/2010 | Wolff et al. |
| 8,252,851 B2 | 8/2012 | Young et al. |
| 8,497,023 B2 | 7/2013 | Myung et al. |
| 8,679,190 B2 | 3/2014 | Myung et al. |
| 8,853,294 B2 | 10/2014 | Myung et al. |
| 8,883,915 B2 | 11/2014 | Myung et al. |
| 9,114,024 B2 | 8/2015 | Kourtis et al. |
| 9,387,082 B2 | 7/2016 | Myung et al. |
| 9,750,842 B2 | 9/2017 | Kourtis et al. |
| 10,457,803 B2 | 10/2019 | Myung et al. |
| 2001/0029399 A1 | 10/2001 | Ku |
| 2001/0044026 A1 | 11/2001 | Vaghefi et al. |
| 2002/0022884 A1 | 2/2002 | Mansmann |
| 2002/0055007 A1 | 5/2002 | Soane et al. |
| 2002/0082699 A1 | 6/2002 | Ward et al. |
| 2002/0091229 A1 | 7/2002 | Hubbell et al. |
| 2002/0173855 A1 | 11/2002 | Mansmann |
| 2002/0198280 A1 | 12/2002 | Baba et al. |
| 2003/0008396 A1 | 1/2003 | Ku |
| 2003/0022216 A1 | 1/2003 | Mao et al. |
| 2003/0028196 A1 | 2/2003 | Bonutti |
| 2003/0083389 A1 | 5/2003 | Kao et al. |
| 2003/0083433 A1 | 5/2003 | James et al. |
| 2003/0092777 A1 | 5/2003 | Leitner |
| 2003/0100666 A1 | 5/2003 | DeGroot et al. |
| 2003/0114936 A1 | 6/2003 | Sherwood et al. |
| 2003/0130741 A1 | 7/2003 | McMinn |
| 2003/0153981 A1 | 8/2003 | Wang et al. |
| 2003/0170308 A1 | 9/2003 | Cleary et al. |
| 2004/0028804 A1 | 2/2004 | Anderson et al. |
| 2004/0034437 A1 | 2/2004 | Schmieding |
| 2004/0044410 A1 | 3/2004 | Ferree et al. |
| 2004/0059425 A1 | 3/2004 | Schmieding |
| 2004/0116564 A1 | 6/2004 | Devlin et al. |
| 2004/0133275 A1 | 7/2004 | Mansmann |
| 2004/0134502 A1 | 7/2004 | Mizuno et al. |
| 2004/0138382 A1 | 7/2004 | Dous |
| 2004/0139382 A1 | 7/2004 | Kim |
| 2004/0147466 A1 | 7/2004 | Barman et al. |
| 2004/0147927 A1 | 7/2004 | Tsougarakis et al. |
| 2004/0153040 A1 | 8/2004 | Martineau et al. |
| 2004/0153079 A1 | 8/2004 | Tsougarakis et al. |
| 2004/0153163 A1 | 8/2004 | Posner |
| 2004/0167528 A1 | 8/2004 | Schantz |
| 2004/0171740 A1 | 9/2004 | Ruberti et al. |
| 2004/0199250 A1 | 10/2004 | Fell |
| 2004/0204760 A1 | 10/2004 | Fitz et al. |
| 2004/0214914 A1 | 10/2004 | Marmo |
| 2004/0230315 A1 | 11/2004 | Ek |
| 2004/0236424 A1 | 11/2004 | Berez et al. |
| 2004/0266941 A1 | 12/2004 | Houston et al. |
| 2004/0267363 A1 | 12/2004 | Fell et al. |
| 2005/0004306 A1 | 1/2005 | Lubnin et al. |
| 2005/0013793 A1 | 1/2005 | Beckman et al. |
| 2005/0027364 A1 | 2/2005 | Kim et al. |
| 2005/0033295 A1 | 2/2005 | Wisnewski |
| 2005/0038520 A1 | 2/2005 | Binette et al. |
| 2005/0049459 A1 | 3/2005 | Hern |
| 2005/0055044 A1 | 3/2005 | Kangas |
| 2005/0065616 A1 | 3/2005 | Ankorina-Stark et al. |
| 2005/0090612 A1 | 4/2005 | Soane et al. |
| 2005/0113836 A1 | 5/2005 | Lozier et al. |
| 2005/0113928 A1 | 5/2005 | Cragg et al. |
| 2005/0126680 A1 | 6/2005 | Aeschlimann et al. |
| 2005/0142162 A1 | 6/2005 | Hunter et al. |
| 2005/0147685 A1 | 7/2005 | Osada et al. |
| 2005/0171604 A1 | 8/2005 | Michalow |
| 2005/0186248 A1 | 8/2005 | Hossainy et al. |
| 2005/0187146 A1 | 8/2005 | Helmus et al. |

(56) References Cited

U.S. PATENT DOCUMENTS

| | | |
|---|---|---|
| 2005/0215660 A1 | 9/2005 | Tomikawa et al. |
| 2005/0218541 A1 | 10/2005 | Peng et al. |
| 2005/0228161 A1 | 10/2005 | Benz et al. |
| 2005/0251267 A1 | 11/2005 | Winterbottom et al. |
| 2005/0251268 A1 | 11/2005 | Truncale |
| 2005/0267482 A1 | 12/2005 | Hyde |
| 2005/0267584 A1 | 12/2005 | Burdulis et al. |
| 2005/0278025 A1 | 12/2005 | Ku et al. |
| 2005/0283255 A1 | 12/2005 | Geremakis et al. |
| 2005/0287187 A1 | 12/2005 | Mansmann |
| 2006/0008506 A1 | 1/2006 | Cipriano De Sousa et al. |
| 2006/0052878 A1 | 3/2006 | Schmieding |
| 2006/0083773 A1 | 4/2006 | Myung et al. |
| 2006/0093648 A1 | 5/2006 | Coury et al. |
| 2006/0105295 A1 | 5/2006 | Mayer et al. |
| 2006/0111726 A1 | 5/2006 | Felt et al. |
| 2006/0122543 A1 | 6/2006 | Mayer et al. |
| 2006/0134186 A1 | 6/2006 | Carlton et al. |
| 2006/0142406 A1 | 6/2006 | Schmitt et al. |
| 2006/0148985 A1 | 7/2006 | Karthauser |
| 2006/0188487 A1 | 8/2006 | Thomas et al. |
| 2006/0188940 A1 | 8/2006 | Cima et al. |
| 2006/0193899 A1 | 8/2006 | Sawhney |
| 2006/0224244 A1 | 10/2006 | Thomas et al. |
| 2006/0233855 A1 | 10/2006 | Seliktar et al. |
| 2006/0235517 A1 | 10/2006 | Hodorek |
| 2006/0235539 A1 | 10/2006 | Blunn et al. |
| 2006/0235542 A1 | 10/2006 | Hodorek et al. |
| 2006/0240478 A1 | 10/2006 | Nishimi et al. |
| 2006/0241629 A1 | 10/2006 | Krebs et al. |
| 2006/0241759 A1 | 10/2006 | Trieu |
| 2006/0246241 A1 | 11/2006 | Kruger et al. |
| 2006/0282169 A1 | 12/2006 | Felt et al. |
| 2006/0287721 A1 | 12/2006 | Myung et al. |
| 2006/0287730 A1 | 12/2006 | Segal et al. |
| 2007/0014828 A1 | 1/2007 | Fitzhugh et al. |
| 2007/0016211 A1 | 1/2007 | Botimer |
| 2007/0048382 A1 | 3/2007 | Meyer et al. |
| 2007/0067032 A1 | 3/2007 | Felt et al. |
| 2007/0068816 A1 | 3/2007 | Solomon et al. |
| 2007/0078388 A1 | 4/2007 | Kangas |
| 2007/0078518 A1 | 4/2007 | Lavi |
| 2007/0083266 A1 | 4/2007 | Lang |
| 2007/0087031 A1 | 4/2007 | Ashman et al. |
| 2007/0088444 A1 | 4/2007 | Hodorek et al. |
| 2007/0098675 A1 | 5/2007 | Elisseeff et al. |
| 2007/0099840 A1 | 5/2007 | Ulijn et al. |
| 2007/0100457 A1 | 5/2007 | Hyde |
| 2007/0118218 A1 | 5/2007 | Hooper |
| 2007/0126982 A1 | 6/2007 | Myung et al. |
| 2007/0134291 A1 | 6/2007 | Ting et al. |
| 2007/0135922 A1 | 6/2007 | Trieu |
| 2007/0141108 A1 | 6/2007 | Thomas et al. |
| 2007/0142914 A1 | 6/2007 | Jones et al. |
| 2007/0149441 A1 | 6/2007 | Aeschlimann et al. |
| 2007/0167541 A1 | 7/2007 | Ruberti et al. |
| 2007/0179605 A1 | 8/2007 | Myung et al. |
| 2007/0179607 A1 | 8/2007 | Hodorek et al. |
| 2007/0179622 A1 | 8/2007 | Denoziere et al. |
| 2007/0191963 A1 | 8/2007 | Winterbottom et al. |
| 2007/0198022 A1 | 8/2007 | Lang et al. |
| 2007/0202148 A1 | 8/2007 | Ringeisen et al. |
| 2007/0219640 A1 | 9/2007 | Steinberg |
| 2007/0224238 A1 | 9/2007 | Mansmann et al. |
| 2007/0225823 A1 | 9/2007 | Hawkins et al. |
| 2007/0233240 A1 | 10/2007 | Frank et al. |
| 2007/0233269 A1 | 10/2007 | Steines et al. |
| 2007/0265704 A1 | 11/2007 | Mayer et al. |
| 2007/0270783 A1 | 11/2007 | Zumsteg et al. |
| 2007/0276394 A1 | 11/2007 | Johnson et al. |
| 2008/0058954 A1 | 3/2008 | Trieu |
| 2008/0070086 A1 | 3/2008 | Fukuchi et al. |
| 2008/0077249 A1 | 3/2008 | Gradel |
| 2008/0103505 A1 | 5/2008 | Fransen |
| 2008/0124376 A1 | 5/2008 | Pruitt et al. |
| 2008/0139694 A1 | 6/2008 | Ratcliffe |
| 2008/0182919 A1 | 7/2008 | Saimi et al. |
| 2008/0241214 A1 | 10/2008 | Myung et al. |
| 2008/0269370 A1 | 10/2008 | Myung et al. |
| 2008/0317818 A1 | 12/2008 | Griffith et al. |
| 2009/0035344 A1 | 2/2009 | Thomas et al. |
| 2009/0062408 A1 | 3/2009 | Liu et al. |
| 2009/0062423 A1 | 3/2009 | Betz et al. |
| 2009/0088846 A1 | 4/2009 | Myung et al. |
| 2009/0142508 A1 | 6/2009 | Lai et al. |
| 2009/0163860 A1 | 6/2009 | Patrick et al. |
| 2009/0176891 A1 | 7/2009 | Chogle et al. |
| 2009/0209966 A1 | 8/2009 | Chandler |
| 2009/0221730 A1 | 9/2009 | Kowalski et al. |
| 2009/0233887 A1 | 9/2009 | Shalaby et al. |
| 2009/0234044 A1 | 9/2009 | Rheinberger et al. |
| 2009/0240337 A1 | 9/2009 | Myung et al. |
| 2009/0281545 A1 | 11/2009 | Stubbs |
| 2009/0312807 A1 | 12/2009 | Boudreault et al. |
| 2010/0010114 A1 | 1/2010 | Myung et al. |
| 2010/0032090 A1 | 2/2010 | Myung et al. |
| 2010/0056646 A1 | 3/2010 | Shalaby et al. |
| 2010/0125341 A1 | 5/2010 | Frauens |
| 2011/0152868 A1 | 6/2011 | Kourtis et al. |
| 2011/0184423 A1 | 7/2011 | Rushton et al. |
| 2011/0237705 A1 | 9/2011 | Leonard et al. |
| 2012/0045651 A1* | 2/2012 | Myung .................. A61K 6/09 428/423.1 |
| 2012/0116531 A1 | 5/2012 | Forsell |
| 2012/0209396 A1 | 8/2012 | Myung et al. |
| 2012/0232657 A1 | 9/2012 | Myung et al. |
| 2012/0277807 A1 | 11/2012 | Myung et al. |
| 2012/0308508 A1 | 12/2012 | Saunders et al. |
| 2013/0096691 A1 | 4/2013 | Myung et al. |
| 2013/0103157 A1 | 4/2013 | Kourtis et al. |
| 2013/0131741 A1 | 5/2013 | Kourtis et al. |
| 2013/0138210 A1 | 5/2013 | Myung et al. |
| 2013/0138211 A1 | 5/2013 | Myung et al. |
| 2013/0217829 A1 | 8/2013 | Myung et al. |
| 2014/0172098 A1 | 6/2014 | Myung et al. |
| 2015/0025161 A1 | 1/2015 | Myung et al. |
| 2015/0272599 A1 | 10/2015 | Kourtis et al. |
| 2015/0284654 A1 | 10/2015 | Myung et al. |
| 2016/0346089 A1 | 12/2016 | Myung et al. |
| 2017/0107370 A1 | 4/2017 | Myung et al. |
| 2017/0327624 A1 | 11/2017 | Kourtis et al. |
| 2017/0348011 A1 | 12/2017 | Kourtis et al. |
| 2018/0236136 A1 | 8/2018 | Kourtis et al. |
| 2019/0218386 A1 | 7/2019 | Kourtis et al. |
| 2020/0023098 A1 | 1/2020 | Kourtis et al. |
| 2020/0046880 A1 | 2/2020 | Kourtis et al. |

FOREIGN PATENT DOCUMENTS

| | | |
|---|---|---|
| EP | 2268331 A2 | 1/2011 |
| EP | 2626090 A2 * | 8/2013 |
| GB | 2372707 A | 9/2002 |
| JP | H06-287443 A | 10/1994 |
| JP | H09-077809 A | 3/1997 |
| JP | H10-500038 A | 1/1998 |
| JP | 3176176 B2 | 6/2001 |
| JP | 2002514233 A | 5/2002 |
| JP | 2002518564 A | 6/2002 |
| JP | 2002518565 A | 6/2002 |
| JP | 2003171475 A | 6/2003 |
| JP | 2004512079 A | 4/2004 |
| JP | 2004515311 A | 5/2004 |
| JP | 2005305162 A | 11/2005 |
| JP | 2006517842 A | 8/2006 |
| JP | 2007501674 A | 2/2007 |
| WO | WO-94/01468 A1 | 1/1994 |
| WO | WO-95/30388 A1 | 11/1995 |
| WO | WO-98/06768 A1 | 2/1998 |
| WO | WO-99/45978 A1 | 9/1999 |
| WO | WO-99/67311 A1 | 12/1999 |
| WO | WO-99/67312 A1 | 12/1999 |
| WO | WO-00/02937 A1 | 1/2000 |
| WO | WO-00/043050 A1 | 7/2000 |
| WO | WO-02/026848 A2 | 4/2002 |

(56) References Cited

FOREIGN PATENT DOCUMENTS

| WO | WO-03/009337 A2 | 1/2003 |
|----|----|----|
| WO | WO-2004/032767 A1 | 4/2004 |
| WO | WO-2004/055057 A1 | 7/2004 |
| WO | WO-2004/073563 A2 | 9/2004 |
| WO | WO-2004/091685 A2 | 10/2004 |
| WO | WO-2007/067697 A2 | 6/2007 |
| WO | WO-2007/068625 A1 | 6/2007 |
| WO | WO-2007/112305 A2 | 10/2007 |
| WO | WO-2008/100617 A1 | 8/2008 |
| WO | WO-2009/071937 A1 | 6/2009 |
| WO | WO-2010/037685 A1 | 4/2010 |
| WO | WO-2010/059495 A2 | 5/2010 |
| WO | WO-2012/096997 A2 | 7/2012 |
| WO | WO-2015/023569 A1 | 2/2015 |
| WO | WO-2017/027590 A1 | 2/2017 |

OTHER PUBLICATIONS

Barszczewska-Rybarek, Izabela M.; Quantitative determination of degree of conversion in photocured poly (urethane-dimethacrylate)s by Fourier transform infrared spectroscopy; Journal of Applied Polymer Science; vol. 123; issue 3; pp. 1604-1611; Feb. 5, 2012.
Bobyn et al., The optimum pore size for the fixation of porous-surfaced metal implants by the ingrowth of bone. Clin Orthop Relat Res, Jul./Aug. 1980(150): p. 263-70.
Borden et al.; The sintered microsphere matrix for bone tissue engineering: In vitroosteoconductivity studies; J. Biomed. Mat. Res.; 61(3); pp. 421-429; Sep. 2002.
Brodbeck et al., Biomaterial adherent macrophage apoptosis is increased by hydrophilic and anionic substrates in vivo. Proc Natl Acad Sci U S A, Aug. 6, 2002. 99(16): p. 10287-92.
Brown et al.; Solvent/Non-solvent sintering: A novel route to create porous microsphere scaffolds for tissue regeneration; J. Biomed. Mat. Res. (Part B: Applied Biomaterials); 86B(2); pp. 396-406; Aug. 2008.
Causton et al.; Dental materials: 1981 literature review Part 1; Journal of Dentistry; vol. 12; Issue 1; pp. 1R28; Mar. 1984.
Charnley, J.; Anchorage of the femoral head prosthesis to the shaft of the femur; J Bone Joint Surg Br.; 42-B:28-30; Feb. 1960.
Chen et al.; Mechanical Properties of Polyepichlorohydrin Polyurethane/Poly(methyl methacrylate) IPNs; Chinese J Appl Chem; 12(4):66-69; Aug. 1995 (wEngAbs).
Christenson et al., "Antioxidant inhibition of poly(carbonate urethane) in vivo biodegradation," J Biomed Mater Res A. 76(3): 480-490 (2006).
Covert et al.; Friction characteristics of a potential articular cartilage biomaterial. Wear, Aug. 2003. 255: p. 1064-1068.
Depuy Orthopaedics; Bone Cement Time Setting Chart; product file; date of publication unknown; available to applicants at least as of Jul. 2012.
Dror et al.; Gradient interpenetrating polymer networks. I. Poly(ether urethane) and polyacrylamide IPN; J of Applied Polymer Science; 26; pp. 1741-1757; Jun. 1981.
Elbert; Liquid-liquid two phase systems for the production of porous hydrogels and hydrogel microsphers for biomedical applications: A tutorial review; Acta Biomater; 7(1); pp. 31-56; Jan. 31, 2011.
Elmer's Products Inc.; Material Safety Data Sheet; "Elmer's Nano Glue"; Jun. 13, 2007.
Elsabee et al.; Gradient interpenetrating polymer networks. II. Polyacrylamide gradients in poly(ether urethane); J of Applied Polymer Science; 28(7); pp. 2151-2166; Jun. 1983.
Esstech, Inc.; Urethane Dimethacrylate (product specification); 1 pg.; Note: this document was available to applicant(s) at least as of (Apr. 8, 2015).
Evans et al.; The use of corneal organ culture in biocompatibility studies; Biomaterials; vol. 23; pp. 1359-1367; Mar. 2002.
Forsell; U.S. Appl. No. 61/229,735 entitled "Hip Joint Method," filed Jul. 30, 2009.

Frank, Curt; Structure-property relationships for hydrogels with applications to biomedical devices; Presentation at American Chemical Society Mtg; San Francisco, CA; Sep. 11, 2006.
Gao et al.; Grafting of hydrophilic monomers onto polyurethane membranes by solution or pre-absorbing methods for acceleration of cell compatibility; Chinese Journal of Polymer Science; vol. 19; No. 5; pp. 493-498; Oct. 20, 2001.
Gong et al.; Double-network hydrogels with extremely high mechanical strength; Adv. Mater.; vol. 15; No. 14; pp. 1155-1158; Jul. 17, 2003.
Gorna et al., "Biodegradable porous polyurethane scaffolds for tissue repair and regeneration," J Biomed Mater Res A. 79(1):128-38 (2006).
Gorna et al.; Preparation, degradation, and calcification of biodegradable polyurethane foams for bone graft substitutes; J Biomed Mater Res A. 67(3): 813-827 (2003).
Goswami et al.; Engineering properties of novolac resin-PMMA {Poly(methyl methacrylate)} IPN system; Journal of Applied Science; 93(6); pp. 2764-2774; Jul. 16, 2004.
Guelcher et al.; Synthesis and in vitro biocompatibility of injectable polyurethane foam scaffolds; Tissue Engineering; 12(5); pp. 1247-1259; May 2006.
Guelcher et al.; Synthesis of biocompatible segmented polyurethanes from aliphatic diisocyanates and diurea diol chain extenders; Acta biomaterialia; 1(4); pp. 471-484; Jul. 2005.
Gunatillake et al.; Designing biostable polyurethane elastomers for biomedical implants; Aust. J. Chem.; vol. 56; pp. 545-557; Jun. 2003.
Hern et al.; Incorporation of adhesion peptides into nonadhesive hydrogels useful for tissue resurfacing; J. Biomed. Materials Research; vol. 39; No. 1; pp. 266-276; Feb. 1998.
Hsieh et al.; Compatibility and Morphology in Polyurethane and Polystyrene Ionomeric Interpenetrating Polymer Networks; Polymer Journal; 21(1); pp. 1-10; Jan. 15, 1989.
International Search Report for International Application No. PCT/US08/01642, dated May 16, 2008 (1 page).
International Search Report for International Application No. PCT/US16/46350, dated Oct. 14, 2016 (3 pages).
International Search Report for International Application No. PCT/US19/42193, dated Sep. 27, 2019 (3 pages).
International Search Report for International Application No. PCT/US2008/004976, dated Oct. 15, 2009 (4 pages).
Ithaca College Gross Anatomy; Joints of the Back; ; 4 pgs. (downloaded Dec. 1, 2013 from http://www.ithaca.edu/faculty/lahr/LE2000/Back/Jointpage.htm).
Iwasaki et al., Hydrogel like elastic membrane consisting of semi-interpenetrating polymer networks based on a phosphorylcholine polymer and a segmented polyurethane; J. Polym. Sci Part A: Polym Chem; 41; pp. 68-75; Jan. 2003.
Jones et al.; Sequential Polyurethane-Poly(Methylmethacrylate) Interpenetrating Polymer Networks as Ureteral Biomaterials: Mechanical Properties and Comparative Resistance to Urinaryencrustation; J Mater Sci Mater Med; 8(11):713-717; Nov. 1997.
Kagata et al., "Friction of Gels. 6. Effects of Sliding Velocity and Viscoelastic Responses of the Network," J Phys Chem B. 106(18):4596-601 (2002).
Kaneko et al., "Mechanically Strong Hydrogels with Ultra-Low Frictional Coefficients," Advanced Materials. 17(5):535-8 (2005).
Kanie et al.; Flexural properties of ethyl or methyl methacrylate-UDMA blend polymers; Dent Mater J; 29(5); pp. 575-581; Oct. 2010.
Khan et al., Analysis and evaluation of a biomedical polycarbonate urethane tested in an in vitro study and an ovine arthroplasty model. Part I: materials selection and evaluation. Biomaterials, Feb. 2005. 26(6): p. 621-31.
Kim et al.; Adhesion and growth of endothelial cell on amphiphilic PU/PS IPN surface: effect of amphiphilic balance and immobilized collagen; Journal of Biomedical Materials Research; 62(4); pp. 613-621; Sep. 6, 2002.
Kim et al.; Electrical/pH Responsive Properties of Poly(2-acrylamido-2-methylpropane sulfonic acid)/Hyaluronic Acid Hydrogels; Journal of Applied Polymer Science; vol. 92; issue 3; pp. 1731-1736; May 2004.

(56) References Cited

OTHER PUBLICATIONS

Kim et al.; Electrochemical behavior of an interpenetrating polymer network hydrogel composed of poly (propylene glycol) and poly(acrylic acid); Journal of Applied Polymer Science; vol. 89; pp. 2301-2305; Aug. 2003.

Kim et al.; Water sorption of ploy(propylene glycol)/poly(acrylic acid) interpenetrating polymer network hydrogels; Reactive & Functional Polymers; vol. 55; pp. 69-73; Feb. 2003.

Kourtis et al., U.S. Appl. No. 13/573,788, entitled "Polymeric adhesive for anchoring compliant materials to another surface," filed Oct. 3, 2012 (103 pages).

Kourtis et al., U.S. Appl. No. 13/683,731, entitled "Systems, Devices, and Methods for Anchoring Orthopaedic Implants to Bone," filed Nov. 21, 2012 (130 pages).

Kourtis et al.; U.S. Appl. No. 14/831,746 entitled "Systems, devices, and methods for anchoring orthopaedic implants to bone," filed Aug. 20, 2015.

Kourtis et al.; U.S. Appl. No. 15/442,413, entitled "Method, device, and system for shaving and shaping of a joint," filed Feb. 24, 2017 (69 pages).

Kourtis et al.; U.S. Appl. No. 15/668,547, entitled "Polymeric adhesive for achoring compliant materials to another surface," filed Aug. 3, 2017 (109 pages).

Kourtis et al.; U.S. Appl. No. 15/752,168, entitled "Interpenetrating polymer networks," filed Feb. 12, 2018 (109 pages).

Kourtis et al.; U.S. Appl. No. 12/973,829, entitled "Method, device, and system for shaving and shaping of a joint," filed Dec. 20, 2010 (69 pages).

Kwong et al.; A comparison of the shrinkage of commercial bone cements when mixed under vacuum; J Bone Joint Surg Br.; 88(1):120-2; Jan. 2006.

Lam et al.; Update on Ureteral Stents; Urology; 64:9-15; Jul. 2004.

Lamba et al.; Polyurethanes in Biomedical Application; CRC Press; pp. 11, 14, 16, 18-20, 57-59, 73, 79 & 104; Nov. 1997.

Lee et al.; Interpenetrating polymer network hydrogels based on poly (ethylene glycol) macromer and chitosan; Carbohydrate Polymer; vol. 41; No. 2; pp. 197-205; Feb. 2000.

Lewis G.; Properties of acrylic bone cement: state of the art review; J Biomed Mater Res.; 38(2):155-82; Summer Jun.-Aug. 1997.

Lipatov et al.; Gradient interpenetrating polymer networks; Journal of Materials Science; 30(4); pp. 1095-1104; Feb. 1995.

Lu et al.; Release behavior of high molecular weight solutes from poly(ethylene glycol)-based degradable networks; Macromolecules; vol. 33(7); pp. 2509-2515; Mar. 2000.

Maroudas et al.; Permeability of articular cartilage; Nature; vol. 219(5160); pp. 1260-1261; Sep. 21, 1968.

Matinlinna et al., "Isocyanato- and Methacryloxysilanes Promote Bis-GMA Adhesion to Titanium," J Dent Res. 84(4):360-364 (2005).

MIT.edu; Material Modulus Properties; 2pgs.; Feb. 8, 2007 (downloaded Nov. 27, 2013 from http://web.archive.org/web/*/http://web.mit.edu/course/3/3.11/www/modules- /props.pdf).

Morgan et al.; Dependence of yield strain of human trabecular bone on anatomic site; J Biomech.; 34(5):569-77; May 2001.

Mow et al., Basic Orthopaedic Biomechanics and Mechano-Biology, Lippincot Williams and Wilkins, 3rd Edition, Apr. 2005, pp. 459-461.

Myung et al.; Biomimetic strain hardening in interpenetrating polymer network hydrogels; Polymer, ; vol. 48; No. 18; pp. 5376-5387; Jun. 2007.

Myung et al.; U.S. Appl. No. 12/409,359, entitled "Methods, devices and compositions for adhering hydrated polymer implants to bone," filed Mar. 23, 2009 (45 pages).

Myung et al.; U.S. Appl. No. 12/499,041, entitled "Hydrophilic Interpenetrating Polymer Networks Derived From Hydrophobic Polymers," filed Jul. 7, 2009 (95 pages).

Myung et al.; U.S. Appl. No. 12/536,233, entitled "Polyurethane-grafted hydrogels," filed Aug. 5, 2009 (51 pages).

Myung et al.; U.S. Appl. No. 13/347,647, entitled "Orthopedic implants having gradient polymer alloys," filed Jan. 10, 2012 (144 pages).

Myung et al.; U.S. Appl. No. 13/418,294, entitled "Hydrogel Anthroplasty Device," filed Mar. 12, 2012 (99 pages).

Myung et al.; U.S. Appl. No. 13/542,464, entitled "Methods, Devices and Compositions for Adhering Hydrated Polymer Implants to Bone," filed Jul. 5, 2012 (48 pages).

Myung et al.; U.S. Appl. No. 13/748,573, entitled "Hydrophilic Interpenetrating Polymer Networks Derived From Hydrophobic Polymers," filed Jan. 23, 2013 (99 pages).

Myung et al.; U.S. Appl. No. 13/748,576, entitled "Hydrophilic Interpenetrating Polymer Networks Derived From Hydrophobic Polymers," filed Jan. 23, 2013 (103 pages).

Myung et al.; U.S. Appl. No. 13/816,537, entitled "Hydrophobic and Hydrophilic Interpenetrating Polymer Networks Derived From Hydrophobic Polymers and Methods of Preparing the Same," filed Apr. 24, 2013 (153 pages).

Myung et al.; U.S. Appl. No. 13/905,028, entitled "Polyurethane-grafted hydrogels," filed May 29, 2013 (58 pages).

Myung,David; Structure, properties, and medical device applications of mechanically enhanced, biometric hydrogel alloys; Doctoral Thesis; Stanford University; Dec. 2007.

Nanci et al., "Chemical modification of titanium surfaces for covalent attachment of biological molecules," J Biomed Mater Res. 40(2):324-35 (1998) (13 pages).

Neurosurgical.com; Spinal Anatomy: The Regions of the Spine; 5pgs. (downloaded Dec. 1, 2013 http://www.neurosurgical.com/neuro_medical_info/spinal_anatomy.htm).

Ohman et al.; Mechanical testing of cancellous bone from the femoral head: experimental errors due to off-axis measurements; J Biomech.; 40(11):2426-33; (year of publication is sufficiently earlier than the effective U.S. filed and any foreignpriority date) 2007.

Orr et al.; Shrinkage stresses in bone cement; Biomaterials; 24(17):2933-40; Aug. 2003.

Pan et al., "A study on the friction properties of poly (vinyl alcohol) hydrogel as articular cartilage against titanium alloy," Wear. 262(7-8):1021-5 (2007).

Park et al.; Synthesis of PVA/PVP hydrogels having two-layer by radiation and their physical properties; Radiation Physics and Chemistry; 67(3-4); pp. 361-365; Jun. 2003.

Puska et al.; Exothermal Characteristics and Release of Residual Monomers from Fiber-reinforced Oligomer-modified Acrylic Bone Cement; J Biomat App; 20:51-64; Jul. 2005.

Realdictionary; Definition of Implant; 4pgs. (downloaded Dec. 1, 2013 from www.realdictionary.com/?q=implant).

Revzin et al., "Fabrication of Poly(ethylene glycol) Hydrogel Microstructures Using Photolithography," Langmuir. 17(18):5440-7 (2001).

Saito et al.; Preparation and properties of transparent cellulose hydrogels; J. Applied Polymer Science; 90(11); pp. 3020-3025; Dec. 2003.

Scholes et al.; Compliant layer acetabular cups: friction tsting of a range of materials and designs for a new generation of prosthesis that mimics the natural joint; Proc. IMechE; vol. 220(5); Part H; J. Engineering in Medicine; pp. 583-596, Jul. 2006.

Shalaby; U.S. Appl. No. 61/069,046 entitled "Hydroswellable, segmented, aliphatic polyurethanes and polyurethane ureas," filed Mar. 12, 2008.

Sigma-Aldrich; Methyl Methacrylate (product specification); 1 pg.; Note: this document was available to applicant(s) at least as of (Jun. 19, 2014).

Simon et al., "Study of two Grafting Methods for Obtaining a 3-Aminopropyltriethoxysilane Monolayer on Silica Surface," J Colloid Interface Sci. 251(2):278-83 (2002).

Spector et al.; Porous polymers for biological fixation. Clin Orthop Relat Res, Oct. 1988 (235): p. 207-19.

Stammen et al., Mechanical properties of a novel PVA hydrogel in shear and unconfined compression. Biomaterials, Apr. 2001. 22(8): p. 799-806.

Stryker Orthopaedics; SimplexTM P Bone Cement; Product Literature LSB Rev. 3, Mar. 2006.

Swieszkowski et al., "An elastic material for cartilage replacement in an arthritic shoulder joint," Biomaterials. 27(8):1534-41 (2006).

Tanaka et al.; Polymer properties on resins composed of UDMA and methacrylates with the carboxyl group; Dental Materials Journal; 20(3); pp. 206-215; Sep. 2001.

(56) References Cited

OTHER PUBLICATIONS

Tariq et al.; (Abstract) Sodium benzoate attenuates iminodipropionitrile-induced behavioral syndrome in rats. Behav pharmacol; Dec. 2004.
Tawfik, Dan; Amidation of carboxyl groups; The Protein Protocols Handbook, 2nd Ed.; Humana Press; pp. 477-478; Feb. 2002.
The Engineering Toolbox; Polyurethane insulation: {http://www.engineeringtoolbox.com/polyurethane-insulation-k-values-d_117-4.html} pp. 1-3; printed Oct. 21, 2011.
The Engineering Toolbox;Thermal conductivity of some common materials and gases: {http://www.engineeringtoolbox.com/thrmal-conductivity-d_429.html} pp. 1-2; printed Oct. 21, 2011.
The Gorilla Glue Company; Material Safety Data Sheet; "New Fast Cure-Dries White Gorilla Glue.RTM."; Jan. 30, 2007.
The Gorilla Glue Company; Material Safety Data Sheet; "New Stronger-Faster Gorilla Glue.RTM."; Jan. 26, 2007.
Van Landuyt et al.; Reinforcement of Osteosynthesis Screws with Brushite Cement; Bone; 25(2)(Suppl 1):95S-98S; Aug. 1999.
Wittemann et al.; Adsorption of proteins on spherical polyelectrolyte brushes in aqueous solution; Phys. Chem. Chem. Phys., Mar. 2003, vol. 5(8), pp. 1671-1677.
Wright et al., Wear studies on prosthetic materials using the pin-on-disc machine. Biomaterials, vol. 3, Issue 1, Jan. 1982, pp. 41R48.
Written Opinion for International Application No. PCT/US08/01642, dated May 16, 2008 (5 pages).
Written Opinion for International Application No. PCT/US16/46350, dated Oct. 14, 2016 (8 pages).
Written Opinion for International Application No. PCT/US19/42193, dated Sep. 27, 2019 (6 pages).
Written Opinion for International Application No. PCT/US2008/004976, dated Oct. 15, 2009 (6 pages).
Xiao et al., "Covalent Attachment of Cell-Adhesive, (Arg-Gly-Asp)-Containing Peptides to Titanium Surfaces," Langmuir.14(19):5507-16 (1998).
Yang et al.; Preparation of poly(acrylic acid) modified polyurethane membrane for biomaterial by UV radiation without degassing; J. Biomed. Mater. Res.; vol. 45(2); pp. 133-139; May 1999.
Yim et al., Biocompatibility of poly(ethylene glycol)/poly(acrylic acid)interpenetrating polymer network hydrogel particles inRAW 264.7 macrophage and MG-63 osteoblast cell lines. Journal of Biomedical Materials Research, 91A(3); pp. 894-902; Dec. 1, 2009.
Zhu et al.; (Abstract) Promoting the cytocompatibility of polyurethane scaffolds via surface photo-grafting polymerization of acrylamide; J. Mater. Sci. Mater. Med.; vol. 15; No. 3; pp. 283-289; Mar. 2004.

\* cited by examiner

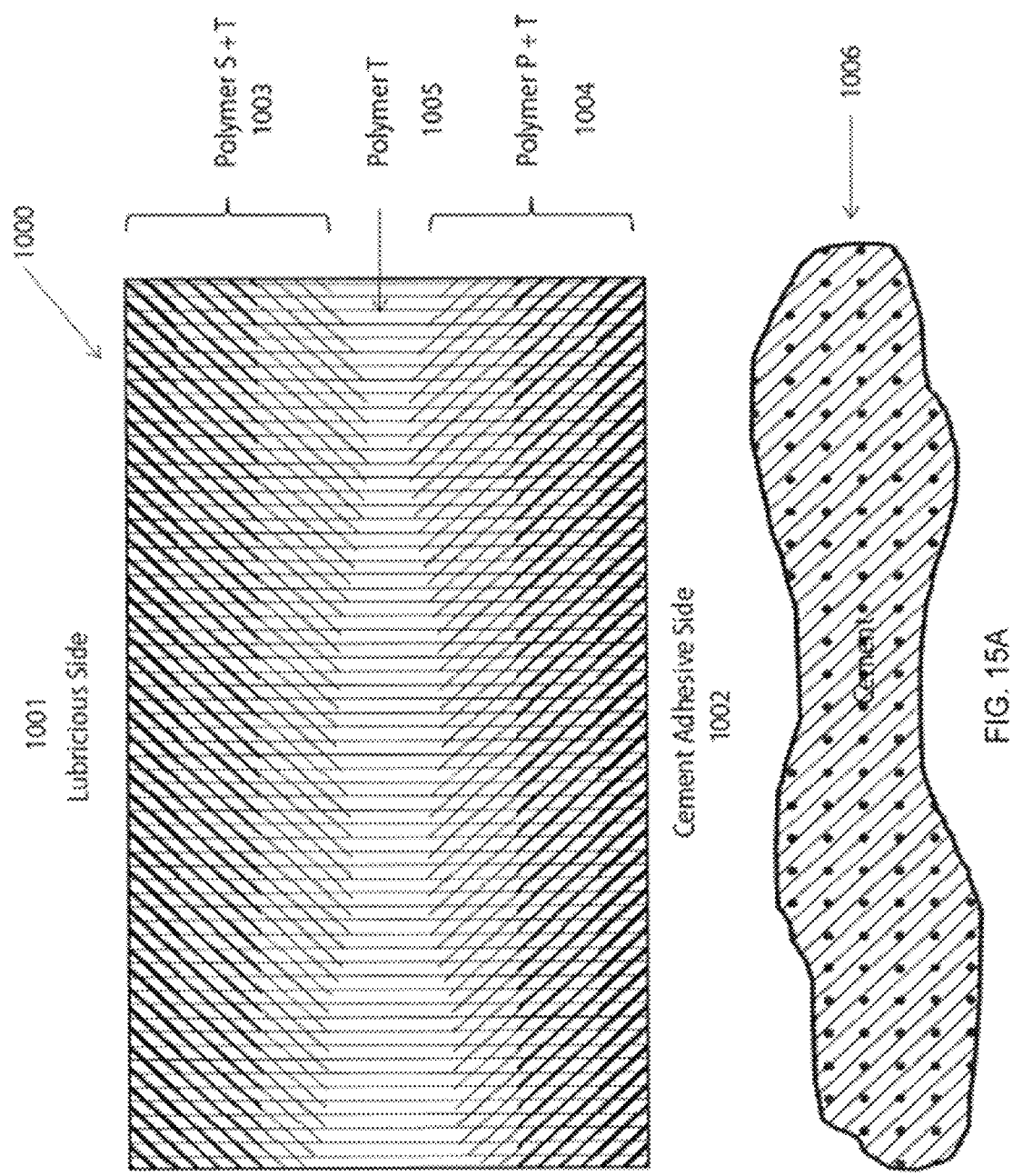

INTERPENETRATING POLYMER NETWORKS

CROSS REFERENCE TO RELATED APPLICATIONS

The present application is a continuation-in part of U.S. patent application Ser. No. 15/752,168 filed Feb. 12, 2018 entitled "Interpenetrating Polymer Networks," which is a National Stage Entry of Patent Application number PCT/US16/46350, filed Aug. 10, 2016 entitled "Interpenetrating Polymer Networks," which claims the benefit of U.S. Provisional Patent Application Ser. No. 62/202,921 filed on Aug. 10, 2015 titled "Interpenetrating Polymer Networks." The present application is also a continuation-in part of U.S. Patent Application Ser. No. 62/619,036 filed Jan. 18, 2018 entitled "Interpenetrating Polymer Networks." The disclosures of each of the foregoing Applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present disclosure pertains to semi- and fully interpenetrating polymer networks, methods of making semi- and fully interpenetrating polymer networks, articles useful in various medical fields such as orthopedics, cardiovascular, neurovascular and urology made from such semi- and fully interpenetrating polymer networks, and methods of using such articles.

BACKGROUND

Fully interpenetrating polymer networks (IPN's) and semi-interpenetrating polymer networks ("semi-IPN's") have been created from a variety of starting materials and have been used for a variety of applications. IPN's and semi-IPNs can combine the beneficial properties of the polymers from which they are made and can avoid some of the undesirable properties of their component polymers.

Prior IPN's and semi-IPNs have been proposed for use in biomedical applications, such as a coating for an implant or as artificial cartilage. See, e.g., U.S. Patent Publ. No. 2005/0147685; U.S. Patent Publ. No. 2009/0035344; and U.S. Patent Publ. No. 2009/008846, U.S. Patent Publ. No. 2013/0138210, U.S. Patent Publ. No. 2012-0045651, U.S. Patent Publ. No. 2012/0209396, U.S. Patent Publ. No. 2013/0217829, U.S. Patent Publ. No. 2012/0232657, and U.S. Patent Publ. No. 2014/0172098. US 2012/0209396 to David Myung et al. describes IPN compositions including a two network IPN composition that can include sulfonic acid functional groups. The utility of prior IPNs and semi-IPNs for their proposed applications is limited by the properties of those compositions, however. In addition, the starting materials and processes of making such prior compositions limit not only the resulting properties of the IPN or semi-IPN but also the commercial viability of the manufacturing processes and the articles made in such processes. Also, the mechanical properties of prior IPNs and semi-IPNs are often limited by the mechanical properties of the component polymers used, which in the case of most intrinsically hydrophilic, water-swellable polymers, are usually quite low. For example, the prior art has not described making a water-swellable IPN or semi-IPN from commercially available hydrophobic thermoset or thermoplastic polymers, such as polyurethane or Poly(Acrylonitrile Butadiene Styrene) (ABS).

Finally, the utility of prior IPN and semi-IPN compositions and the value of the articles formed from such compositions have been limited by the inability to create IPN's and semi-IPNs with desired characteristics, such as strength, lubricity and wear-resistance.

The prior art has also not provided joint implants that fully address the loss of motion and pain experienced by individuals suffering from arthritis or other joint damage. When less invasive methods fail, patients suffering from joint problems can undergo total joint arthroplasty (TJA) or joint resurfacing. The joint is opened, damaged or diseased bone is removed, and an implant is placed in the joint. Implants made from metal, ceramic and/or ultra-high molecular weight polyethylene (UHMWPE) have been used in orthopedic joint arthroplasty or joint replacement for a number of years. Surgeons have experience replacing one or both sides of a joint. They can replace both sides with the same material; if the material is metal then a metal-on-metal articulation is created. They can replace each side of the joint with a different material to create a mixed articulation, such as metal-on-polyethylene.

Although a large number of patients undergo joint replacement surgery each year (an estimated 540,000 patients in the U.S. undergo knee arthroplasty annually), metal, ceramic, and UHMWPE implants in joints can cause adverse local and remote tissue responses. The responses may be due to inherent characteristics of the implant, changes in the implant material over time, or release of material from the implant. A prosthetic joint implant experiences significant friction, motion, pressure, and chemical changes over the course of many years. As time goes by, the implant may corrode or may release ions or debris, such as metal ions or wear particles. The ions or particles may remain in the joint area or may travel through the blood to other parts of the body. The implant or the debris or ions it releases may cause bone resorption (osteolysis), inflammation, metal toxicity, pseudo-tumors, pain, and other problems. In some cases, the implant may loosen and require replacement, using a procedure called revision surgery. In revision surgery, the old, unwanted implant is removed, additional damaged or diseased joint and/or bone material is removed to create a clean, strong surface for attaching the implant, and a new implant is placed. Revision surgeries are expensive, painful, sometimes result in dangerous and hard-to-treat infections, and require long recovery and rehabilitation time.

More recently, hydrogel polymers have been suggested for use in joint implants as alternatives to the metal, ceramic, and UHMWPE implants. U.S. 2004/0199250 by Fell describes a knee prosthesis with a hydrogel coating portion and a high modulus supporting portion for placement into a body joint without requiring bone resection. U.S. 2006/0224244 to Thomas et al. describes a hydrogel implant for replacing a portion of a skeletal joint. The implant has a hydrogel bearing surface with high water content and lower strength and rigidity mounted to a support substrate. U.S. 2008/0241214 to Myung et al. describes the attachment of a hydrogel polymer to a metal assembly. The surface of the metal assembly is modified using an inorganic material and the hydrogel polymer is attached using an intervening polymer network. The assembly may be used as an orthopedic implant. These hydrogel polymers, however, do not adequately recreate the original anatomy, shape, or strength of the joint.

What are needed are materials and methods which overcome the above and other disadvantages of known joint replacement or joint resurfacing implants and procedures.

SUMMARY OF THE DISCLOSURE

The present invention relates generally to articles having an interpenetrating polymer network.

In general, in one embodiment, an orthopedic implant including a bone interface member having a bone contact surface; and a water swellable, water permeable interpenetrating polymer network (IPN) or semi-IPN member having a bearing surface and an attachment zone, the attachment zone being attached to the bone interface member, the water swellable IPN or semi-IPN member including a first polymer network including a hydrophobic thermoset or thermoplastic polymer, a second polymer network including a non-ionic polymer, and a third polymer network including an ionic polymer containing sulfonic acid functional groups, the water swellable, water permeable IPN or semi-IPN member including a compositional gradient between the bearing surface and the attachment zone. In another embodiment, an orthopedic implant is provided in which both sides of the implant have a bearing surface configured such that the central-most aspect of the implant contains the lowest hydration level and the outer bearing surfaces have the highest hydration level.

This and other embodiments can include one or more of the following features. The second network can include the non-ionic polymer including polymerized monomers including one or more of: N-vinyl pyrrolidone (NVP), dimethylacrylamide (DMAA), acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide, and combinations thereof. The second polymer network can also include a co-polymer network of both non-ionic and ionic monomers. In one embodiment, such a co-polymer second network is comprised of dimethylacrylamide and 2-acrylamido 2-methyl propane sulfonic acid (AMPS) and in another embodiment, it is comprised of N-vinyl pyrrolidone and AMPS. The third polymer network can include an ionic polymer containing sulfonic acid groups can include polymerized monomers including one or more of: 2-acrylamido 2-methyl propane sulfonic acid (AMPS), 2-Propene-1-sulfonic acid, 2-Methyl-2-propene-1-sulfonic acid, 1,3-Propanesulfone, 1,4 butane sulfone, vinyl sulfonic acid, anetholesulfonic acid, and styrenesulfonic acid. The third polymer network including the ionic polymer containing sulfonic acid groups can include polymerized 2-acrylamido 2-methyl propane sulfonic acid (AMPS). The third polymer network including the ionic polymer containing sulfonic acid groups can include polymerized acrylic acid and vinyl sulfonic acid. The second polymer network including the non-ionic polymer can include polymerized hydroxyethyl methacrylate or N-vinyl pyrrolidone and the third polymer network including the ionic polymer containing sulfonic acid groups includes polymerized 2-acrylamido 2-methyl propane sulfonic acid (AMPS). The third polymer network including the ionic polymer containing sulfonic acid groups can include polymerized 2-acrylamido 2-methyl propane sulfonic acid (AMPS) and acrylic acid. The third polymer network including the ionic polymer containing sulfonic acid groups can include about 1% to about 100% sulfonic acid groups relative to a total number of functional groups of the third polymer network. The bearing surface can have a coefficient of friction of less than about 0.1. The bearing surface can have a coefficient of friction of less than about 0.05. The bearing surface can have a coefficient of friction of less than about 0.01. The bearing surface can have a coefficient of friction of less than about 0.005. The compositional gradient can form a stiffness gradient. One of the second and third polymer networks can form a composition and hydration gradient from a first portion of the implant to a second portion of the implant. The bone interface member can include a metal. The metal includes a porous metal. The attachment zone can be attached to the porous metal of the bone interface member with a bone cement. The attachment zone can be attached to the porous metal of the bone interface member through interdigitation. The bone interface member can include a ceramic or a polymer. At least a portion of the orthopedic implant can be configured to change a shape during implant placement in a joint. At least a portion of the implant can be configured to transiently deform during implant placement in a joint. An attachment of the attachment zone to the bone interface member can be created by an adhesive. The third polymer network can include the ionic polymer third polymer network including a fixed charge. The ionic polymer can include a majority of sulfonic groups relative to other functional groups. The implant can have a shape selected from the group consisting of: a cap, a cup, a plug, a mushroom, a cylinder, a patch, and a stem. The implant can be adapted to fit an acromioclavicular joint, an ankle joint, a condyle, an elbow joint, a hand joint including a metacarpal joint, a finger joint, a thumb joint, a base of thumb joint, a glenoid, a hip joint including an acetabular joint, an intervertebral disc, a vertebral joint, including an intervertebral facet joint, a labrum, a meniscus, a foot joint, including a metatarsal joint and a toe joint, a patella, a tibial plateau, a jaw joint including a temporomandibular joint, a knee joint including a knee medial compartment joint, a patellofemoral joint, and a total knee joint, a knee meniscus, a shoulder joint including a iabral joint, or a wrist joint and any portion thereof. The first polymer network can include polyurethane. The implant can further include an additive within the water swellable, water permeable IPN or semi-IPN member, the additive can include one or more of: a steroid, anti-inflammatory agent, antioxidant, antibiotic, and anti-microbial agent. The implant can further include an adhesive gradient between the attachment zone and the bearing surface, the adhesive gradient can have a highest concentration of adhesive at the attachment zone. The adhesive gradient can include a polymerized bone cement. The adhesive gradient can include a urethane dimethacrylate-methyl methacrylate copolymer including a plurality of first polymer regions based on urethane dimethacrylate and a plurality of second polymer regions based on methyl methacrylate. The first polymer regions based on urethane dimethacrylate can include about 60%-99% (w/w) of the copolymer and the second polymer regions based on methyl methacrylate can include about 1%-40% (w/w) of the copolymer. The first polymer regions based on urethane dimethacrylate can include about 60%-80% (w/w) of the copolymer and the second polymer regions based on methyl methacrylate can include from about 20%-40% (w/w) of the copolymer. The first polymer regions based on urethane dimethacrylate can include soft segments based on poly(tetramethyl) glycol, the soft segments can have a molecular weight between about 100 Da and about 5000 Da. The urethane dimethacrylate-methyl methacrylate copolymer can define a compressive modulus between about 30 MPa and about 2000 MPa. The urethane dimethacrylate-methyl methacrylate copolymer can define a tensile modulus between about 30 MPa and 2000 MPa. The urethane dimethacrylate-methyl methacrylate copolymer can define a failure strain between about 25% and about 200%.

In general, in one embodiment, a composition is provided including: a water swellable, a water permeable interpenetrating polymer network (IPN) or semi-IPN member including a first polymer network including a hydrophobic thermoset or thermoplastic polymer, a second polymer network including a non-ionic polymer or a co-polymer comprising both a non-ionic and ionic polymer, and a third polymer network including an ionic polymer containing sulfonic acid functional groups, the water swellable, water permeable IPN or semi-IPN member including a compositional gradient between a first surface and a second surface. In one embodiment, sulfonic acid moieties are present in both the second and third networks. The third network may also be comprised of both an ionic (e.g. AMPS) and a non-ionic network (e.g. DMAA or NVP).

This and other embodiments can include one or more of the following features. The first surface can include a lubricious surface. The lubricious surface can have a coefficient of friction of less than about 0.1. The bearing surface can have a coefficient of friction of less than about 0.05. The lubricious surface can have a coefficient of friction of less than about 0.01. The lubricious surface can have a coefficient of friction of less than about 0.005. The second network including the non-ionic polymer can include polymerized monomers including one or more of: N-vinyl pyrrolidone, dimethylacrylamide, acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide, and combinations thereof.

The second polymer network including the non-ionic polymer can include polymerized hydroxyethyl methacrylate. The third polymer network including an ionic polymer containing sulfonic acid groups can include polymerized monomers including one or more of: 2-acrylamido 2-methyl propane sulfonic acid (AMPS), 2-Propene-1-sulfonic acid, 2-Methyl-2-propene-1-sulfonic acid, 1,3-Propanesulfone, 1,4 butane sulfone, vinyl sulfonic acid, anetholesulfonic acid, and styrenesulfonic acid. The third polymer network including the ionic polymer containing sulfonic acid groups can include polymerized 2-acrylamido 2-methyl propane sulfonic acid (AMPS). The second polymer network including the non-ionic polymer can include polymerized hydroxyethyl methacrylate and the third polymer network including the ionic polymer containing sulfonic acid groups includes polymerized 2-acrylamido 2-methyl propane sulfonic acid (AMPS). The third polymer network including the ionic polymer containing sulfonic acid groups can include polymerized 2-acrylamido 2-methyl propane sulfonic acid (AMPS) and acrylic acid. The first polymer network can include polyurethane. The third polymer network including the ionic polymer containing sulfonic acid groups can include about 1% to about 100% sulfonic acid groups relative to a total number of functional groups of the third polymer network. The compositional gradient can form a stiffness gradient. One of the second or third polymer networks can form a hydration gradient from a first portion of the implant to a second portion of the implant. The composition can be adapted for use as a bearing.

In general, in one embodiment, a method of forming an interpenetrating polymer network (IPN) in a polymer composition including: contacting the polymer composition including a first polymer network of a hydrophobic thermoset or thermoplastic polymer with a non-ionic monomer solution; polymerizing the non-ionic monomer to form a second polymer network including the polymerized non-ionic monomer in the polymer composition; contacting the polymer composition with a solution of an ionic monomer containing sulfonic acid functional groups; and polymerizing the ionic monomer to form a third polymer network including the polymerized ionic monomer in the polymer composition.

This and other embodiments can include one or more of the following features. The non-ionic monomer can include one or more of: N-vinyl pyrrolidone, dimethylacrylamide, acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide, and combinations thereof. The ionic monomer containing sulfonic acid groups includes one or more of: 2-acrylamido 2-methyl propane sulfonic acid (AMPS), vinyl sulfonic acid, anetholesulfonic acid, and styrenesulfonic acid. The ionic monomer containing sulfonic acid groups can include polymerized 2-acrylamido 2-methyl propane sulfonic acid (AMPS). The non-ionic monomer can include N-vinyl pyrrolidone, dimethylacrylamide and/or hydroxyethyl methacrylate (with or without AMPS) and the ionic monomer containing sulfonic acid groups includes 2-acrylamido 2-methyl propane sulfonic acid (AMPS). The ionic polymer containing sulfonic acid groups can include 2-acrylamido 2-methyl propane sulfonic acid (AMPS) with or without acrylic acid. The polymerized ionic polymer containing sulfonic acid groups can include about 1% to about 100% sulfonic acid groups relative to a total number of functional groups of the third polymer network. The first polymer network can include polyurethane. The method can further include providing a photo-initiator with the non-ionic monomer and polymerizing the photo-initiator with the non-ionic monomer to crosslink the second polymer network. The method can further include providing a photo-initiator with the ionic monomer and polymerizing the photo-initiator with the ionic monomer to crosslink the third polymer network. The polymer composition can include a bearing surface and an attachment zone can be adapted to be attached to a bone interface member having a bone contact surface. The method can further include forming a compositional gradient between the bearing surface and the attachment zone. The compositional gradient can form a stiffness gradient. One of the second or third polymer networks can form a hydration gradient between the bearing surface and the attachment zone. The composition gradient can include an adhesive gradient, the adhesive gradient can have a highest concentration of adhesive at the attachment zone. The adhesive gradient can be formed by polymerizing a bone cement within the polymer composition. The adhesive gradient can include a urethane dimethacrylate-methyl methacrylate copolymer including a plurality of first polymer regions based on urethane dimethacrylate and a plurality of second polymer regions based on methyl methacrylate. The bone interface member can be a metal. The metal can be a porous metal. The bone interface member can include a ceramic or a polymer. The method can further include creating an attachment of the attachment zone to the bone interface member using an adhesive. The method can further include shaping or forming the polymer composition to a desired shape. The desired shape can be selected from the group consisting of: a cap, a cup, a plug, a mushroom, a cylinder, a patch, and a stem. The desired shape can be adapted to fit an acromioclavicular joint, an ankle joint, a condyle, an elbow joint, a hand joint including a metacarpal joint, a finger joint, a thumb joint, a base of thumb joint, a glenoid, a hip joint including an acetabular joint, an intervertebral disc, a vertebral joint, including an intervertebral facet joint, a labrum, a meniscus, a foot joint, including a metatarsal joint and a toe joint, a patella, a tibial plateau, a jaw joint including a temporomandibular joint, a knee joint including a knee medial compartment joint, a patellofemoral joint, and a total knee joint, a knee meniscus a shoulder joint including a labral joint, or a wrist joint and any portion thereof. The method can further include adding an additive to the polymer composition, the additive can include one or more of: a steroid, anti-inflammatory agent, antioxidant, antibiotic, and anti-microbial agent.

In general, in one embodiment, the present disclosure pertains to sterile packaged products that contain implants, including orthopedic implants described elsewhere herein, which comprise an interpenetrating polymer network (IPN) or semi-IPN member comprising a first polymer network, a second polymer network, and a third polymer network. In embodiments, the implants are at least partially immersed in a divalent-cation-containing solution comprising water and one or more divalent metal cations. The divalent-cation-containing solution may be, for example, a simulated body fluid that contains physiologic levels of ions found in the body fluids such as synovial fluid or blood serum or cerebrospinal fluid. In certain embodiments, the divalent-cation-containing solution may comprise 0.1 to 5 mM total divalent metal cations. In embodiments, the divalent-cation-containing solution may comprise calcium ions, magnesium ions or a combination of calcium ions and magnesium ions. For instance, the divalent-cation-containing solution may comprise 0.5 to 5.0 mM calcium ions, typically 0.5 to 2.0 mM calcium ions, more typically 0.8 to 1.6 mM calcium ions, and in some embodiments 1.1 to 1.3 mM calcium ions, among other possibilities and/or the divalent-cation-containing solution may comprise 0.2 to 1.5 mM magnesium ions, typically 0.3 to 1.0 mM magnesium ions, and in some embodiments, 0.5 to 0.7 mM magnesium ions, among other possibilities. In embodiments, the divalent-cation-containing solution may further comprise monovalent metal ions selected from sodium ions, potassium ions, or a combination of sodium and potassium ions, in which case the divalent-cation-containing solution may contain 0 to 300 mM total monovalent metal cations, among other possibilities.

In general, in one embodiment, the present disclosure pertains to implants, including orthopedic implants described elsewhere herein, which comprise an interpenetrating polymer network (IPN) or semi-IPN member comprising a first polymer network, a second polymer network, and a third polymer network, wherein the IPN or semi-IPN maintains dimension and mechanical properties under divalent conditions.

In general, in one embodiment, the present disclosure pertains to implants, including orthopedic implants described elsewhere herein, which comprise an interpenetrating polymer network (IPN) or semi-IPN member comprising a first polymer network, a second polymer network, and a third polymer network, wherein the IPN or semi-IPN member maintains water content (i.e., within a range of ±5 wt %, preferably ±2 wt %, more preferably ±1 wt %) throughout a physiologic range of divalent ion concentrations found in living organisms, including synovial fluid of living organisms, particularly mammals, more particularly human beings.

In general, in one embodiment, the present disclosure pertains to implants, including orthopedic implants described elsewhere herein, which comprise an interpenetrating polymer network (IPN) or semi-IPN member comprising a first polymer network, a second polymer network, and a third polymer network, wherein the IPN or semi-IPN member demonstrates an absolute % weight change per mM change in total divalent cation concentration of less than 3%, preferably less than 2%, more preferably less than 1% (ideally demonstrating no measurable weight change), for example, demonstrating such properties over a total divalent cation concentration range of from about 0.1 mM to about 5 mM, including a total divalent ration concentration ranging from hypo-physiological divalent cation levels of 1.4 mM (0.96 mM $Ca^{2+}$, 0.48 mM $Mg^{2+}$) to hyper-physiological divalent ration levels of 2.2 mM (1.44 mM $Ca^{2+}$, 0.72 mM $Mg^{2+}$).

In general, in one embodiment, the present disclosure pertains to implants, including orthopedic implants described elsewhere herein, which comprise an interpenetrating polymer network (IPN) or semi-IPN member comprising a first polymer network, a second polymer network, and a third polymer network, wherein the IPN or semi-IPN maintains a coefficient of friction of less than 0.1, preferably less than 0.075, more preferably less than 0.05, over a total divalent cation concentration range of about 0.1 mM to about 5 mM. including over a physiologic total divalent cation concentration range of about 1.4 mM (0.96 mM $Ca^{2+}$, 0.48 mM $Mg^{2+}$) to about 2.2 mM (1.44 mM $Ca^{2+}$, 0.72 mM $Mg^{2+}$).

In general, in one embodiment, the present disclosure pertains to systems that comprise an implant, for example, selected from orthopedic implants described elsewhere herein, which comprise an interpenetrating polymer network (IPN) or semi-IPN member comprising a first polymer network, a second polymer network, and a third polymer network, and an adhesive kit comprising a bonding agent (e.g., such as a solvent, cement, or glue).

This and other embodiments can include one or more of the following features. The adhesive kit can include a first reservoir including a first mixture including at least one of a urethane dimethacrylate oligomer and a methyl methacrylate monomer; at least one of a photoinitiator and a thermal initiator; and an inhibitor, a second reservoir including a second mixture including at least one of a urethane dimethacrylate monomer and a methyl methacrylate monomer; and an accelerator; and an instruction for use wherein at least one of the first reservoir and the second reservoir can include a urethane dimethacrylate monomer and at least one of the first reservoir and the second reservoir can include a methyl methacrylate monomer.

Both the first reservoir and the second reservoir can include a urethane dimethacrylate monomer and a methyl methacrylate monomer. The second reservoir can further include an inhibitor. The system can further include poly(methyl methacrylate). The system can further include a third reservoir including a poly(methyl methacrylate) powder. The first mixture, the second mixture and the poly(methyl methacrylate) can define a component weight, and a weight of the poly(methyl methacrylate) powder can include from about 1% to about 70% of the component weight. The system can further include a polystyrene. The system can further include a photoinitiator and a thermal initiator. The first reservoir can include a first chamber in a syringe and the second reservoir can include a second chamber in the syringe, wherein the syringe can be configured to combine the first mixture with the second mixture to create an adhesive mixture. The system can further include a nozzle connected with the syringe configured to dispense the adhesive mixture. The first reservoir and the second reservoir each can include from about 0% (w/w) to about 100% (w/w), typically, from about 1% (w/w) to about 99% (w/w), urethane dimethacrylate oligomer and/or 0% (w/w) to about 100% (w/w), typically, from about 1% (w/w) to about 99% (w/w), methyl methacrylate. The first reservoir and/or the second reservoir each can include from about 0% (w/w) to about 100% (w/w), typically, from about 1% (w/w) to about 99% (w/w), methyl methacrylate. The at least one initiator can include a photoinitiator including between 0% (w/w) and about 5% (w/w), typically, from about 1% (w/w) to about 5%, (w/w), camphorquinone. The at least one initiator can include a thermal initiator including between 0% (w/w) and about 5% (w/w), typically, from about 1% (w/w) to about 5% (w/w), benzoyl peroxide. The accelerator can include between 0% (w/w) and about 5% (w/w), typically, from about 1% (w/w) to about 5% (w/w), N,N-dimethyl-p-toluidine. The inhibitor can include between 0% (w/w) and about 5% (w/w), typically, from about 1% (w/w) to about 5% (w/w), hydroquinone. The system can further include an additive configured to prevent an infection. The system can further include an antibiotic. The system can further include a radiopaque material. The first mixture can define a viscosity between about 1 Pa·S and 5000 Pa·S.

In one embodiment, the adhesive kit can be comprised by a single reservoir that contains from about 0% (w/w) to about 100% (w/w), typically, from about 1% (w/w) to about 99% (w/w), urethane dimethacrylate oligoiner and/or 0% (w/w) to about 100% (w/w), typically, from about 1% (w/w) to about 99% (w/w), methyl methacrylate, from about 0% (w/w) to about 100% (w/w), typically, from about 1% (w/w) to about 99% (w/w), methyl methacrylate, an optional initiator (which can include, for example, at least one of a photoinitiator and a thermal initiator), typically in an amount from about 0% (w/w) to about 5% (w/w), for example, from about 1% (w/w) to about 5% (w/w), and an optional accelerator, typically in an amount from about 0% (w/w) to about 5% (w/w), for example, from about 1% (w/w) to about 5% (w/w). The single reservoir can include a chamber in a syringe. The system can further include a nozzle connected with the syringe configured to dispense the curable adhesive. The initiator can include a photoinitiator including between 0% (w/w) and about 5% (w/w), typically, from about 1% (w/w) to about 5% (w/w), camphorquinone. The accelerator can include between 0% (w/w) and about 5% (w/w), typically, from about 1% (w/w) to about 5% (w/w), N,N-dimethyl-p-toluidine. The inhibitor can include between 0% (w/w) and about 5% (w/w), typically, from about 1% (w/w) to about 5% (w/w), hydroquinone. The system can further include an additive configured to prevent an infection. The system can further include an antibiotic. The system can further include a radiopaque material. The first mixture can define a viscosity between about 1 Pa·S and 5000 Pa·s.

In general, in one embodiment, method of attaching an orthopedic implant within a human body is provided including: providing a water swellable, water permeable interpenetrating polymer network (IPN) or semi-IPN member having a bearing surface and an attachment zone, the water swellable IPN or semi-IPN member including a first polymer network including a hydrophobic thermoset or thermoplastic polymer, a second polymer network including a non-ionic polymer, and a third polymer network including an ionic polymer containing sulfonic acid functional groups; providing a bone cement composition to the attachment zone; and curing the bone cement composition to attach the attachment zone to a surface of a bone or a portion of an orthopedic implant engaged with a surface of a bone within the human body.

This and other embodiments can include one or more of the following features. The second network can include the non-ionic polymer including polymerized monomers including one or more of: N-vinyl pyrrolidone, dimethylacrylamide, acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide, and combinations thereof. The second polymer network can include the non-ionic polymer including polymerized hydroxyethyl methacrylate.

The third polymer network can include an ionic polymer containing sulfonic acid groups including polymerized monomers including one or more of: 2-acrylamido 2-methyl propane sulfonic acid (AMPS), vinyl sulfonic acid, anetholesulfonic acid, and styrenesulfonic acid. The third polymer network can include the ionic polymer containing sulfonic acid groups including polymerized 2-acrylamido 2-methyl propane sulfonic acid (AMPS).

In one embodiment, the third network polymer is formed by template polymerization with the second network polymer within the matrix of the first network polymer. In this embodiment, favorable non-covalent interactions between the third network monomer and the second network polymer side chains are responsible for the swelling of the two-network IPN with the third network monomer, and facilitates template polymerization. In one embodiment, AMPS is template-polymerized along a pre-existing poly-N-vinyl pyrrolidone (PVP) second network within a pre-existing polyurethane network.

In another embodiment, the third network polymer is formed by template polymerization with the second network polymer within the matrix of the first network polymer. In this embodiment, AMPS is template-polymerized along a pre-existing poly-DMAA second network within a pre-existing polyurethane network.

In another embodiment, the presence of PAMPS in the second, co-polymeric network (e.g. PAMPS and poly-DMAA or PAMPS and PVP) improves the swellability of the two-network IPN with AMPS monomers, thus increasing the overall sulfonation of the triple network.

The method can further include forming an adhesive gradient between the attachment zone and the bearing surface, the adhesive gradient can have a highest concentration of adhesive at the attachment zone when curing the bone cement. Curing the bone cement composition can be performed by providing a light source to the bone cement composition. The adhesive gradient can include a urethane dimethacrylate-methyl methacrylate copolymer including a plurality of first polymer regions based on urethane dimethacrylate and a plurality of second polymer regions based on methyl methacrylate. The first polymer regions based on urethane dimethacrylate can include about 60%-99% (w/w) of the copolymer and the second polymer regions based on methyl methacrylate can include about 1%-40% (w/w) of the copolymer. The first polymer regions based on urethane dimethacrylate can include about 60%-80% (w/w) of the copolymer and the second polymer regions based on methyl methacrylate can include from about 20%-40% (w/w) of the copolymer.

The first polymer regions based on urethane dimethacrylate can include soft segments based on poly(tetramethyl)

glycol, the soft segments can have a molecular weight between about 100 Da and about 5000 Da. The urethane dimethacrylate-methyl methacrylate copolymer can define a compressive modulus between about 30 MPa and about 2000 MPa. The urethane dimethacrylate-methyl methacrylate copolymer can define a tensile modulus between about 30 MPa and 2000 MPa. The urethane dimethacrylate-methyl methacrylate copolymer can define a failure strain between about 25% and about 200%.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 15A-15B show an example of a double gradient with a lubricious and adhesive gradient in accordance with some embodiments.

DETAILED DESCRIPTION

Figure 1A:
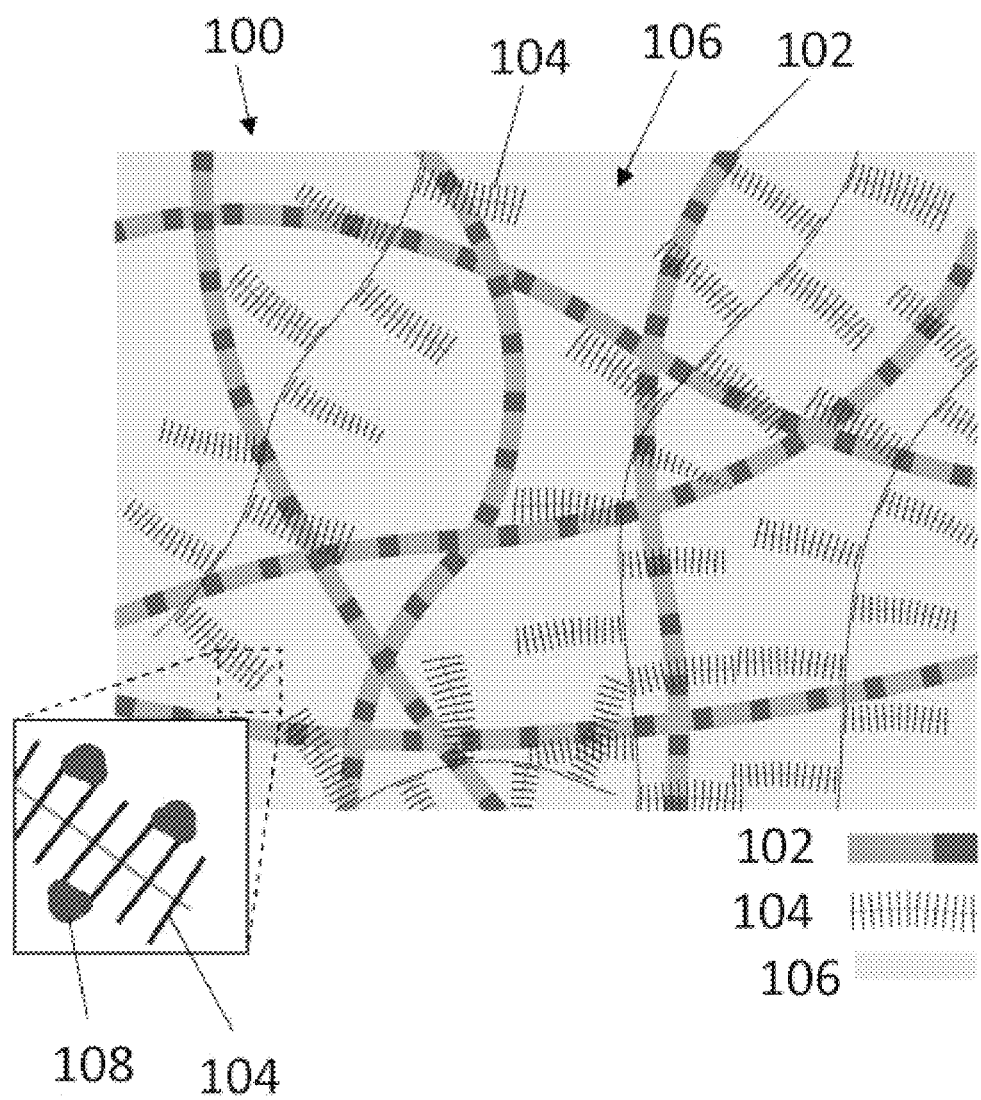
FIG. 1A is a schematic illustration of cartilage microstructure.

The mechanical properties desired for certain medical applications are often outside the range of possibility of many hydrophilic starting materials. Hence, one aspect of the present disclosure takes advantage of the high mechanical strength of hydrophobic starting materials and combines those hydrophobic materials with certain ionic polymers as a useful way to achieve the goal of high mechanical strength in addition to other desirable properties. One aspect of the present disclosure takes strong materials and makes them more water-swellable. One objective is to create a strong yet permeable network that allows, in a controlled fashion, water pressurization and flow throughout the bulk of the material and up to its surface. IPN compositions are disclosed herein that can be formed from a hydrophobic starting material. The IPN compositions can be processed to achieve desired physical and chemical properties. Examples of applications include as a cartilage replacement and as a material for bearings.

For purposes of this application, an "interpenetrating polymer network" or "IPN" is a material comprising two or more polymer networks which are at least partially interlaced on a molecular scale, but not covalently bonded to each other, and cannot be separated unless chemical bonds are broken. A "semi-interpenetrating polymer network" or "semi-IPN" is a material comprising one or more polymer networks and one or more linear or branched polymers characterized by the penetration on a molecular scale of at least one of the networks by at least some of the linear or branched macromolecules. As distinguished from an IPN, a semi-IPN is a polymer blend in which at least one of the component polymer networks is not chemically crosslinked by covalent bonds.

A "polymer" is a substance comprising macromolecules, including homopolymers (a polymer derived one species of monomer) and copolymers (a polymer derived from more than one species of monomer). A "hydrophobic polymer" is a pre-formed polymer network having at least one of the following two properties: (1) a surface water contact angle of at least 45° and (2) exhibits water absorption of 2.5% or less after 24 hours at room temperature according to ASTM test standard D570. A "hydrophilic polymer" is a polymer network having a surface water contact angle less than 45° and exhibits water absorption of more than 2.5% after 24 hours at room temperature according to ASTM test standard D570. An "ionic polymer" is defined as a polymer comprised of macromolecules containing at least 2% by weight ionic or ionizable monomers (or both), irrespective of their nature and location. An "ionizable monomer" is a small molecule that can be chemically bonded to other monomers to form a polymer and which also has the ability to become negatively charged due the presence of acid functional groups such carboxylic acid and/or sulfonic acid. A "thermoset polymer" is one that does not melt when heated, unlike a thermoplastic polymer. Thermoset polymers "set" into a given shape when first made and afterwards do not flow or melt, but rather decompose upon heating and are often highly crosslinked and/or covalently crosslinked. A "thermoplastic polymer" is one which melts or flows when heated, unlike thermoset polymers. Thermoplastic polymers are usually not covalently crosslinked. A "polymer alloy" is an IPN or semi-IPN. A "gradient polymer alloy" is a gradient IPN or semi-IPN (e.g. an IPN or semi-IPN having a compositional gradient) where the composition of the material varies from one aspect of the material to the other. For instance, such a gradient can exist from one side of a material to another, or from the interior of a material to the outer surface of the material. Such a gradient can involve a change in the hydration (water content) of the material, a change in the chemical composition of a material, or both. "Phase separation" is defined as the conversion of a single-phase system into a multi-phase system; especially the separation of two immiscible blocks of a block co-polymer into two phases, with the possibility of a small interphase in which a small degree of mixing occurs.

The present disclosure includes a process for modifying commercially available hydrophobic thermoset or thermoplastic polymers, such as polyurethane or ABS to provide new properties, such as strength, lubricity, electrical conductivity, increased chemical resistance, and wear-resistance. Other possible hydrophobic thermoset or thermoplastic polymers are described below. The disclosure also includes the IPN and semi-IPN compositions as well as articles made from such compositions and methods of using such articles. The IPN and semi-IPN compositions of this disclosure may attain one or more of the following characteristics: High tensile and compressive strength; low coefficient of friction; high water content and swellability; high permeability; biocompatibility; and biostability. The term "permeability" refers to the hydraulic permeability, which is the ease of water to move through the pores of the material. To obtain lubricious properties at high contact stresses, the permeability needs to lie within a certain range.

Improved IPN compositions and methods for making the same are provided herein. One aspect of the present disclosure is improving the properties of IPN compositions such that they have improved resistance to physiological environments encountered by implants within a mammalian body. Examples of physiological environments encountered by implants include blood, plasma, synovial fluid, spinal fluid, serum, and other bodily fluids. For example, the IPN compositions can remain lubricious and have a high water content even when exposed to environments with divalent cations, such as calcium ions, especially those experienced by implants introduced to the body in orthopedic applications. Some IPN embodiments have the tendency to bind divalent ion (such as Calcium or Magnesium) resulting in a low water content. One way to achieve calcium resistance is to introduce a material into the IPN composition having sulfonic acid functional groups. Sulfonic acid provides good resistance to calcium ions; however, it is difficult to incorporate sulfonic acid directly into a hydrophobic thermoset or thermoplastic polymers due to the highly negative charge and low pKa of sulfonic acid functional groups and other incompatibility between the sulfonic acid functional groups and the hydrophobic thermoset or thermoplastic polymers that makes it difficult for the latter to swell with the monomers containing sulfonic acid functional groups. This makes it difficult to form two-network IPNs with hydrophobic thermoset or thermoplastic polymers and sulfonic acid-base polymers.

Improved methods for incorporating sulfonic acid functional groups within an IPN composition are disclosed herein. It has been discovered that incorporation of sulfonic acid can be improved in a first polymer network of the hydrophobic thermoset or thermoplastic polymers by first forming a relatively hydrophilic but non-ionic/neutral second polymer network within the hydrophobic thermoset or thermoplastic polymers. The second polymer network can greatly improve the compatibility of an ionic monomer or macromer having sulfonic acid functional groups with the first polymer network of the hydrophobic thermoset or thermoplastic polymers. The use of the second polymer network can also increase the amount of sulfonic acid groups that can be incorporated within the IPN composition versus a material without a second neutral/non-ionic polymer network.

Addition of sulfonic acid functional groups to materials confer beneficial properties such as lubricity and resistance to binding by divalent or multivalent cations. There are cases where sulfonic acid-containing polymers do not form composites with other polymers very easily or directly. There is, therefore, a need in the art to bring sulfonic acid polymers into composites with other polymers. In a preferred embodiment, a non-ionic polymer acts as an intermediary between a first polymer and a sulfonic acid-containing polymer. This non-ionic polymer forms an IPN with the first polymer, which renders the IPN now miscible with the monomers of the sulfonic acid polymer, and then the sulfonic acid monomers are polymerized in the presence of the first IPN to form a three-network IPN. In cases of a hydrophobic first network, without the intermediary non-ionic polymer, the amount of sulfonic acid polymer relative to the first network polymer would be relatively low.

In some embodiments a water swellable, water permeable interpenetrating polymer network (IPN) or semi-IPN member is provided. The water swellable IPN or semi-IPN member includes a first polymer network comprising a hydrophobic thermoset or thermoplastic polymer, a second polymer network comprising a non-ionic polymer, and a third polymer network comprising an ionic polymer containing sulfonic acid functional groups. The water swellable, water permeable IPN or semi-IPN member can optionally including a compositional gradient between a first surface and second surface of the water swellable, water permeable IPN or semi-IPN member. In one example the first polymer network comprises polyurethane, and in some examples, comprises polyether urethane (PEU).

In some cases, the hydrophobic thermoset or thermoplastic polymer can include multiple subsets of polymer segments. The compatibility of the segments, such as hard and soft segments, can have varying compatibility with the ionic monomers and non-ionic/neutral monomers used to make the second polymer network and third polymer network. Depending on the compatibility of the subsets of polymer segments in the hydrophobic thermoset or thermoplastic polymer with the ionic and non-ionic monomers, the second polymer network and the third polymer network may form in all of the subsets of polymer segments or only a portion of the subsets of polymer segments. For example, the second polymer network and third polymer network are each formed within the same subset of polymer segments of the hydrophobic thermoset or thermoplastic polymer. In some embodiments the second polymer network and third polymer network are each formed within just the soft segments and not the hard segments of the hydrophobic thermoset or thermoplastic polymer.

The second network comprising the non-ionic polymer can include polymerized monomers including one or more of: N-vinyl pyrrolidone, dimethylacrylamide, acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide, and combinations thereof.

The third polymer network comprising an ionic polymer containing sulfonic acid groups can include polymerized monomers including one or more of: 2-acrylamido 2-methyl propane sulfonic acid (AMPS), 2-Propene-1-sulfonic acid, 2-Methyl-2-propene-1-sulfonic acid, vinyl sulfonic acid, 1,3-Propanesulfone, 1,4 butane sulfone, anetholesulfonic acid, and styrenesulfonic acid.

In some embodiments the third polymer network comprising the ionic polymer containing sulfonic acid groups includes polymerized 2-acrylamido 2-methyl propane sulfonic acid (AMPS). In some embodiments the second polymer network comprising the non-ionic polymer includes polymerized hydroxyethyl methacrylate and the third polymer network comprising the ionic polymer containing sulfonic acid groups includes polymerized 2-acrylamido 2-methyl propane sulfonic acid (AMPS).

Any of the first polymer network, second polymer network, and third polymer networks can be a co-polymer or a combination of a plurality of different monomers. In some embodiments the second polymer network can also include poly (acrylic acid). For example, the second polymer network can include a co-polymer polymerized acrylic acid (PAA) and polymerized hydroxyethyl methacrylate. In some embodiments the third polymer network can also include acrylic acid. For example, the third polymer network can include a co-polymer polymerized 2-acrylamido 2-methyl propane sulfonic acid (AMPS) and acrylic acid. In another example the third polymer network can include a co-polymer polymerized vinyl sulfonic acid and acrylic acid.

The third polymer network comprising the ionic polymer containing sulfonic acid groups can include about 1% to about 100% sulfonic acid groups relative to a total number of functional groups of the third polymer network. The ionic polymer can include a majority of sulfonic groups relative to other functional groups. The third polymer network can include a fixed charge.

In some embodiments the second polymer is comprised by a mixture of ionic and non-ionic monomers that are tuned to match the Hansen solubility parameters ($\delta_d$, $\delta_p$, $\delta_h$) of the first polymer and allows swelling of the latent. The mixture can be comprised by a single or any combinations of ionic monomers and a non-ionic monomer. For instance, the ionic part of the mixture can be comprised by a combination of acrylic acid and vinyl sulfonic acid, and the non-ionic part of hydroxyethyl methacrylate.

The swelling Hansen solubility parameters of the first polymer are matched using a system of one or more solvents and an ionic monomer. For example, the mixture can be comprised by a mixture of AMPS, formic acid and water.

The second polymer is comprised by a mixture of ionic monomers and solvents that are tuned to match the Hansen solubility parameters of only one segment of the first co-polymer. For example, a mixture of an ionic monomer and a solvent will affect only the soft segment of the polyurethane polymer.

The swelling Hansen solubility parameters of the first polymer or the solubility parameters of one or more segments of the first polymer are matched with the solubility parameter of the monomers or a mixture of monomers and solvents. After the polymerization of the second polymer, the combined swelling Hansen solubility parameters of the first and second IPN are matched with the monomer of the third polymer or a mixture of monomers and solvents. The same procedure can be repeated to add forth network and so on. For example, polyurethane is swelled with benzyl alcohol and hydroxyethyl methacrylate that has tuned Hansen solubility parameters to swell the polyurethane; after polymerization the new Hansen solubility parameters are estimated for the new IPN and are matched with the solubility parameters of a solution of acrylic acid and 2-methyl propane sulfonic acid of the third IPN network.

In some embodiments, the second polymer can have reactive groups that can chemically react with other ionic molecules. For example, the second polymer can be (dimethylamino)ethyl methacrylate and the ionic molecule 1,3 propane sulfone.

The IPN compositions can include one or more compositional gradients in any or all of the first polymer network, second polymer network, and third polymer network. In one example the compositional gradient forms a stiffness gradient. In another example the compositional gradient can be an adhesive gradient, formed by an adhesive like bone cement. In another example the compositional gradient can be a hydration gradient. For example, one of the second and third polymer networks can have a hydration gradient from a first portion of the implant to a second portion of the implant. In still another example, the third polymer network can create a charge gradient from a first portion of the implant to a second portion of the implant. The gradient can be established by second network (a hydration gradient) into which the third network is formed as a gradient by necessity due to the constraint of free volume as a function of distance from the surface. Alternatively, the gradient can be formed by differential swelling of the third network monomer into the second network that is formed through-and-through (without a gradient) with the first network.

The IPN compositions described herein can provide improved water swelling and frictional properties by exhibiting resistance to binding with divalent metal cations. Examples of divalent metal cations include calcium and magnesium in particular.

The IPN compositions described herein can be used as part of an orthopedic implant. The orthopedic implants can include a bone interface member having a bone contact surface. In some embodiments a water swellable, water permeable interpenetrating polymer network (IPN) or semi-IPN member is provided having a bearing surface and an attachment zone. The attachment zone can be attached to the bone interface member. The water swellable, water permeable IPN or semi-IPN member can optionally including a compositional gradient between the bearing surface and the attachment zone.

The bone interface member can be made out of a metal. In some examples the metal is a porous metal. In some embodiments the bone interface member is made out of a ceramic or a polymer.

In some examples, at least a portion of the orthopedic implant is configured to change a shape during implant placement in a joint. In some examples, at least a portion of the implant is configured to transiently deform during implant placement in a joint.

The implant can have a shape selected from the group consisting of: a cap, a cup, a plug, a mushroom, a cylinder, a patch, and a stem. The implant can also be adapted to fit an acromioclavicular joint, an ankle joint, a condyle, an elbow joint, a hand joint including a metacarpal joint, a finger joint, a thumb joint, a base of thumb joint, a glenoid, a hip joint including an acetabidar joint, an intervertebral disc, a vertebral joint, including an intervertebral facet joint, a labrum, a meniscus, a foot joint, including a metatarsal joint and a toe joint, a patella, a tibial plateau, a jaw joint including a temporomandibular joint, a knee joint including a knee medial compartment joint, a patellofemoral joint, and a total knee joint, a knee meniscus, a shoulder joint including a labral joint, or a wrist joint and any portion thereof.

The IPN composition can be attached to the implant using an adhesive, such as bone cement. For example, an attachment of the attachment zone to the bone interface member can be created by an adhesive.

In some embodiments the IPN composition can include a lubricious surface or side. In one example the bearing surface can be the lubricious surface. The lubricious surface can have a coefficient of friction of less than about 0.1. The bearing surface can have a coefficient of friction of less than about 0.05. The lubricious surface can have a coefficient of friction of less than about 0.010. The lubricious surface can have a coefficient of friction of less than about 0.005. The lubricious surface can have a coefficient of friction of less than about 0.003. The lubricious surface can have a coefficient of friction of less than about 0.001. In some embodiments the lubricious surface can have a coefficient of friction of about 0.001 to about 0.1.

The IPN can have incorporated either chemically or physically within its bulk or its surface certain additives such as antioxidants (e.g., Vitamin C, Vitamin E, Irganox®, or santowhite powder), anti-microbial agents (e.g., antibiotics), anti-inflammatory agents (steroids). These can be chemically linked to the material by, for example, esterification of the anti-oxidant with any vinyl-group containing monomer such as methacrylate, acrylate, acrylamide, vinyl, or allyl ether.

In other applications the IPN compositions can be used in other mechanical applications such as a bearing as part of a motor, pump, or other mechanical device with moving parts.

FIG. 1A is a schematic illustration of cartilage 100. Cartilage has a strong collagen network 102, negatively charged proteoglycans 104, and water 106. The enlarged portion of FIG. 1A shows the negatively charged proteoglycans 104 with negatively charged molecules 108.

Figure 1B:
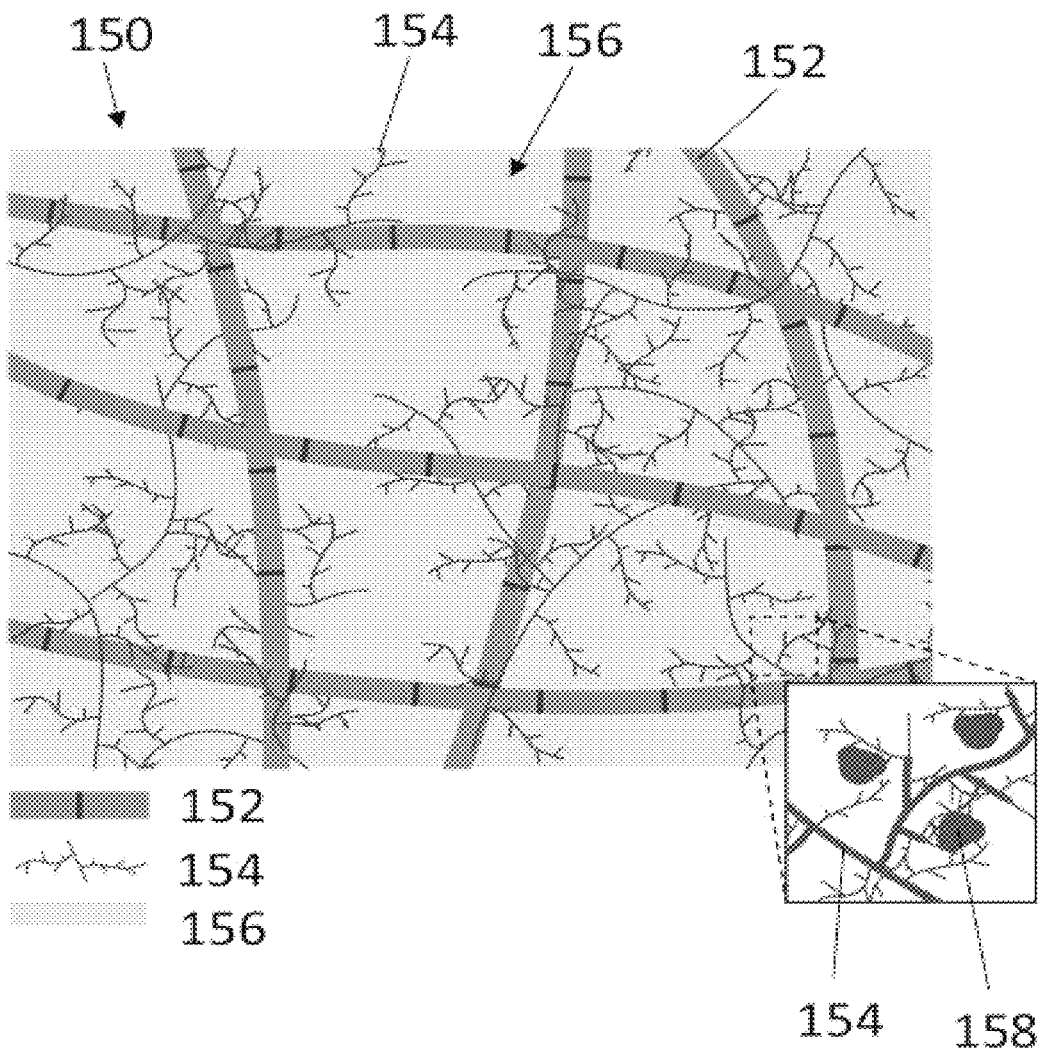
FIG. 1B is a schematic illustration of an IPN composition according to some embodiments.

FIG. 1B is a schematic illustration of an IPN composition 150 according to some embodiments. The illustrated IPN composition 150 includes a first polymer network of polymer A 152, a second network of polymer B with a negative charge 154, and water 156. FIG. 1B shows the second network of polymer B 154 with negatively charged molecules 158.

Figure 2:
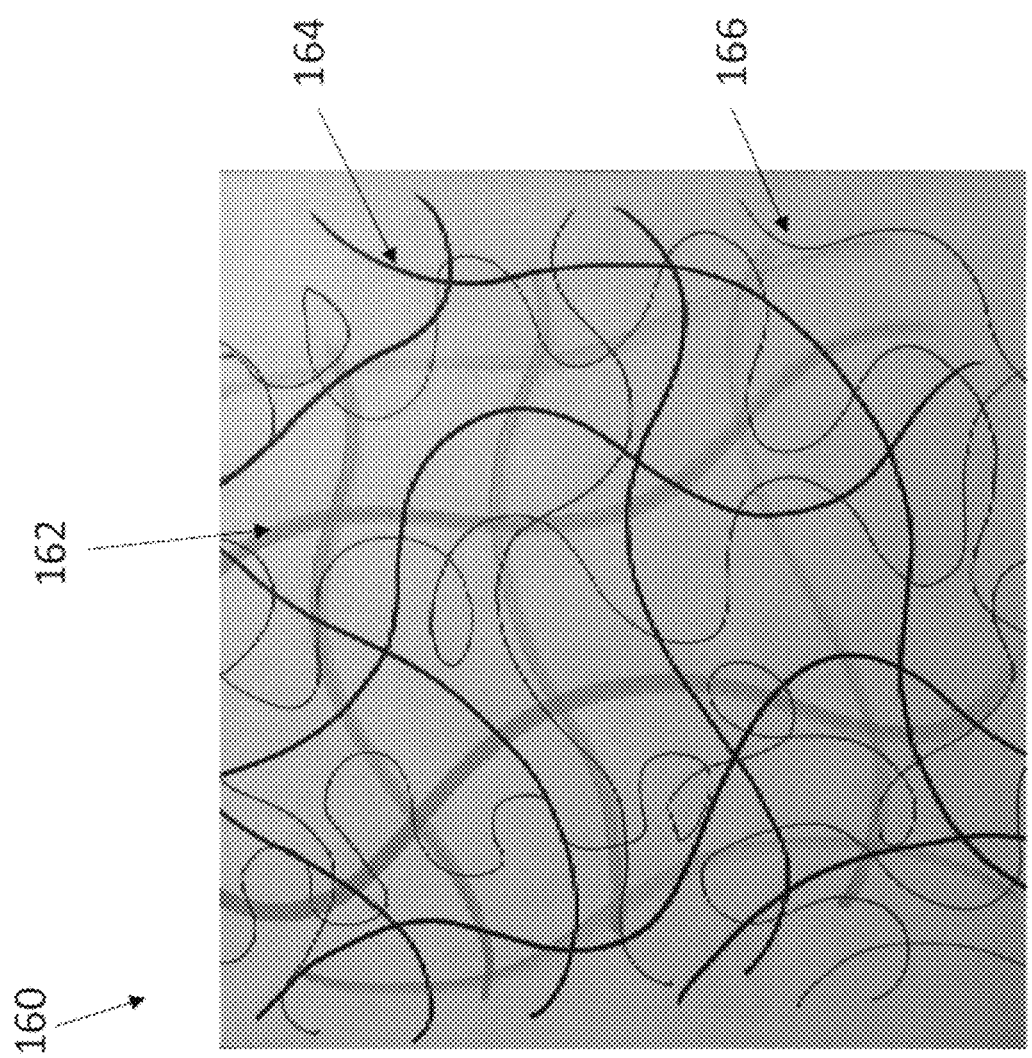
FIG. 2 is a schematic illustration of the IPN compositions described herein in accordance with some embodiments.
Figure 6:
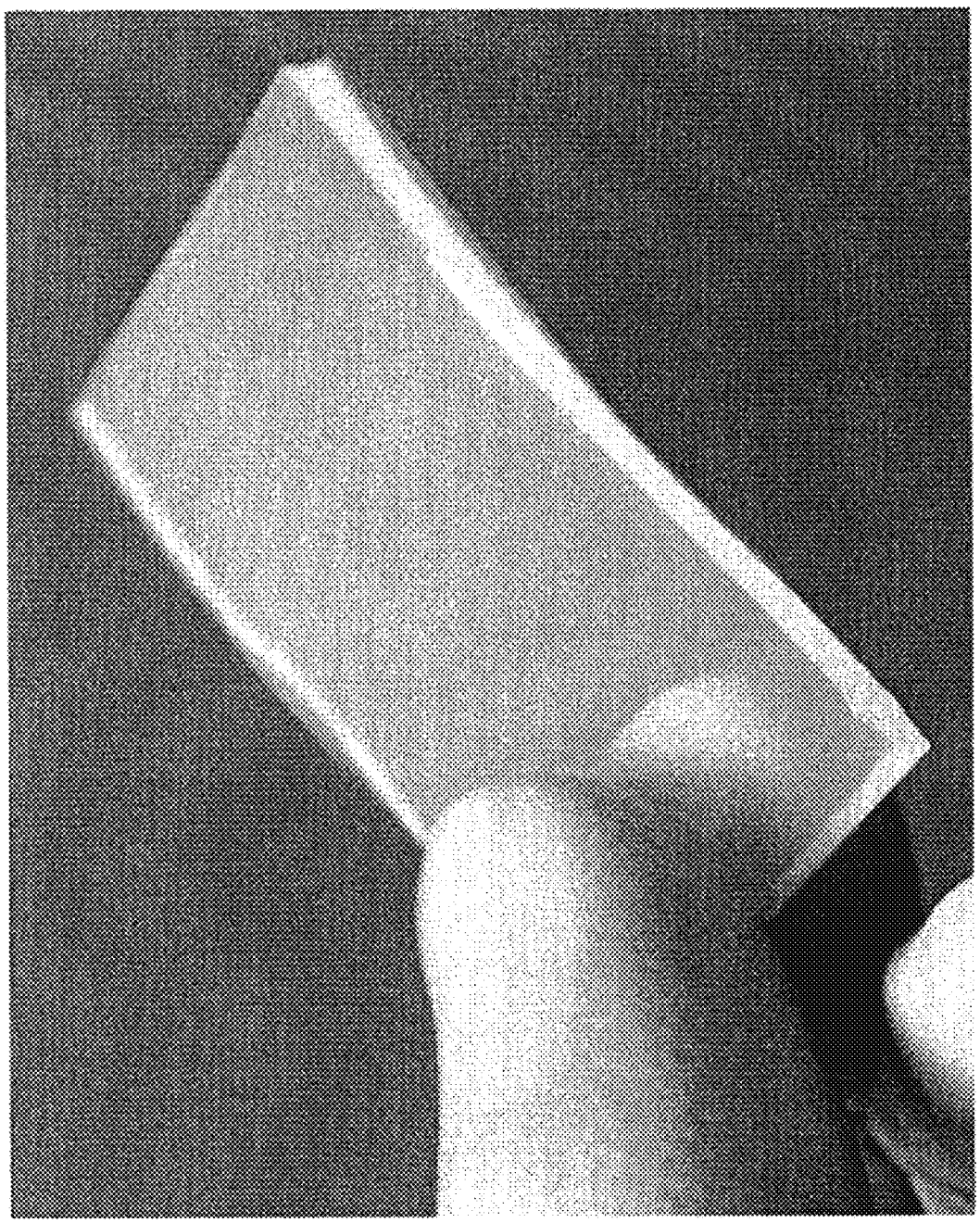
FIG. 6 is a picture of an IPN composition according to some embodiments.

FIG. 2 is a schematic illustration of the IPN compositions 160 described herein in accordance with some embodiments. The IPN composition 160 includes a first polymer network 162 that is non-ionic, a second network 164 that can be non-ionic or partially-ionic, and a third polymer network 166 that can be ionic and can contain sulfonic acid functional groups. FIG. 6 is a picture of an IPN composition according to some embodiments.

Figure 3A:
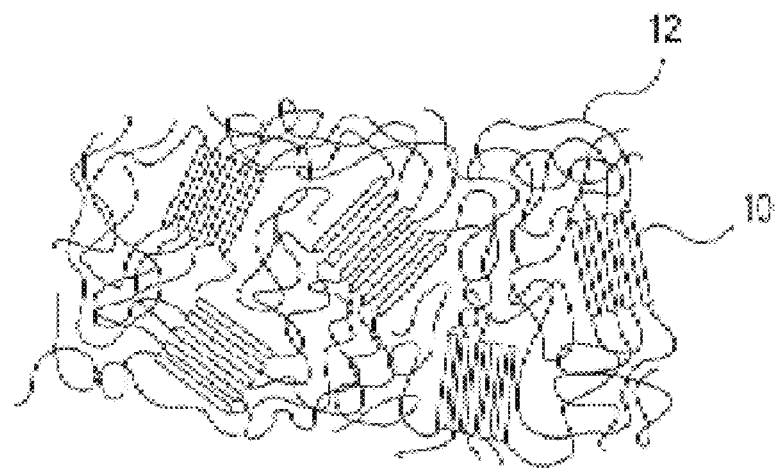
FIGS. 3A-3E illustrate a process for forming an IPN composition in accordance with some embodiments.
Figure 3B:
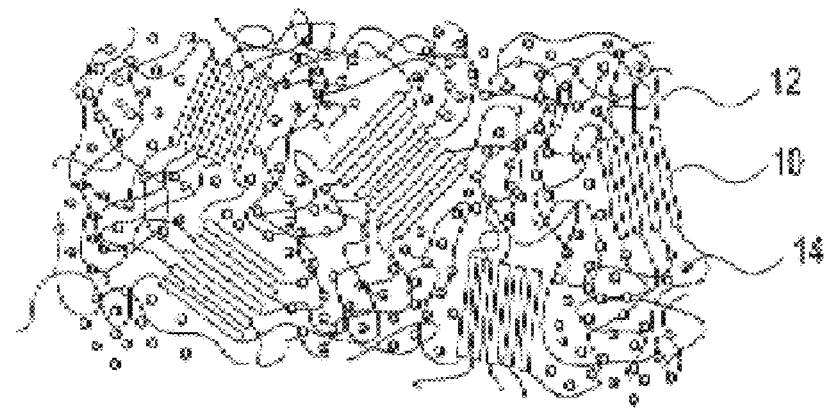
Figure 3C:
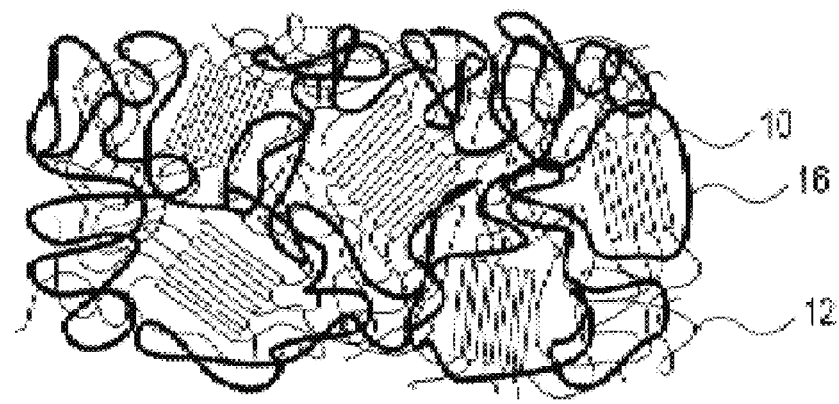
Figure 3D:
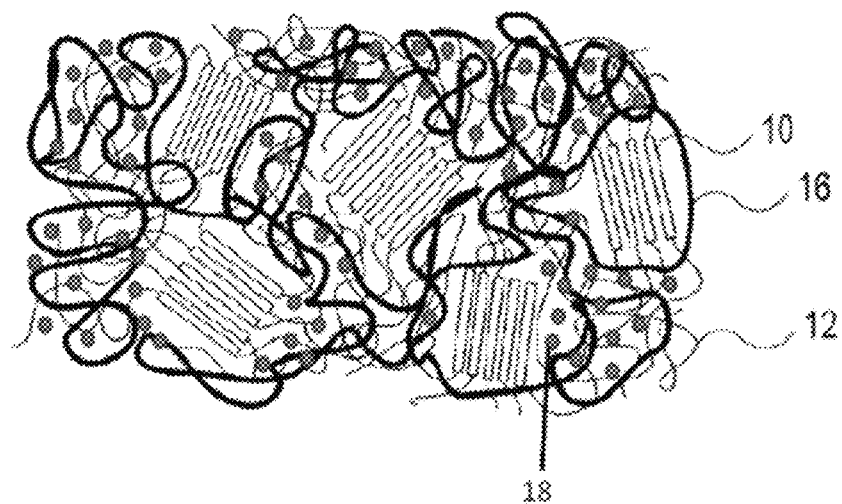

FIGS. 3A-3E illustrate a process for forming an IPN composition in accordance with some embodiments. FIGS. 3A-3E illustrate the process with respect to a hydrophobic thermoset or thermoplastic polymer, such as a thermoplastic polyurethane-based polymer, containing a network of hard segments 10 (shown as open rectangles) and soft segments 12 (shown as lines). In FIG. 3B, the soft segments 12 are swollen with non-ionic monomer 14 (shown as circles) and optional solvent, along with an initiator and cross-linker (not shown), while mostly not affecting the hard segment material 10. This swelling process is not dissolution of the polymer; the hard segments act as physical crosslinks to hold the material together as the soft segments are imbibed with the monomer(s) and optional solvent(s). After polymerization and cross-linking of the monomers, a second network 16 (shown as dark lines in FIGS. 3C and 3D) is formed in the presence of the first network to create an IPN in which the second polymer (i.e., the polymerized monomer) is primarily sequestered within the soft, amorphous domain of the first polymer. Despite some degree of molecular rearrangement and further phase separation, the hard segments largely remain ordered and crystalline, providing structure and strength to the material.

Figure 3E:
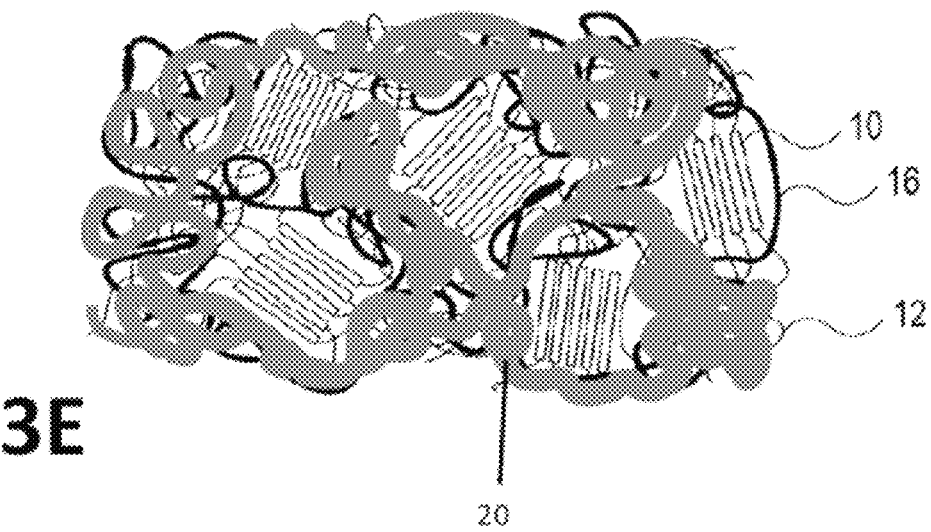

A third polymer network can then be formed by polymerizing an ionic polymer containing sulfonic acid functional groups. The second polymer network 16 can improve the compatibility of the ionic polymer containing sulfonic acid functional groups with the hydrophobic thermoset or thermoplastic polymer. For example, in FIG. 3D, the soft segments 12 are swollen with the ionic monomer including the sulfonic acid functional groups 18 (shown as circles) and optional solvent, along with an initiator and cross-linker (not shown), while mostly not affecting the hard segment material 10. This swelling process is not dissolution of the polymer; the hard segments 10 act as physical crosslinks to hold the material together as the soft segments 12 are imbibed with the monomer(s) and optional solvent(s). After polymerization and cross-linking of the monomers, a third network 20 including the sulfonic acid functional groups is formed in the presence of the first network to create an IPN in which the third polymer network (i.e., the polymerized ionic monomer) is primarily sequestered within the soft, amorphous domain of the first polymer as shown in FIG. 3E. Despite some degree of molecular rearrangement and further phase separation, the hard segments largely remain ordered and crystalline, providing structure and strength to the material.

Figure 3F:
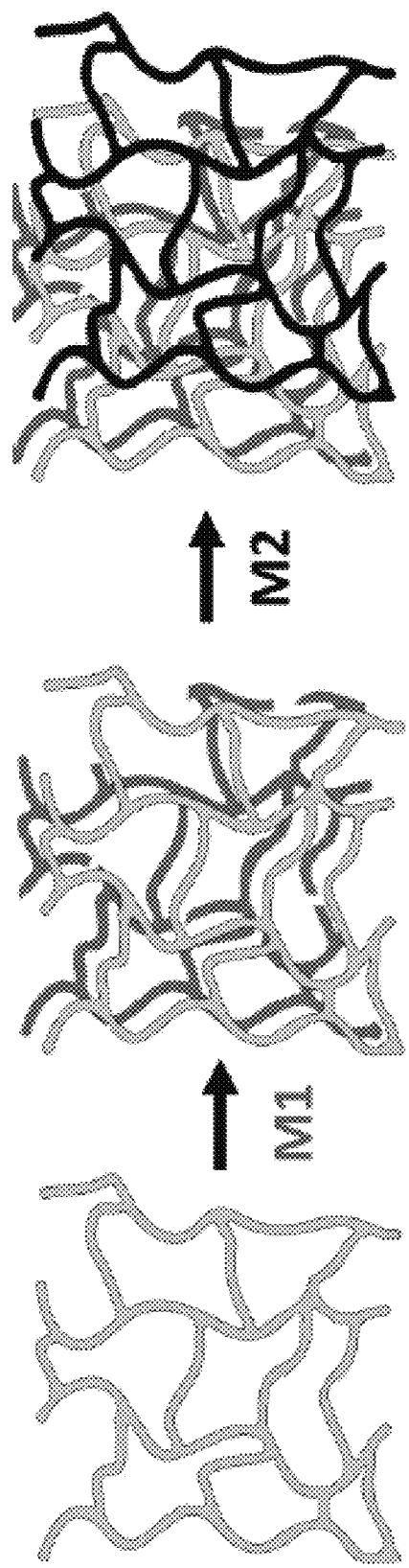
FIG. 3F is a schematic illustration of a process of forming an IPN composition in accordance with some embodiments.

FIG. 3F shows a schematic of a triple network synthesis process. A first network of PEU swollen with a monomer (or mixture of monomers) M1 is first polymerized and crosslinked to form a homopolymer or copolymer network that includes M1. The resulting two-network IPN is then further swollen with a monomer or mixture of monomers M2 that are polymerized and crosslinked to form a third network that includes M2. The M1-based polymer network is used as a compatibilizing network to enable the M2-based polymer to co-exist in an IPN with the PEU network. In some embodiments, M1 can be an acrylamide monomer, such as NVP (or a mixture of NVP and AMPS) or DMAA (or a mixture of DMAA and AMPS). Acrylamide polymers, such as NVP or DMAA can advantageously enable additional interpenetration of the PEU with PAMPS homopolymers or other sulfonated polymers. The increased concentration of PAMPS in the IPN when using NVP or DMAA may occur as a result of template polymerization, i.e., non-covalent interactions, between the acrylamide polymer (NVP or DMAA) and the AMPS.

Figure 4A:
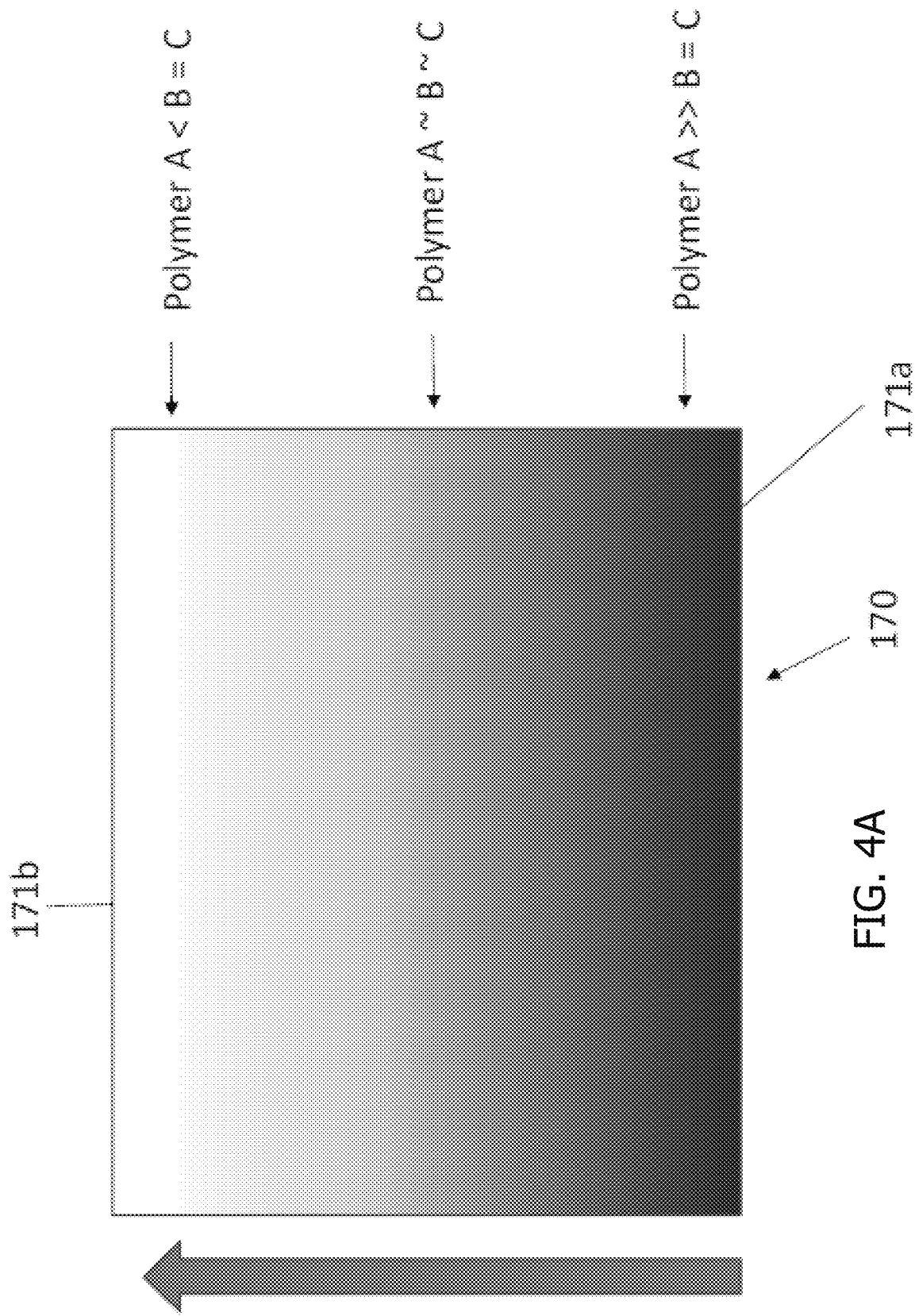
FIGS. 4A and 4B are schematic illustrations of an IPN composition in accordance with some embodiments.

FIG. 4A is a schematic illustration of an IPN composition 170 in accordance with some embodiments. The IPN composition 170 includes a triple polymer network with a hydration gradient between a stiffer surface 171a and a lubricious surface 171b. FIG. 4A shows the hydration gradient as a smooth gradient with a compositional transition. The hydration level decreases with increasing distance from the lubricious surface 171b. The hydration level is at a maximum at the lubricious surface 171b. The lubricious surface includes polymer A, polymer B, and polymer C with a greater amount of polymers B and C relative to polymer A. A region between the stiffer surface 171a and lubricious surface 171b includes around the same amounts of polymers A, B, and C in the illustrated example. The stiffer surface 171a includes a greater amount of polymer A relative to polymers B and C. The amount of polymers B and C can be relatively the same adjacent to the stiffer surface 171a. In one example polymer A can be polyurethane, polymer B can be a polymer of HEMA, NVP and/or DMAA, and polymer C can be poly-AMPS.

Figure 4B:
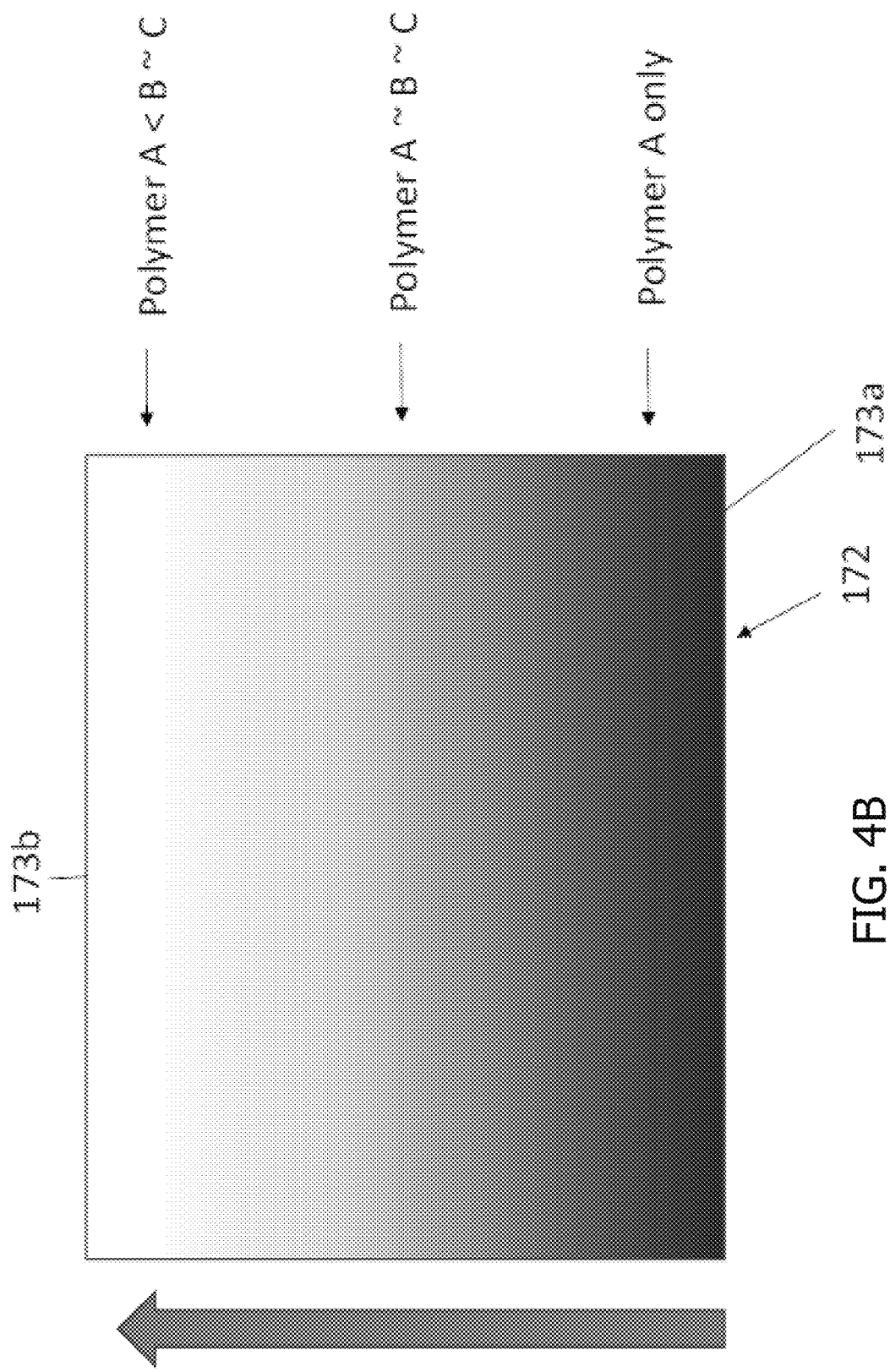

FIG. 4B is a schematic illustration of an IPN composition 172 in accordance with some embodiments. The IPN composition 172 includes a triple polymer network with a hydration gradient between a stiffer surface 173a and a lubricious surface 173b. FIG. 4B shows the hydration gradient as a smooth gradient with a compositional transition. The hydration level decreases with increasing distance from the lubricious surface 173b. The hydration level is at a maximum at the lubricious surface 173b. The lubricious surface includes polymer A, polymer B, and polymer C with a greater amount of polymers B and C relative to polymer A. A region between the stiffer surface 173a and lubricious surface 173b includes around the same amounts of polymers A, B, and C in the illustrated example. The stiffer surface 173a includes polymer A only in FIG. 4B. In one example polymer A can be polyurethane, polymer B can be a polymer of HEMA, NVP and/or DMAA, and polymer C can be poly-AMPS.

FIGS. 4A-4B are illustrated with a continuous hydration gradient and a compositional gradient. In other embodiments the hydration gradient can be a two-way gradient where the core of the material includes the hydrophobic/pure polymer A and the outer surfaces of the material are hydrated and include polymers A, B, and C. Additional gradients can also be formed in the IPN compositions illustrated in FIGS. 4A and 4B. In one example an adhesive gradient can be formed at the stiffer surface 171a/173c.

The IPN compositions can be designed to mimic cartilage on a lubricious side along with an opposing side that has properties that are similar to bone. The properties of the IPN composition can transition gradually between the cartilage-like side and the bone-like side.

Figure 7A:
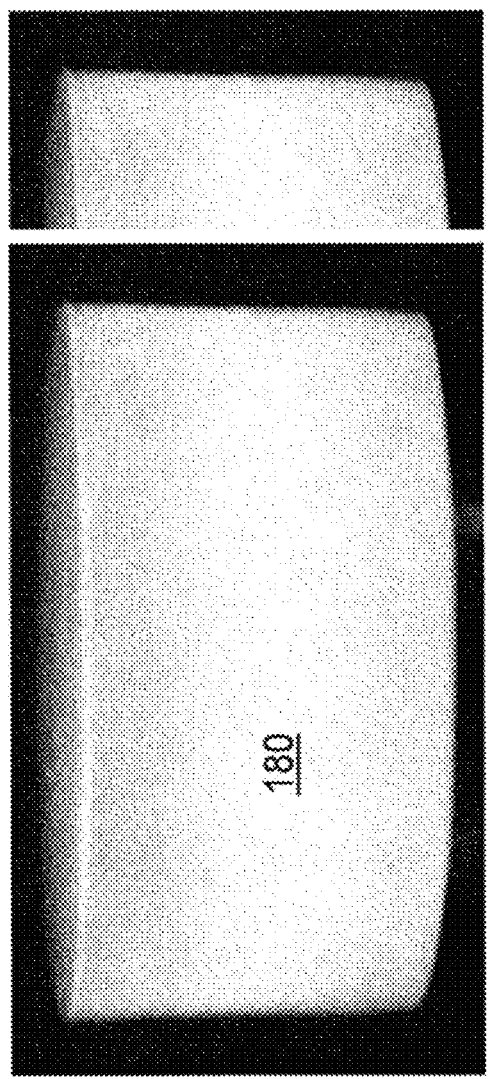
FIG. 7A is a picture of an IPN composition with a gradient in accordance with some embodiments.
Figure 7B:
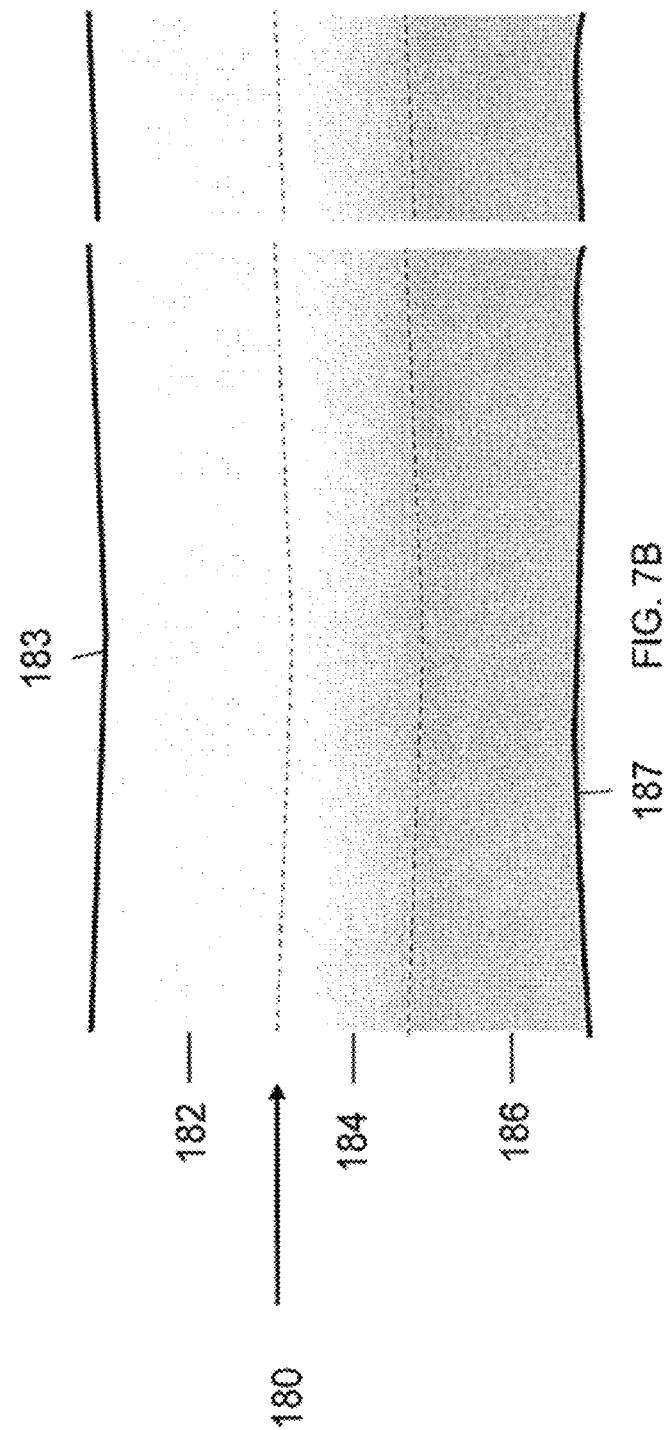
FIG. 7B is a schematic illustration of the IPN composition with a gradient in accordance with some embodiments.

FIG. 7A is a picture of an IPN composition 180 with a gradient in accordance with some embodiments. FIG. 7B is a schematic illustration of the IPN composition 180 with a gradient in accordance with some embodiments. As shown in FIG. 7B the cartilage-like side 182 represents a hydrated, lubricious, and compliant bearing surface 183. The bone-like side 186 represents a stiffer anchoring surface 187. Between the cartilage-like and bone-like surfaces is a gradient transition zone 184 without an interface region (e.g. no graft region).

Figure 8:
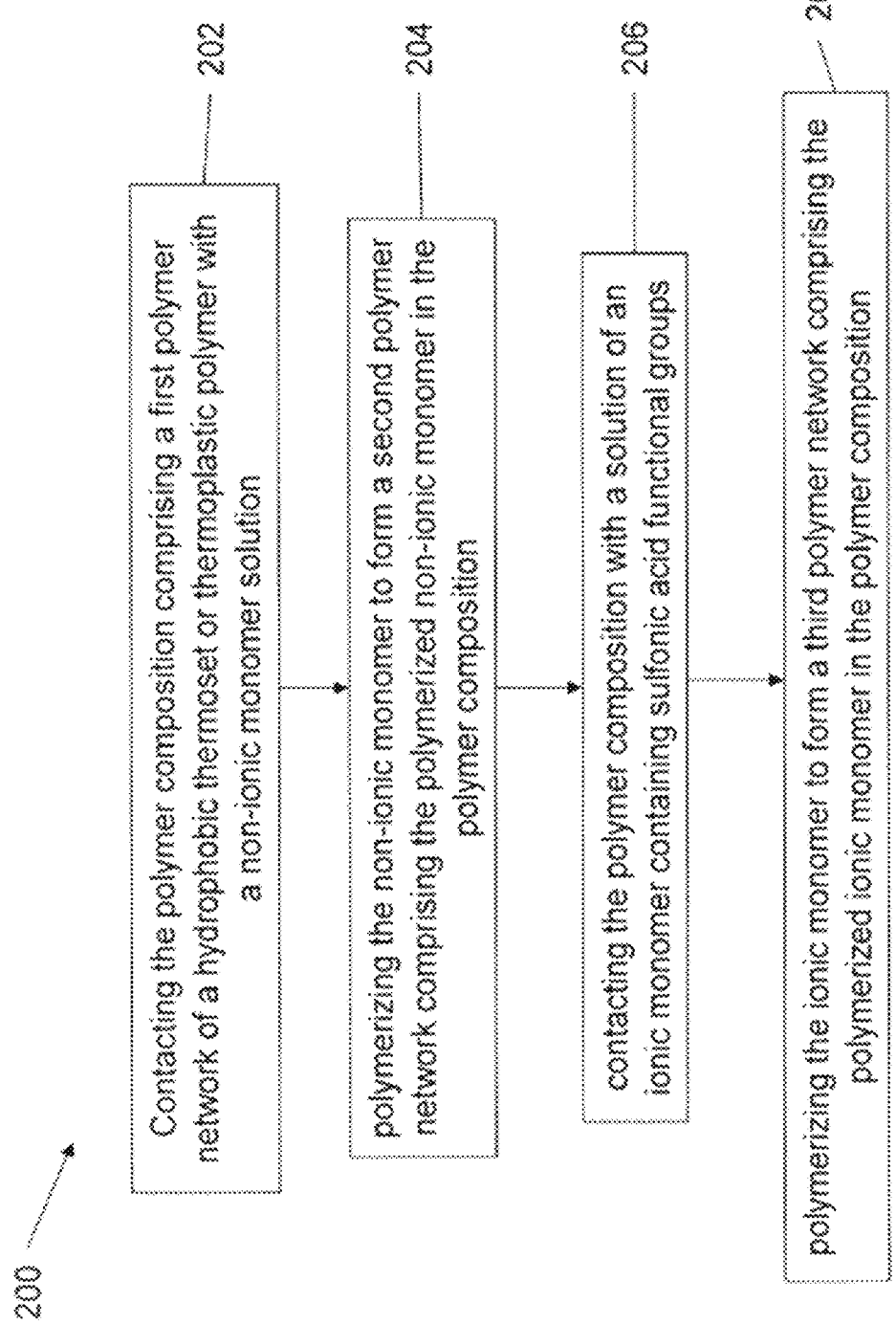
FIG. 8 illustrates a flow chart detailing embodiments of methods for making the IPN compositions described herein.

Methods for making the IPN compositions disclosed herein are also provided. FIG. 8 illustrates a method 200 for forming an IPN composition in accordance with some embodiments. A first step 202 includes contacting the polymer composition comprising a first polymer network of a hydrophobic thermoset or thermoplastic polymer with a non-ionic monomer solution. A second step 204 includes polymerizing the non-ionic monomer to form a second polymer network comprising the polymerized non-ionic monomer in the polymer composition. A third step 206 includes contacting the polymer composition with a solution of an ionic monomer containing sulfonic acid functional groups. A fourth step 208 includes polymerizing the ionic monomer to form a third polymer network comprising the polymerized ionic monomer in the polymer composition.

In some embodiments the first polymer network comprises polyurethane. Examples of the non-ionic monomer include monomers that include one or more of: dimethylacrylamide, acrylamide, N-isopropyl acrylamide (NI-PAAm), hydroxyethyl acrylate, hydroxyethyl methacrylate, vinyl alcohol, methyl acrylate, hydroxyethyl acrylamide, hydroxyethyl methacrylamide, and combinations thereof. Examples of the ionic monomer containing sulfonic acid groups include monomers that include one or more of: 2-acrylamido 2-methyl propane sulfonic acid (AMPS), 2-Propene-1-sulfonic acid, 2-Methyl-2-propene-1-sulfonic acid, 1,3-Propanesulfone, 1,4 butane sulfone, vinyl sulfonic acid, anetholesulfonic acid, and styrenesulfonic acid.

In some embodiments the non-ionic monomer comprises hydroxyethyl methacrylate and the ionic monomer containing sulfonic acid groups comprises polymerized 2-acrylamido 2-methyl propane sulfonic acid (AMPS).

In some embodiments any of the first polymer network, second polymer network, and third polymer network can be formed from multiple monomers to form a co-polymer. For example, the third polymer network can be formed by polymerizing 2-acrylamido 2-methyl propane sulfonic acid (AMPS) and acrylic acid to form a co-polymer.

The non-ionic monomer can be provided in a solution with a water based solvent. In some embodiments the concentration of the non-ionic monomer, such as HEMA (2-hydroxyethyl methacrylate) or HEMAAm (2-hydroxyethyl methacrylamide), can be up to about 40% by weight.

In some embodiments, the concentration of HEMA can be as high as 100%. Additional ionic monomers, such as acrylic acid can also be added to the non-ionic monomer solution. In some embodiments acrylic acid is provided in the non-ionic monomer solution with at a concentration of about 1% to about 50% by weight. In some embodiments acrylic acid is provided in the non-ionic monomer solution with at a concentration of about 1% to about 75% by weight.

The methods can include using a cross-linking agent and/or an initiator (thermal, chemical or photo-initiator) to form cross-links. A photo-initiator can be provided with the non-ionic monomer to crosslink the second polymer network. A photo-initiator can be provided with the ionic monomer to crosslink the third polymer network.

In some embodiments the methods can include forming a compositional gradient between a first surface of the IPN composition and a second surface of the IPN composition. The compositional gradient can form a stiffness gradient. The composition gradient can include an adhesive gradient. The compositional gradient can form a hydration gradient. For example, the hydration gradient can be formed in one of the second or third polymer networks.

The methods include optionally molding, shaping, or forming the polymer composition to a desired shape. In some embodiments the desired shape is selected from the group consisting of: a cap, a cup, a plug, a mushroom, a cylinder, a patch, and a stem. In some embodiments the desired shape is adapted to fit an acromioclavicular joint, an ankle joint, a condyle, an elbow joint, a hand joint including a metacarpal joint, a finger joint, a thumb joint, a base of thumb joint, a glenoid, a hip joint including an acetabular joint, an intervertebral disc, a vertebral joint, including an intervertebral facet joint, a labrum, a meniscus, a foot joint, including a metatarsal joint and a toe joint, a patella, a tibial plateau, a jaw joint including a temporomandibular joint, a knee joint including a knee medial compartment joint, a patellofemoral joint, and a total knee joint, a knee meniscus, a shoulder joint including a labral joint, or a wrist joint and any portion thereof. Bone cement can be used to secure the IPN composition to a prosthesis, bone interface member, or other desired attachment surface.

In one embodiment, a polyurethane is soaked in a monomer solution containing a non-ionic monomer along with a crosslinking agent, and then a non-ionic network is formed within the polyurethane network to form a two-network IPN. This IPN is then soaked in the monomer solution of 2-acrylamido 2-methyl propane sulfonic acid (AMPS) along with a crosslinking agent, and then a poly-AMPS (PAMPS) network is formed within the pre-existing IPN, to form effectively a three-network IPN of polyurethane (first network), a non-ionic polymer (second network), and PAMPS (third network). In other embodiments, copolymers incorporating other monomers including acrylic acid and other ethylenically unsaturated monomers (both ionic and non-ionic) can be incorporated into the second or third polymer networks. Additional networks can be formed, such as quadruple or higher order networks using these combinations. In another embodiment, sulfonic acid can be incorporated into the first polymer network as well, such as a sulfonated polyurethane network. Any number of crosslinking agents and initiators (e.g. photoinitiators and chemical initiators) can be used to polymerize the networks. Monomers other than AMPS that contain sulfonic acid functional groups may be used in any of the networks, including the third polymer network of the aforementioned three-network systems, for example 2-Propene-1-sulfonic acid, 2-Methyl-2-propene-1-sulfonic acid, 1,3-Propanesulfone, 1,4 butane sulfone, vinyl sulfonic acid, anetholesulfonic acid, and styrenesulfonic acid.

Non-ionizable (charge neutral) monomers that can be used include but are not limited to dimethylacrylamide, acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide and any combinations and/or derivatives of these monomers. Any number or combinations of ethylenically unsaturated monomers or macromonomers (i.e. with reactive double bonds or vinyl groups) with various functional groups can be used alone or in combination with various solvents (e.g. water or organic solvents or mixtures thereof) in either the second or third polymer networks. The ethylenically unsaturated aspect of these includes acrylic, methacrylic, acrylamide, allyl ether, and other similar monomers. Optionally, either the second or third polymer networks can be mixtures of non-ionizable and ionizable monomers. For instance, the second network can be a mixture of two or more non-ionizable monomers, or be a mixture of one or more ionizable monomer and one or more non-ionizable monomer. The third polymer network can be a mixture of two or more non-ionizable monomers, or be a mixture of one or more ionizable monomer and one or more non-ionizable monomer. The same can apply to additional networks (fourth, fifth, etc. ... ) networks that are formed. The triple or higher order IPNs formed in these examples can be synthesized as gradient IPNs (or gradient polymer alloys) by altering the relative amount of said second and/or third polymer network monomer solutions within the first polymer network prior to or during the polymerization step of the second, third, or higher order network.

Any number of crosslinking agents and initiators (e.g. photoinitiators and chemical initiators) can be used to polymerize the networks described herein. Any type of compatible cross-linkers may be used to crosslink the second and third networks in the presence of any of the aforementioned first networks such as, for example, ethylene glycol dimethacrylate, ethylene glycol diacrylate, diethylene glycol dimethacrylate (or diacrylate), triethylene glycol dimethacrylate (or diacrylate), tetraethylene glycol dimethacrylate (or diacrylate), polyethylene glycol dimethacrylate, or polyethylene glycol diacrylate, methylene bisacrylamide, N,N'-(1,2-dihydroxyethylene) bisacrylamide, derivatives, or combinations thereof. Examples of crosslinking agents include triethylene glycol dimethacrylate or N,N methylene bisacrylamide Any number of photoinitiators can also be used depending on their solubility with the precursor solutions/materials. These include, but are not limited to, 2-hydroxy-2-methyl-propiophenone and 2-hydroxy-1-[4-(2-hydroxyethoxy) phenyl]-2-methyl-1-propanone. Other, naturally occurring photoinitiators can be used such as riboflavin (Vitamin B2), or rose Bengal. In addition, other initiators such as benzoyl peroxide, 2-oxoglutaric acid, azobisisobutyronitrile, or potassium persulfate (or sodium persulfate) can be used. For instance, benzoyl peroxide is useful for temperature-initiated polymerizations, while azobisisobutyronitrile and sodium persulfate are useful as radical initiators.

Examples of sulfonate-containing monomers include but are not limited to acrylamide methyl propane sulfonic acid (AMPS), 2-Propene-1-sulfonic acid, 1,3-Propanesulfone, 1,4 butane sulfone, anetholesulfonic acid, styrenesulfonic acid, vinyl sulfonic acid, 3-sulfopropyl acrylate, 3-sulfopropyl methacrylate, 2-methyl-2-propene-1-sulfonic acid, or any monomers in which sulfonic acid is conjugated (allyl ethers, acrylates, methacrylates, vinyl groups, or acrylamides). The pendant functional groups on polymers resulting from these monomers and monomer combinations can be subject to subsequent chemical reactions to yield other functionalities to the final IPN. For instance, functional groups can be modified to form chemical links to an anti-oxidant, such as Vitamin C or Vitamin E. In other embodiments, anti-oxidants such as Vitamin E or Vitamin C can be added to the triple network IPN after its complete formation, through a doping process. Vitamin E in particular, given its hydrophobicity, would sequester within the solid phase (polyurethane hard segments) and thus would be furnished as a depot or reservoir of Vitamin E that would have long residence time within the implant and, in turn, body, to protect against oxidation. Either Vitamin E or C could be covalently bound within the IPN as well, after its complete formation.

In another embodiment, a hydrophilic-hydrophobic IPN as presented in US2013/0138210, which contains carboxylate ionic groups can be sulfonated by means of amidation using an amine containing sulfonic acid (or amino acid). In this case, a peptide bond is formed between carboxylates of the IPN and the amine in the sulfonic acid.

Applications of the present disclosure include but are not limited to orthopedic implants such as cartilage replacement devices, joint replacement devices, meniscal replacements, interpositional spaces, tendon or ligament replacement or augmentation, cartilage scaffolds, cartilage replacement plugs, cartilage stimulation plugs, bone filler implants to stimulate cartilage regeneration, and facet or vertebral disc implants. Joints that can be addressed with this technology include but are not limited to the knee, foot, toe, ankle, hip, shoulder, fingers, thumb, hand, wrist, jaw, intervertebral space, facet, elbow, and lumbar/thoracic/cervical discs. Other medical devices that may benefit from the present disclosure include urinary catheters, cardiovascular implants including stents, catheters, cerebral shunts, and cerebral coils, Left Ventricular Assist Device (LVAD) bearings, and condoms.

FIGS. 9A-9D are illustrations of examples of the IPN compositions described herein used as a cartilage patch in a knee, as a hip total cartilage replacement, and in a partial knee cartilage replacement procedures, respectively, in accordance with some embodiments. The IPN compositions can be molded or formed in the desired shapes for the targeted application and affixed with adhesive bone cement. Examples of adhesive bone cements that can be used include those disclosed in co-owned U.S. Patent Publication No. 2013-0103157. The use of polymethylmethacrylate (PMMA) based bone cements can form an additional gradient (e.g. adhesive gradient) with the IPN compositions described herein as described in U.S. Patent Publication No. 2013-0217829.

Figure 9A:
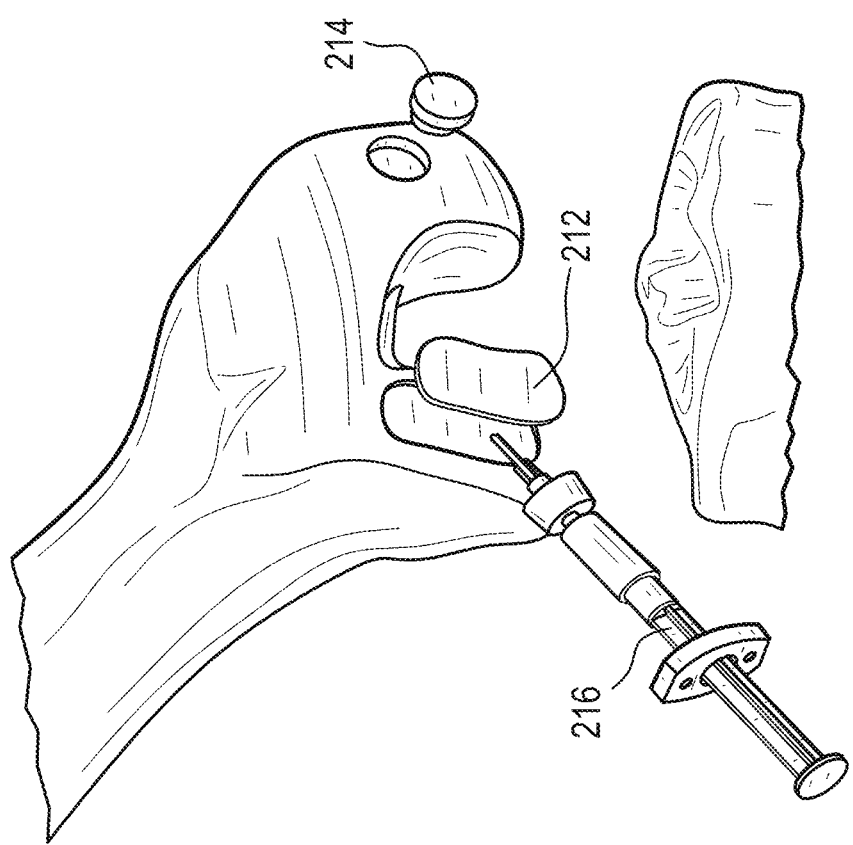
FIGS. 9A-9C are illustrations of examples of the IPN compositions described herein used as a cartilage patch in a knee, as a hip total cartilage replacement, and in a partial knee cartilage replacement procedures, respectively, in accordance with some embodiments.

FIG. 9A illustrates a cartilage patch 212 and plug 214 made out of the IPN compositions described herein. The cartilage patch 212 and plug 214 can be used to treat focal lesions in young patients and also has potential for arthroscopic applications. The cartilage patch/plug can be affixed to the bone using bone cement 216.

Figure 9B:
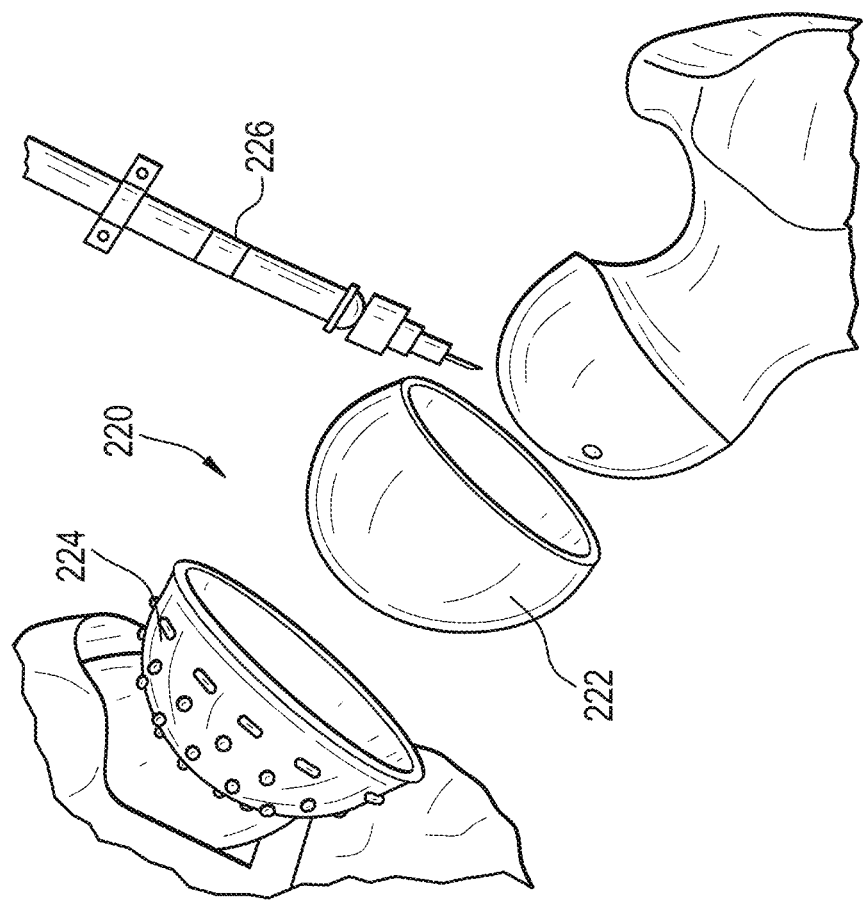
Figure 9C:
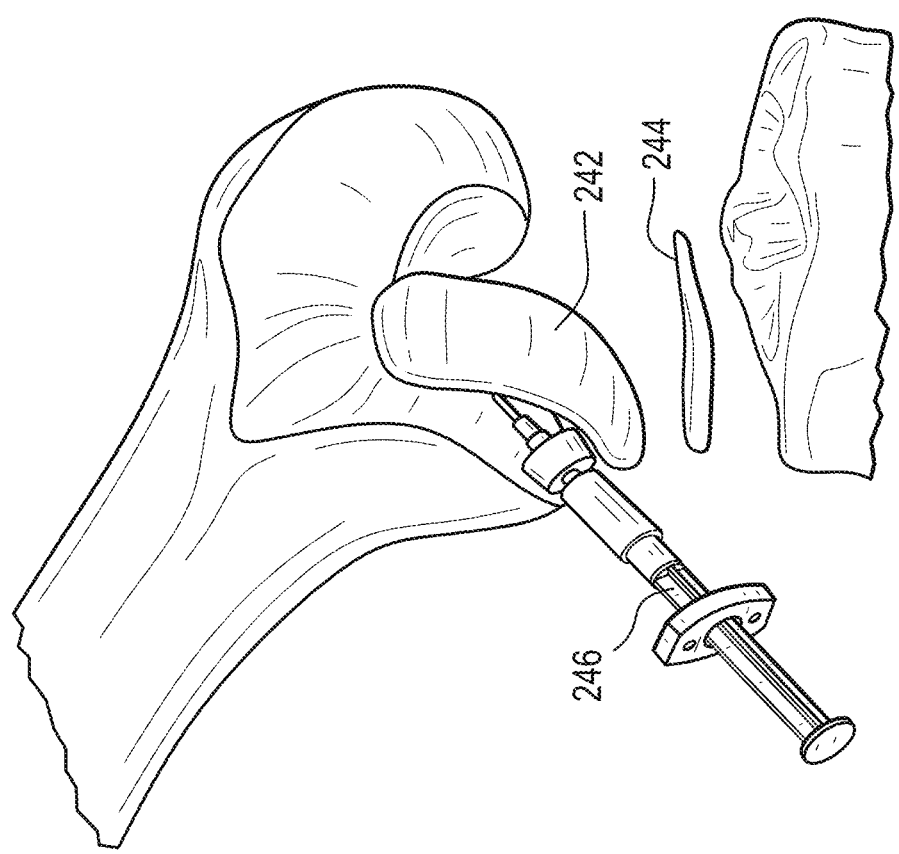

FIG. 9B illustrates a hip total cartilage replacement procedure using the IPN compositions described herein to replace the cartilage of the hip 220, specifically the femoral head 222, and acetabular cup 224. The IPN compositions can be secured in place using adhesive bone cement 226, compositions of which are described herein FIG. 9C illustrates a partial knee replacement procedure using the IPN compositions described herein. The IPN composition implants 242, 244 can be placed arthroscopically for repairing the medial, lateral, and patellofemoral joint surfaces. The implants 242, 244 can be held secured to the desired joint surface using bone cement 246.

IPN without a sulfonated network and an IPN with a sulfonated network were tested by exposure to a calcium rich environment. The sulfonated IPN and IPN without a sulfonated network were exposed to an environment having 2.5 times the amount of calcium [Ca++] typically present in a physiological environment for six months. The amount of calcium typically present in the body ranges from about 1.1-1.4 mM. The tested amount of calcium was about 3.0 mM. An average amount of calcium typically present in the body can be estimated as about 2.5 mM. The sulfonated IPN showed a resistance to binding with divalent cations, maintained a high water content, and remained lubricious after exposure to the environment containing calcium.

The wet mass change for the sulfonated IPN in environments with about 50 times (about 60 mM) the physiological level of calcium and about 2.5 times (about 3.0 mM) the physiological level of calcium were tested. The sulfonated IPN after incubation in an environment with a calcium concentration of about 50 times (about 60 mM) the physiological level of calcium exhibited a wet mass change of less than 3% as compared to the wet mass of the IPN equilibrated in physiologic ion, pH and temperature conditions. The sulfonated IPN after incubation in an environment with a calcium concentration of about 2.5 times (about 3.0 mM) the physiological level of calcium exhibited a wet mass change of less than 2% as compared to the wet mass of the IPN equilibrated in physiologic ion, pH and temperature conditions.

The tested sulfonated IPN exhibits low $Ca^{++}$ or $Mg^{++}$ affinity, as shown by the long term exposure to high $[Ca^{++}]$ solutions. The sulfonated IPN also remained extremely slippery with a coefficient of friction of=0.003 in a physiologic $[Ca^{++}]$ solution for over 6 months.

Other embodiments for the IPN compositions disclosed herein may include industrial bearing applications, such as pump bearings, stern shaft bearings, axial and radial bearings, water turbine bearings, linear bearings, linear stages and others. Other applications include industrial applications such as coatings or surfaces for marine vessels.

Figure 11:
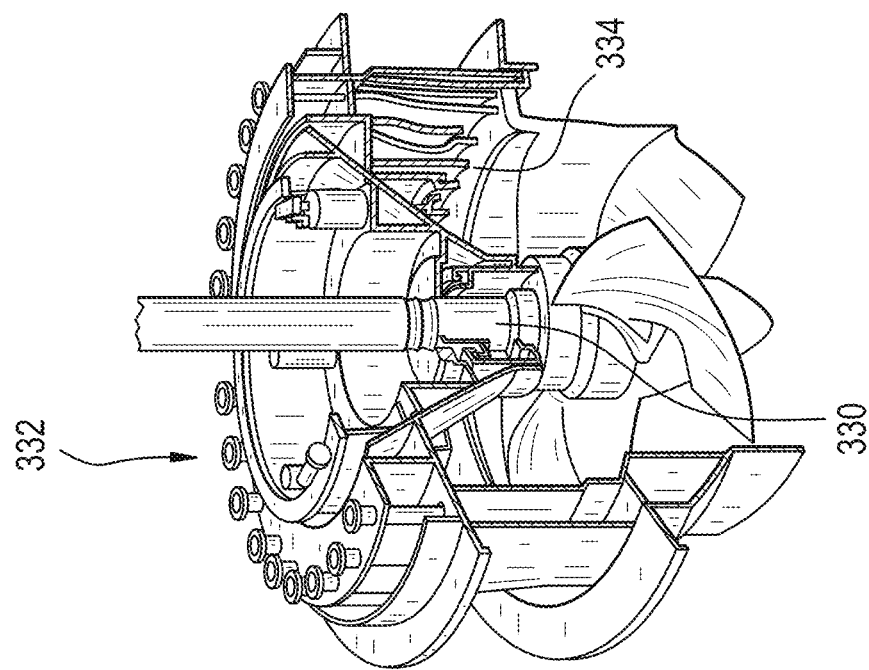
FIG. 10 and FIG. 11 illustrate the use of the IPN compositions described herein as bearings in a propeller shaft and as bearings in a hydro turbine, respectively, in accordance with some embodiments.
Figure 10:
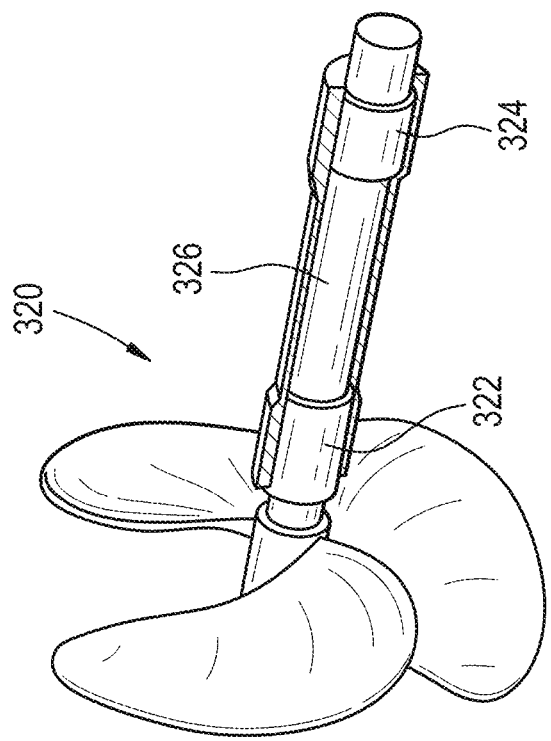

FIGS. 10 and 11 illustrate the use of the IPN compositions described herein as bearings in a propeller shaft and as bearings in a hydro turbine, respectively, in accordance with some embodiments. FIG. 10 illustrates the IPN compositions as two bearings, the aft bearing 322 and forward bearing 324, engaged with a sterntube 320 propeller shaft 326. The aft bearing 322 and forward bearing can form a saltwater seal between them. In the example illustrated in FIG. 10 the IPN composition bearings 322, 324 can be used without the need for a separate aft seal system. The sterntube bearing can serve several important purposes. The bearings can support the tailshaft and a considerable proportion of the propeller weight. The bearings can also act as a gland to prevent the entry of seawater to the machinery space. The IPN compositions described herein can function as sterntube bearings with improved properties over conventional bearings to support a portion of the sterntube propeller shaft while maintaining a seal to the seawater and also providing surfaces with a low coefficient of friction.

FIG. 11 illustrates the IPN composition used as a journal bearing 330 in a hydro turbine engine 332 that can be part of a ship engine. The hydro turbine engine 332 can move water through a portion of the engine 334. The IPN composition can provide a lubricious surface when used as a journal bearing 330 with improved properties and a less complicated design over conventional journal bearing designs.

Figure 13:
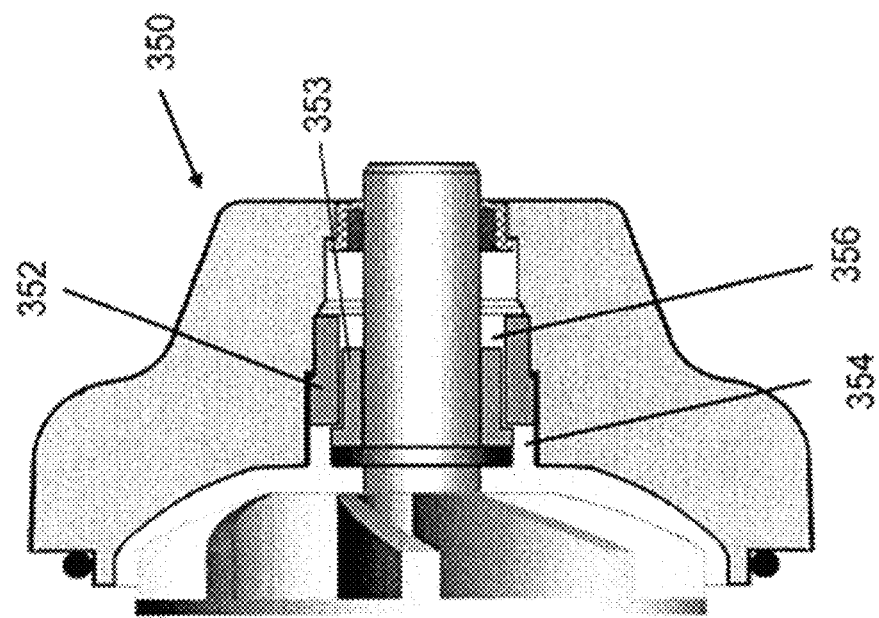
FIG. 13 illustrates an exemplary water pump using the IPN compositions described herein as bearings in accordance with some embodiments.
Figure 12:
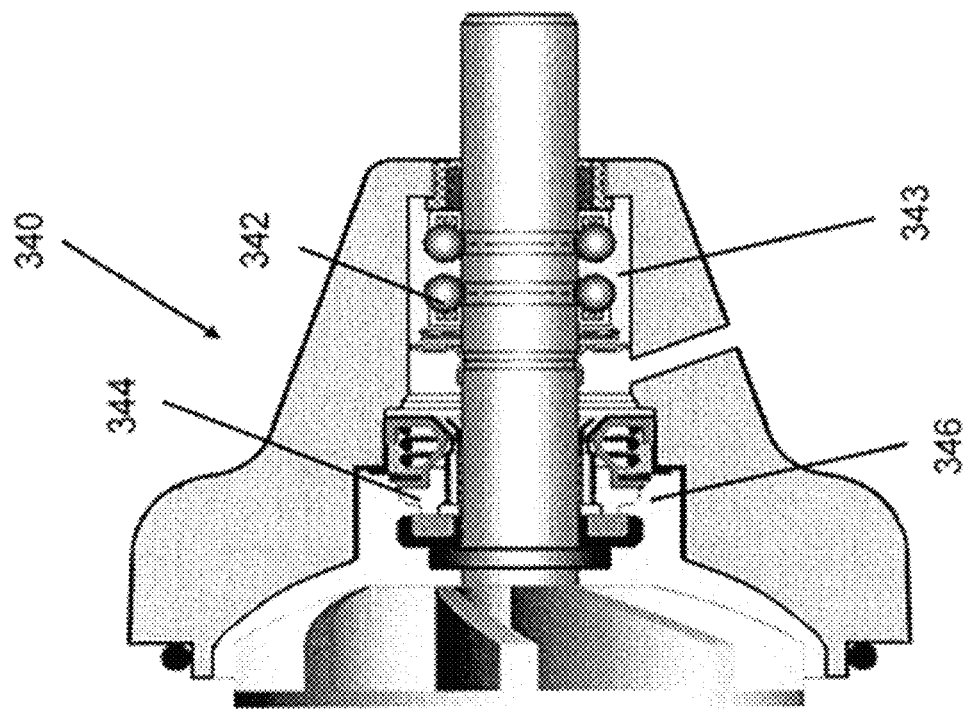
FIG. 12 illustrates a water pump with a conventional bearing system.

FIG. 12 illustrates a water pump 340 with a conventional bearing system 342 that requires a complex water seal system 344 and water wetted chamber 346 to separate the bearing system from the water. The water pump 340 bearing system 342 uses a complex oil wetted chamber 343. FIG. 13 illustrates an exemplary water pump 350 using the IPN compositions described herein as bearings 352, 353 in accordance with some embodiments. The IPN composition based bearings 352, 353 can be used in a simpler water pump design such that the IPN composition based bearing can be used in direct contact with water such that wetted water chambers 354, 356 can replace the complex water seal system and the complex bearing system in conventional water pumps.

The IPN compositions described herein can provide many different benefits over conventional bearings. In one aspect the IPN compositions can exhibit a great amount of corrosion resistance over conventional bearings. In another aspect the IPN compositions can exhibit a high corrosion resistance against seawater, fresh water, and mild chemicals. In yet another aspect the IPN compositions can exhibit a low coefficient of friction and low wear. The IPN compositions are not a surface coating and can therefore exhibit lubricious and low coefficient of friction properties throughout the bulk material. The IPN compositions can exhibit a low coefficient of friction and low wear even under dynamic loads. For example, the incompressible nature of water can improve the IPN composition response to dynamic loads. The properties can be independent of velocity with low friction even at quasi static conditions. For example, the IPN compositions may not exhibit a start-up friction and work with RPM values from zero and greater. The IPN compositions do not use oil as a lubricant or require another lubricant for operation.

The IPN composition properties, such as compliance and stiffness can be tuned based on the desired response for the bearing. The compliance and stiffness of the IPN composition can allow the bearing to accommodate vibration and significant misalignments of the shaft to which the bearing is engaged based on the viscoelasticity of the IPN composition.

In some embodiments the IPN compositions have coefficient of friction on an outer surface of less than about 0.001. In some embodiments the IPN compositions can be operated as bearings with a noise of less than about 10 dB. The IPN composition can offer quieter operation than conventional bearing materials and also be produced for a much lower cost than conventional bearings.

The IPN compositions can operate under a low thermal load such that no cooling is needed. The IPN compositions can function as bearings without the use of a pump system or fluid transfer system utilizing oil or water. Thus, the bearings can be incorporated into more simple designs, without fluid transfer systems that can require complex control systems. For water based applications the IPN compositions can be additional lubricated by the contact with water, lake water, tap water, and seawater. The IPN compositions also do not require a seal for water based applications.

It is believed that the IPN compositions described herein employ boundary layer lubrication (polarity) in low pressures and interstitial fluid pressurization in higher pressures It is also believed that the IPN compositions described herein employ boundary layer lubrication (polarity) at low velocities and interstitial fluid pressurization at higher velocities. It is also believed that hydrodynamic lubrication can also be employed by the IPN composition.

Figure 14:
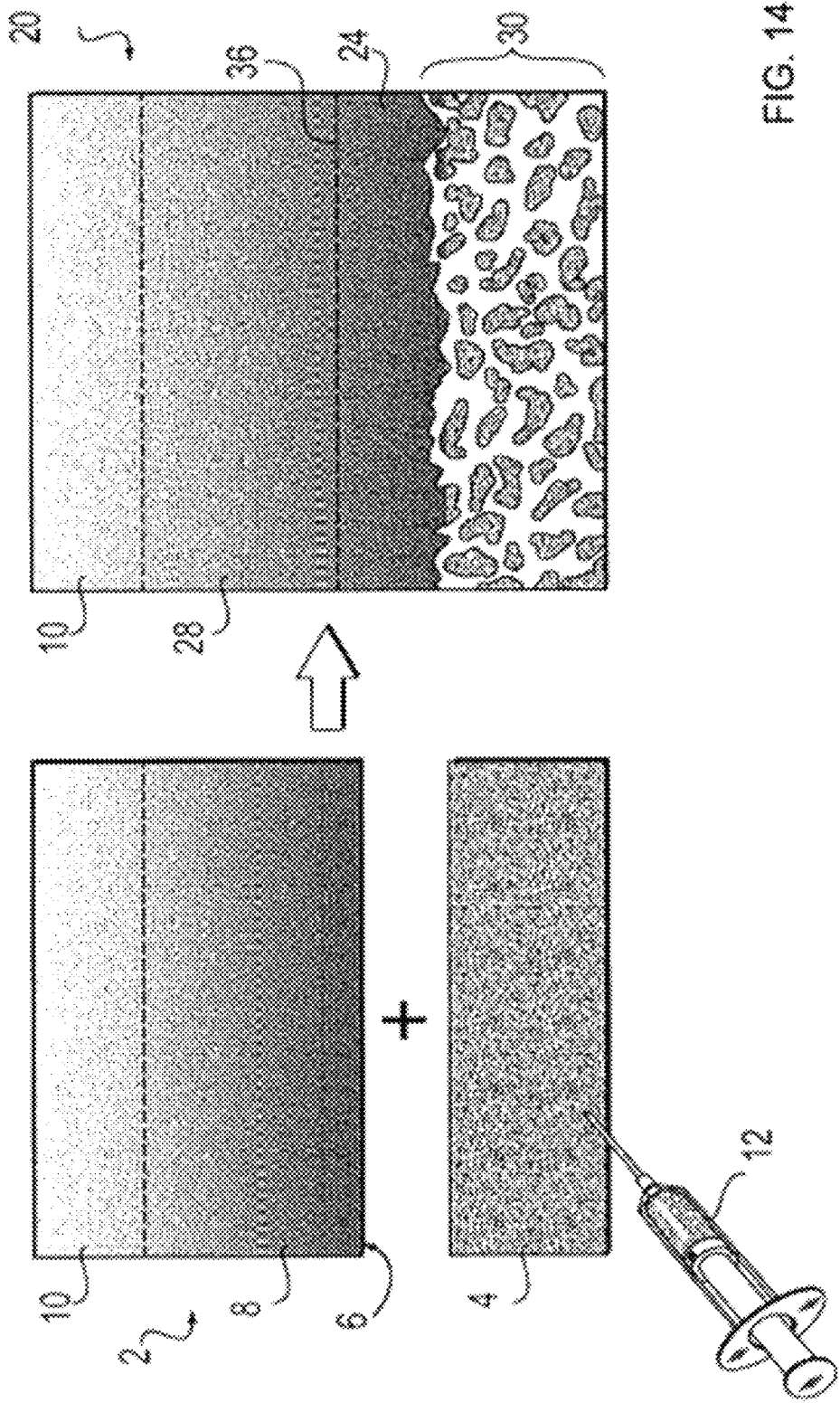
FIG. 14 shows an orthopedic implant being attached to a surface of a joint in accordance with some embodiments.

FIG. 14 illustrates one embodiment of the present disclosure. Medical implant 2 having a lubricious, hydrated articulation surface 10 and a stiff, attachment side 8 is fixed to bone 30 by means of an adhesive polymer 24 that acts as an intermediary between bone 30 and the attachment surface 6 of the implant 2. Although the attachment side 8 is illustrated as fixed to bone 30, the attachment side 8 can be attached in a similar manner to a portion of any of the implant surfaces described herein. In the illustrated embodiment, the adhesive polymer mixture 4 is separate from the implant and can be applied to either the attachment surface 6 of the implant or to bone 30, such as using syringe 12. After the implant and bone are brought together and the adhesive polymer mixture is cured and hardened to form the adhesive polymer 24, the implant 20 is fixed to the bone. The mechanism of adhesion of the adhesive polymer 24 and the implant attachment surface 6 or the bone 30 is chemical and/or physical, with the chemical adhesion including, e.g., covalent bonds formed between reactive functional groups found on the device material or bone and the chemical groups in the adhesive polymer and/or a variety of non-covalent interactions such as absorption (e.g., chemisorption, physisorption), hydrophobic interaction, crystallite formation, hydrogen bonds, pi-bond stacking, van der Waals interactions and physical entanglements between the device and the cured adhesive copolymer (e.g., at the molecular level), mechanical interlocking. In some embodiments, the physical adhesion may be the result of in-filling or interdigitating of a bump(s), a depression(s), a groove(s), a pore(s), a rough area(s), a space(s) and/or other surface features. In some embodiments, the adhesive copolymer is interdigitated with cancellous bone. Some, all or none of the attachment surface may have features. In some embodiments, the attachment surface is smooth.

Figure 15B:
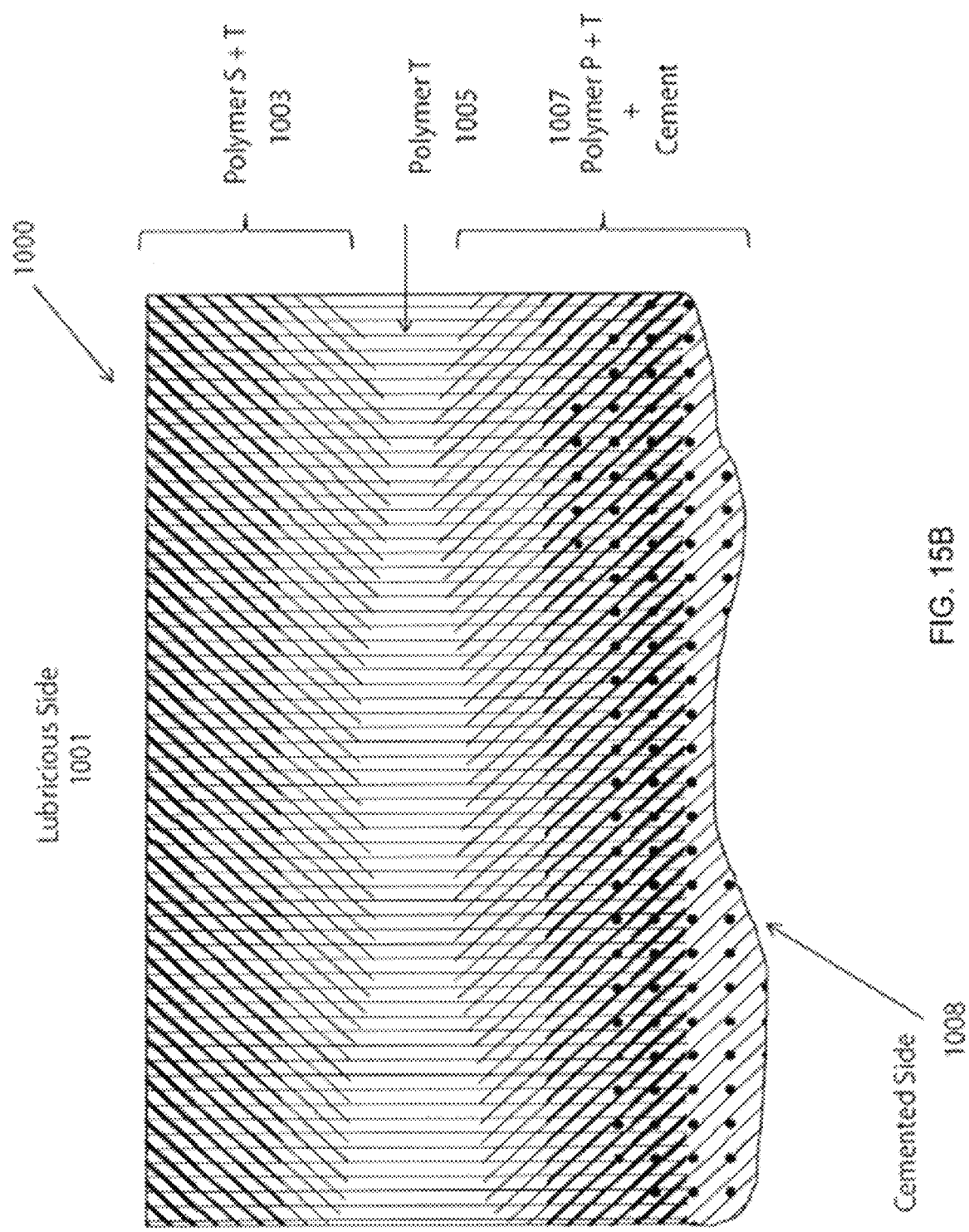

FIGS. 15A-15B illustrate one embodiment of a double gradient with a lubricious and adhesive gradient disposed on two different sides with a region of thermoset polymer material T 1005 between the gradients. The thermoset polymer material T can refer to the triple network IPN compositions described herein having a first polymer network comprising a hydrophobic thermoset or thermoplastic polymer, a second polymer network comprising a non-ionic polymer, and a third polymer network comprising an ionic polymer containing sulfonic acid functional groups. The thermoset polymer material 1000 shown in FIGS. 15A and 15B has two gradients formed by two IPNs on two regions of the material 1000. The lubricious gradient is disposed in region 1003 and is formed from an IPN/semi-IPN made from a hydrophilic polymer S network within the thermoset polymer material T. The lubricious IPN area 1003 includes a surface section 1001 that provides a lubricious surface to engage with, for example, a joint region. On the other side of the material, is an adhesive gradient 1004 formed from an IPN/semi-IPN with a non-ionic polymer P network within the thermoset polymer material T. The adhesive IPN area 1004 includes a surface section 1002 that provides an adhesive surface to engage with bone through use of a cement 1006. As shown in FIG. 15A, the gradient regions 1003, 1004 and thermoset region 1005 are not separated in this embodiment by distinct boundaries. Rather, the regions gradually merge and transition from one to the other through a thickness of the material. For example, the concentration of the non-ionic polymer P network in region 1004 is shown as slanted lines that darken and widen from the thermoset region 1005 to the adhesive surface 1002. This shows that in some embodiments, the concentration of the non-ionic polymer P and the relative concentration of the adhesive gradient gradually increases from one region of the thermoset material to another without forming distinct boundaries between the sections. Similarly, on the lubricious side, the slanted lines showing the hydrophilic polymer S are wider and darker near the surface 1001 and gradually lighten as the slanted lines move toward the thermoset region 1005. This also shows that in some embodiments, the concentration of hydrophilic polymer S is greater at the surface 1001 and gradually diminishes through a thickness of the material toward region 1005. FIG. 15B further illustrates that in some embodiments, once the cement or anchoring compound 1006 is applied to the adhesive surface, the cement and the adhesive gradient merge to form a continuous region 1007 and a cemented side 1008 without distinct boundaries between the anchoring compound and the adhesive gradient 1004. In further embodiments, where the non-ionic polymer P in the cement 1006 and the adhesive IPN are the same (as indicated by the presence of the slanted lines in cement 1006 and region 1004), the non-ionic polymer P in the IPN and in the cement will merge and fuse to form a continuous composition.

In some embodiments the IPN composition can include a triple network or more than three polymer networks on a lubricous or bearing side. The attachment side/zone or more rigid side used for adhesion can also include a triple network. In some embodiments the attachment side/zone may include a double polymer network. In some cases, a double polymer network may be sufficient for the adhesion side to form a bond with the bone or implant surface having the desired physical properties.

The adhesive gradients can be formed with adhesive co-polymer compositions described in co-owned U.S. Patent Publication No. 2013-0103157 and U.S. Patent Publication No. 2013-0217829. Examples of kits, systems, and methods for combining polymers to form these co-polymer can be found in co-owned U.S. Patent Publication No. 2013-0103157 and U.S. Patent Publication No. 2013-0217829.

Yet another aspect of the present disclosure includes providing an adhesive gradient within the IPN compositions comprising a urethane dimethacrylate-methyl methacrylate copolymer comprising a plurality of first polymer regions based on urethane dimethacrylate alternating with a plurality of second polymer regions based on methyl methacrylate to thereby form the urethane dimethacrylate-methyl methacrylate copolymer. In some embodiments, the urethane regions (the urethane dimethacrylate regions or modified urethane dimethacrylate regions) comprise about 60% (w/w) to about 80% (w/w), about 60% (w/w) to about 90% (w/w), about 60% (w/w) to about 99% (w/w), or about 70% (w/w) to about 90% (w/w) of the adhesive copolymer. In some embodiments, the methyl methacrylate regions comprise from about 20% (w/w) to about 40% (w/w), from about 1% to about 20% (w/w), or from about 1% (w/w) to about 40% (w/w). In some embodiments, the UDMA regions include soft segments based on PTMO, and the soft segments have a molecular weight between about 100 Da and about 5000 Da. In some embodiments, the UDMA-MMA copolymer defines a compressive modulus between about 30 MPa and about 2000 MPa. In some embodiments, the UDMA-MMA copolymer defines a tensile modulus between about 30 MPa and about 2000 MPa. In some embodiments, the UDMA-MMA copolymer defines a failure strain between about 25% and 200%. As well as providing other advantages, such as excellent fixation capabilities and mechanical strength, UDMA combined with PMMA reduces the brittleness otherwise found in pure PMMA. In some embodiments, acrylated or methacrylated esters of phosphoric acid may be added to the adhesive.

The adhesive gradient can be formed within the IPN compositions in-situ by providing a bone cement composition to the attachment zone of the IPN composition and curing the bone cement composition to attach the attachment zone to a surface of a bone or a portion of an orthopedic implant engaged with a surface of a bone within the human body. The bone cement can be cured by providing a light source to the bone cement. The adhesive gradient would have a highest concentration of adhesive at the attachment zone.

At their contact interface, a polyurethane-based implant will form molecular entanglements and both physical and chemical bonds with the polyurethane-based adhesive. Bonding is facilitated in particular by the common polyurethane component in both materials. For example, a gradient IPN or semi-IPN will feature one side with a preponderance of PU and this side would bond well with the UDMA-MMA composite adhesive. The present disclosure provides a unique combination of polyurethane polymer chains and an MMA monomer in a UV-curable adhesive that has sufficient mechanical properties for orthopedic, medical, commercial, and industrial applications that have high mechanical demands.

Figure 16A:
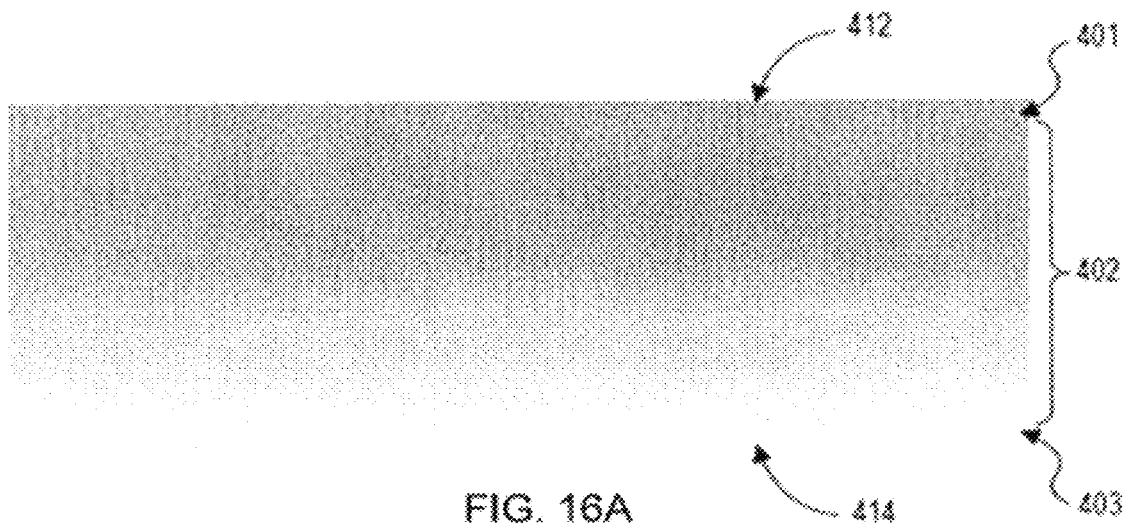
FIGS. 16A-16B show a gradient polymer alloy (FIG. 16A) and a porous metal device (FIG. 16B) before being joined in accordance with some embodiments.
Figure 16B:
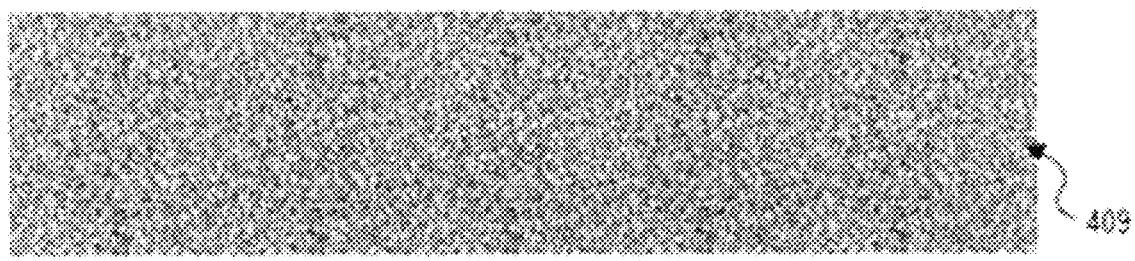
Figure 17:
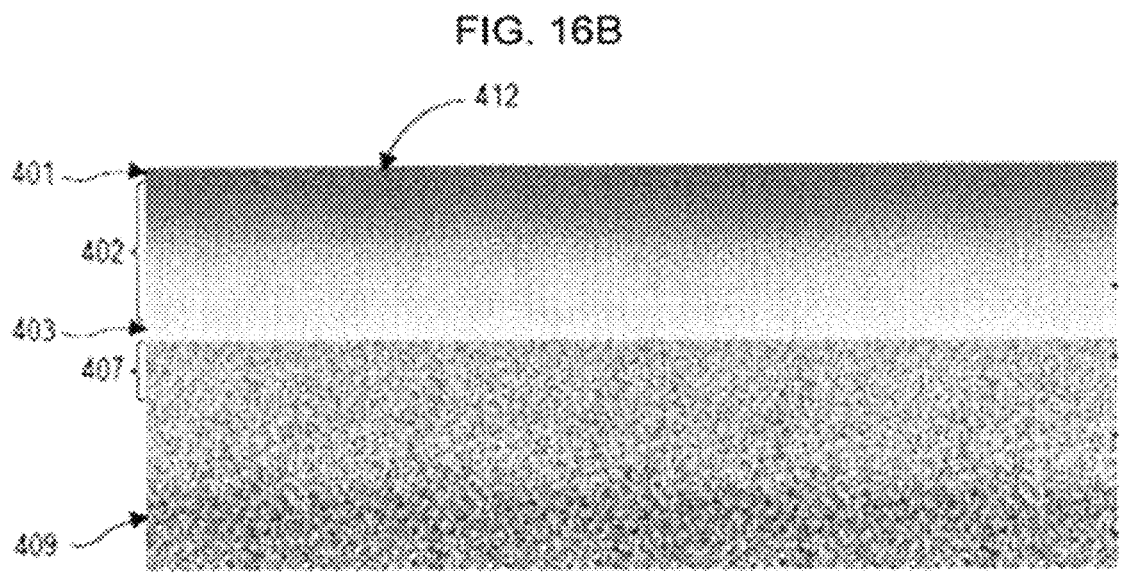
FIG. 17 shows a gradient polymer alloy device with gradient polymer and a porous metal device after joining in accordance with some embodiments.

Any of the IPN compositions described herein can be combined with the implants described in the foregoing description. For example, any of the IPN compositions can be used in the polymer metal alloys described herein. FIG. 17 shows the gradient polymer metal alloy of FIGS. 16A-16B joined with a bone interface member (metal device including hydrated phase 401 (with a bearing surface 412), transitional phase 402, non-hydrated phase 403, interfacial zone 407 comprising non-hydrated polymer from the attachment zone 414 interdigitated with porous metal, and porous metal from bone interfacing member 409. The gradient polymer alloy is mechanically interdigitated with porous metal to create a strong, smooth interface region.

A bone interfacing member may be any material, but preferably is one useful in orthopaedics and biocompatible, such as a metal, ceramic, or polymer. A bone interfacing member may be any metal, such as aluminum, cobalt, molybdenum, nickel, stainless steel, titanium, tantalum, or combinations or alloys thereof and/or any other metals used in biomedical implants. A bone interfacing member may be any polymer that is sufficiently strong and biocompatible, such as PEEK, polyurethane, or UHMWPE. For simplicity, a bone interfacing member will be referred to as a metal, but it should be understood any material that connects a polymer gradient alloy to a bone can be used. A metal may be substantially solid, porous, etched, coated, or otherwise treated to aid in attaching the metal to bone and/or attaching a gradient polymer alloy to the metal, or may have a combination of these characteristics or treatments. A porous metal includes but is not limited to porous "trabecular" metal, porous metal foam, sintered metal beads (e.g. that form a porous structure), plasma sprayed porous metal, and/or chemically etched porous metal. A portion of the metal may be solid, porous, rough, etched, coated with osteoconductive material (e.g. calcium phosphate or hydroxyapatite), or otherwise treated and another portion not solid, porous, etched, coated, or otherwise not treated. In one example, a metal is porous on the bone contacting surface. In another example, a metal is porous on a polymer alloy facing side. In another example, a metal is porous on both a bone contacting surface and a polymer alloy facing side. A hydration gradient polymer alloy may be a combination of a hydrophilic polymer and a hydrophobic polymer, such that one side of the alloy is hydrophilic and hydrated, and the other side non-hydrated and hydrophobic. The latter side may be mechanically interdigitated or chemically bound with a metal bone interfacing construct. If a porous metal is used, the porosity may be any that allows or aids in attaching to a gradient polymer alloy or in attaching to bone. The porosity of the metal may be similar to the porosity of cancellous bone.

The gradient polymer alloy can be attached, connected or bound to the metal in any way.

In one example, the gradient polymer alloy was placed in contact with a porous metal specimen that was heated past the melting point of the polymer backing material. The two materials were compressed together under a load of, for example, 1 metric ton, and then allowed to cool. The result was a gradient polymer alloy fused to a porous metal. Examples of porous metals used were aluminum and titanium.

Figure 18A:
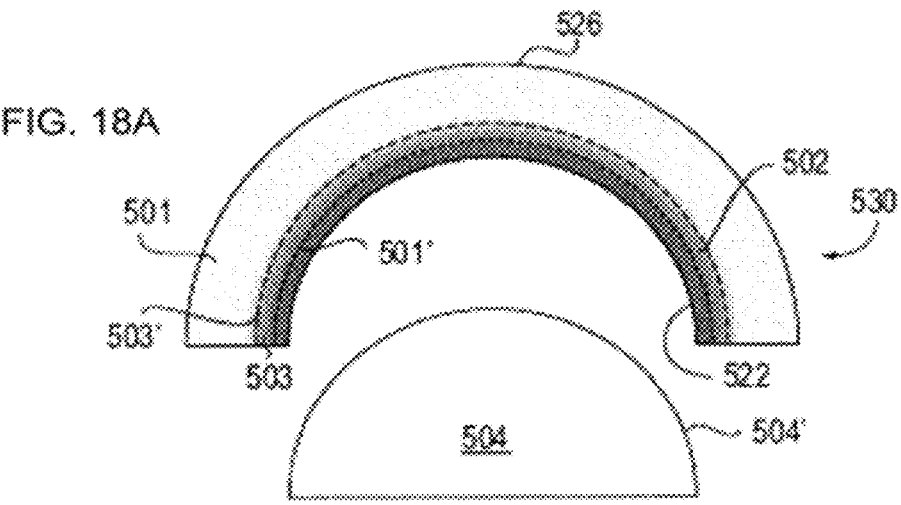
FIGS. 18A-18C and FIGS. 19A-19D show the steps of attaching a cap-shaped (FIG. 18A-C) and a cup-shaped (FIG. 19A-D) metal implant having a gradient polymer alloy bearing surface to a bone in accordance with some embodiments.
Figure 18B:
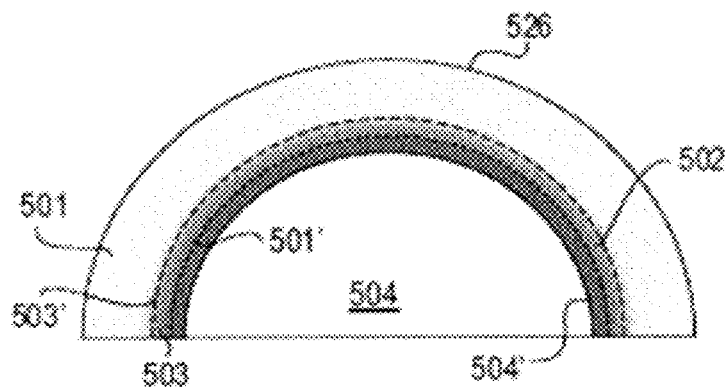
Figure 18C:
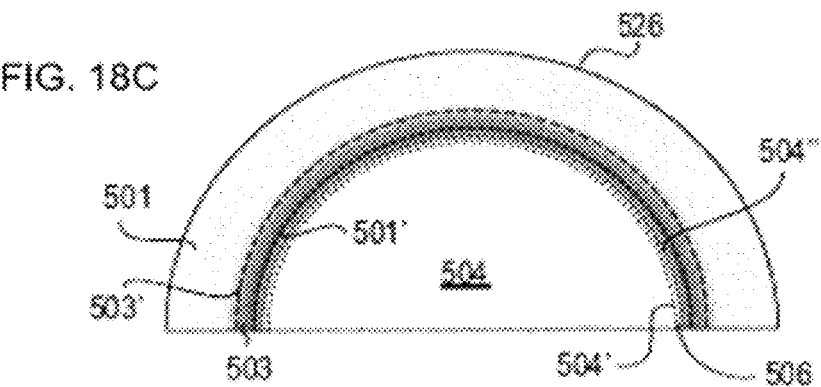
Figure 19A:
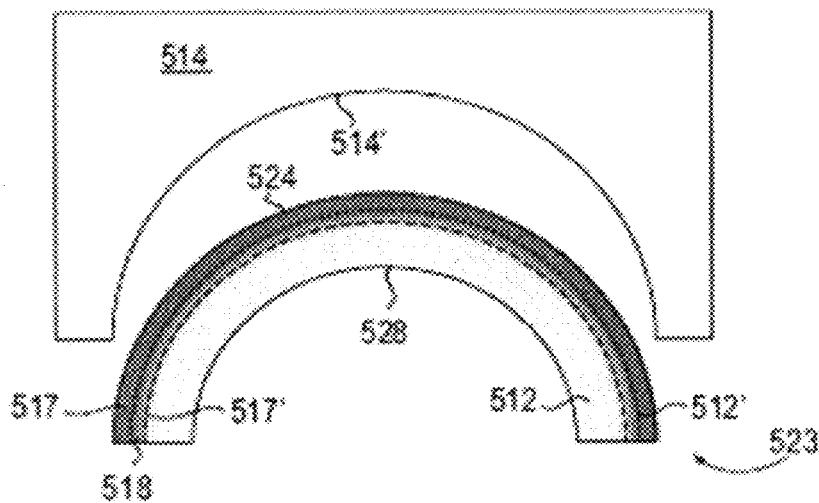
Figure 19B:
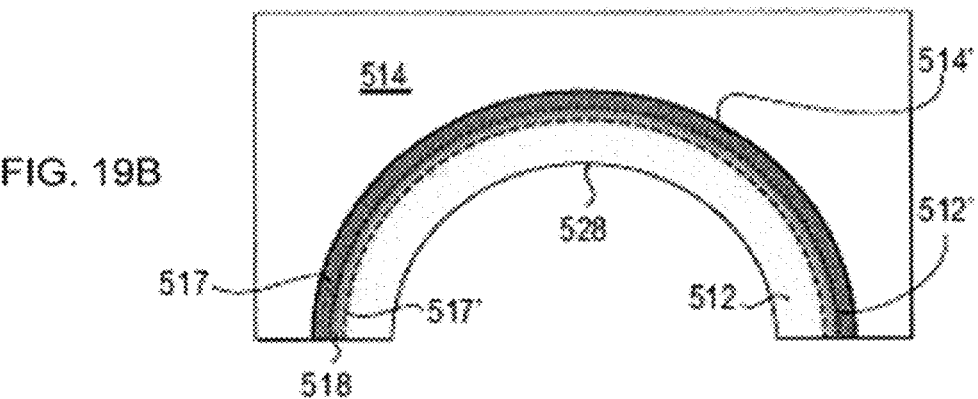
Figure 19C:
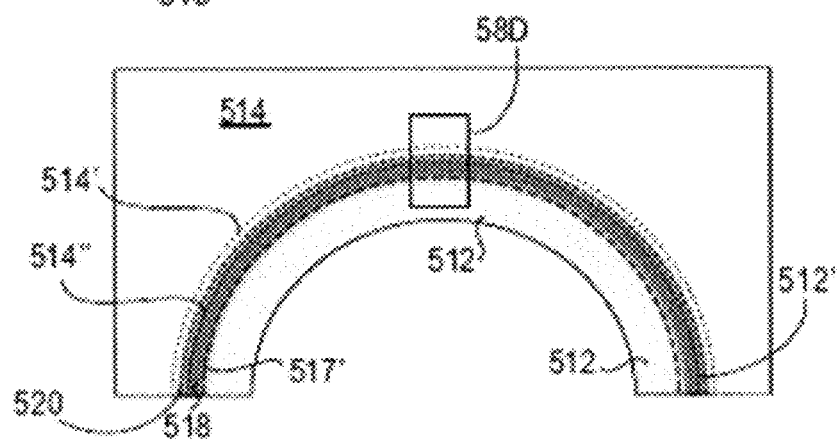
Figure 19D:
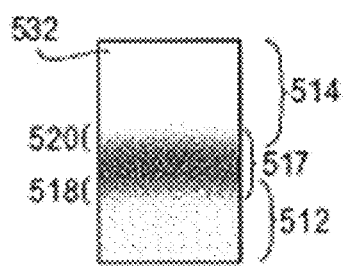

The use of porous metal or polymer in combination with a gradient polymer alloy allows for bone in-growth into the metal or polymeric bone-facing side of a device to create a strong but lubricious joint replacement having gradual transition from hydrated surface to strong bone. Polymer/metal and metal/bone regions of overlap are shown in FIGS. 18A-C and 19A-D. FIGS. 18A-C show a porous metal or polymer counter-surface (bone interface member), though the surface may also be non-porous. FIGS. 18A-C and FIGS. 19A-D show orthopedic implants in the shape of a cap 530 (FIG. 18A) and a cup 523 (FIG. 19A) being attached to and in-grown with bone. The implants have hydrated polymer portions 501, 512 to provide bearing surfaces 526, 528 to interface with a joint surface. The hydrated polymer portion of the gradient polymer alloy and porous metal have been interdigitated 503 (518) in the region between 503' and 501' (512' and 517') to create a polymer/metal overlap region 502, 518. The implants also have porous metal portions 501, 517 with bone attachment zones 522 (524) to attach the interdigitated polymer metal implant 530, 523 to bone. When implant 530, 523 is placed next to bone 504, 514, the implant forms a new artificial joint surface on the bone. Post-operatively, bone grows into the porous metal side to create metal-bone integrated region 506, 520 between original bone surface interface 504' and new interface 504" (at the limit of the bone in-growth) that can strongly anchor the implant to a bone. The interdigitated metal-bone region distributes stresses better than does a sharp interface between the two materials, providing a strong anchor. An expanded view of the interfacial zone 508 is shown in FIG. 18D with bone 514 connected with metal implant 517 which is in turn connected with cartilage replacement polymer 512. FIG. 19D shows a closer view of the region shown in FIG. 19C overlap or interdigitation 520 between bone and metal, overlap or interdigitation 518 between polymer 512 metal 518, and transition from strong metal to lubricious surface 532 to create a strong, smooth joint replacement.

Figure 20A:
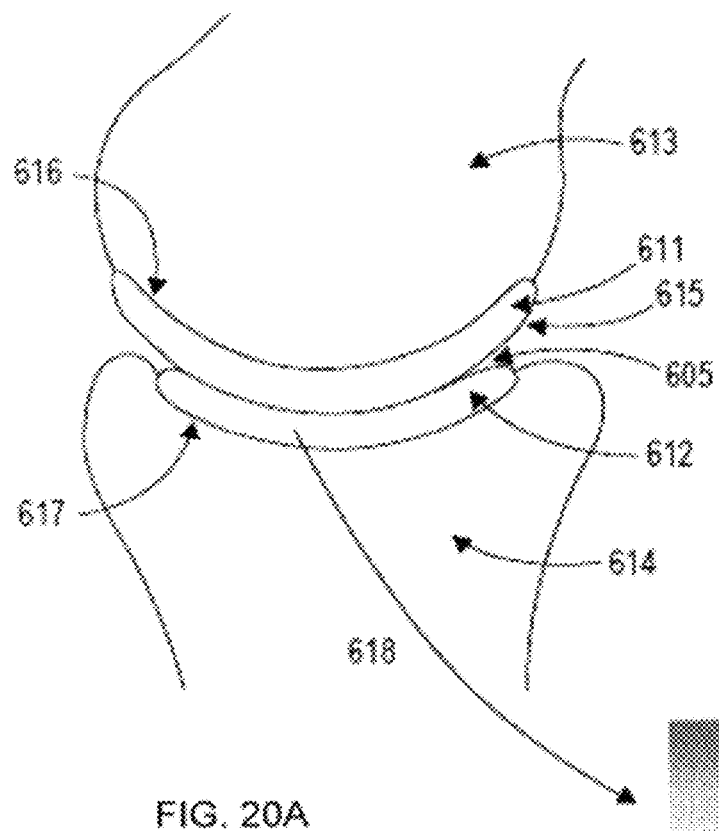
FIG. 20A shows both sides of a joint replaced with a metal implant having a gradient polymer alloy bearing surface.
Figure 20B:
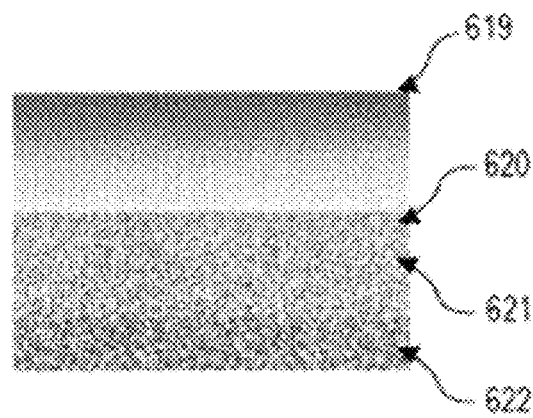
FIG. 20B shows a cross-section of the implant from FIG. 20A in accordance with some embodiments.

FIG. 20A shows two sides of a generic articular joint with both sides of the joint replaced with orthopedic implants according to the current disclosure. Concave bony prominence 614 has bone surface 617 accepting concave articular component 612. Convex bony prominence 613 has bone surface 616 accepting convex articular component 611. Concave articular component 612 mates with convex articular component 611 at articular interface 615. Cross section 618 of concave articular component 612 is shown in FIG. 20B immediately after being placed in the joint, i.e., before any bone ingrowth has occurred. Next to the bone is a layer of porous metal 622 serving as a bone interface member, then a polymer-metal interface region 621, non-hydrated side 620 of the polymer and, facing the articular surface, hydrated side 619 of the polymer.

In one example, a gradient polymer alloy can be physically snap-fitted into a metal mating component with a non-porous smooth contact surface and a counter-surface (bone contact surface) configured for attaching to bone that is porous, rough, and/or coated with osteoconductive material such as calcium phosphate or hydroxyapatite. In this case, a gradient polymer alloy component may be used similarly to the way that existing ultrahigh molecular weight polyethylene (UHMWPE) acetabular cups are fitted into metal backing components.

In another example, a gradient polymer alloy can be physically snap-fitted into a mating, polymeric component with a non-porous smooth contact surface (attachment surface) and a counter-surface (bone contact surface) meant for anchoring to bone. A counter-surface may be porous or non-porous. A counter surface may be coated with an osteoconductive material such as calcium phosphate or hydroxyapatite. Anchoring a gradient polymer alloy to bone can be achieved through any suitable means including one or more of: 1) bone ingrowth into a porous counter-surface (bone contacting surface), 2) briefly melting an entire surface or portions of a surface of a solid counter-surface and causing the material to flow into the bone pores, and solidifying the material to form a grout-like anchoring, 3) using or applying adhesive, cement (e.g. polymethylmethacrylate (PMMA)), epoxy, glue, or grout, to bind (e.g. chemically) or mechanically hold a counter-surface to bone.

In another example, a gradient polymer alloy may be chemically bonded to a metal portion or implant. Either (or both) sides of a metal maybe smooth, porous, or rough. Any number or type of chemical bonds may be made. In one embodiment a urethane linkage is formed between a polyurethane-based gradient polymer alloy and a tribochemically modified metal surface through reaction of terminal isocyanates in the polymer precursor and reactive —OH groups on the metal surface. A metal surface can be tribochemically modified with oxides, which can subsequently be further modified to hydroxyl groups, which can in turn be chemically reacted with free isocyanate groups to form an isocyanate chemical bond (see Myung et al., U.S. Patent Application Publication 2008/0241214). Alternatively, the bone cement, such as the bone cement compositions disclosed in U.S. Patent Publication No. 2013-0217829, can be formed on a surface containing methacrylate (or similar) groups so that upon free radical polymerization of the bone cement, it also is grafted to the surface while also fusing to the implant on the other side. The gradient polymer alloy can also be joined to the bone interfacing member using or applying adhesive, cement (e.g. polymethylmethacrylate (PMMA)), epoxy, glue, or grout.

A gradient polymer bound to a metal surface may have any thickness. A gradient polymer may form a thin coating or layer over a metal surface. A coating or layer may be less than 30, less than 25, less than 20, less than 15, or less than 10 mm in a thickest region. In one particular example, a coating on a metal is less than 5 mm in a thickest region.

A gradient polymer alloy may be polyurethane based, and the polyurethane side of the alloy may be physically fused with a porous metal by melting a portion of the polyurethane and flowing it into pores of the metal, and then cooling the metal and polyurethane. Because a polyurethane side of a gradient polymer can be tough and hydrophobic, it is able to robustly anchor to the porous metal with an interface that is highly resistant to extreme and repetitive mechanical stresses.

An implant or device may be made after separate fabrication of a gradient material and a porous metal, and then the material and metal are fused. They may be fused by heating the metal, apposing the material and the metal, compressing the material and metal together, and then cooling the metal. In this way, the hydrophobic side of a gradient polymer is "melted" into the pores of a porous metal. Alternatively, a precursor of a gradient polymer can be injected molded directly onto a (pre-fabricated) porous metal, followed by post-processing of the polymer to yield a gradient polymer that is fused to the metal. The "melting" can also be achieved by means of ultrasonic welding, laser welding or thermo welding.

In another aspect of the disclosure, a synthetic joint capsule may be implanted. A synthetic joint capsule may surround one or both (or may be near, but not surround) implant components. A capsule component(s) may be closed or sealed to contain a fluid such that fluid cannot move in and out of a volume or space created, at least in part, by the capsule.

Figure 21:
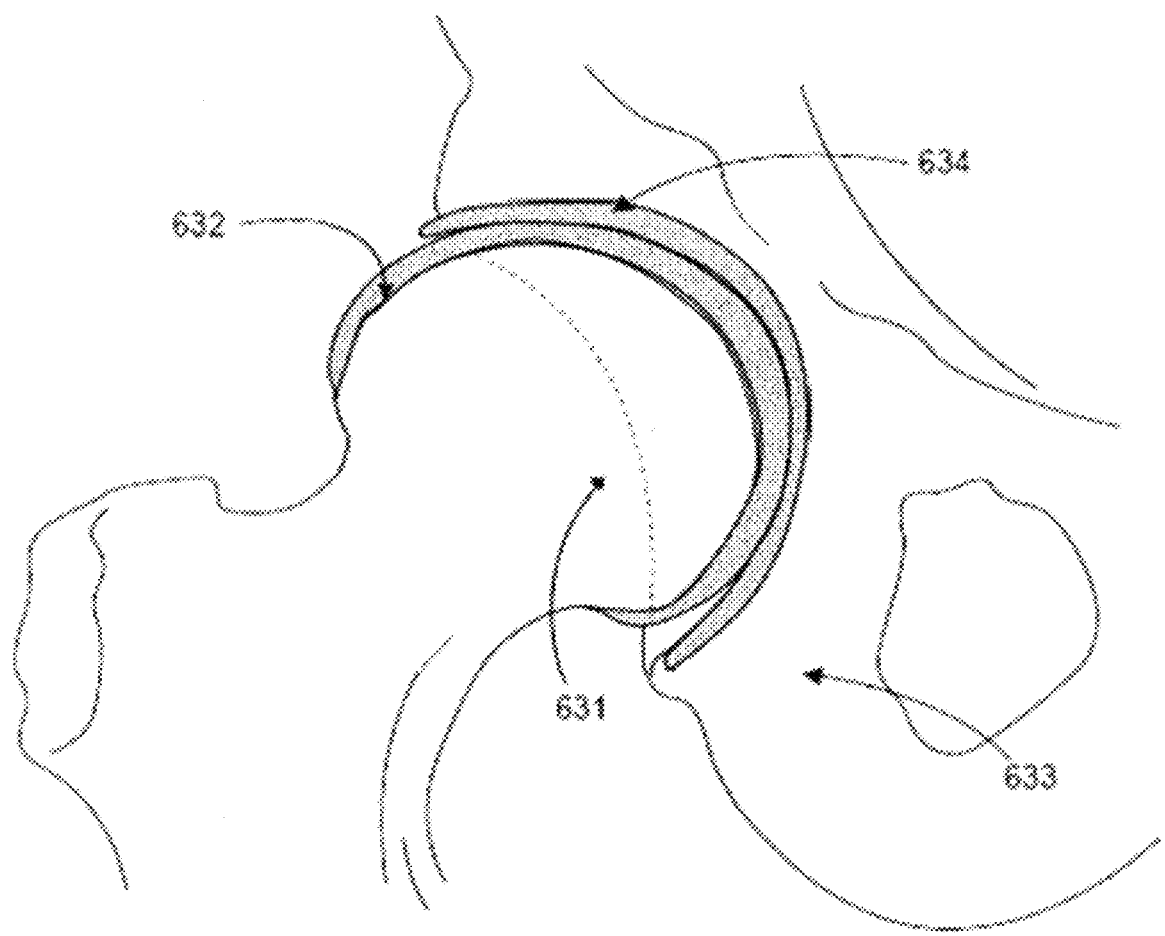
FIG. 21 shows a cap-on-cup total cartilage replacement in a hip joint in accordance with some embodiments.
Figure 22:
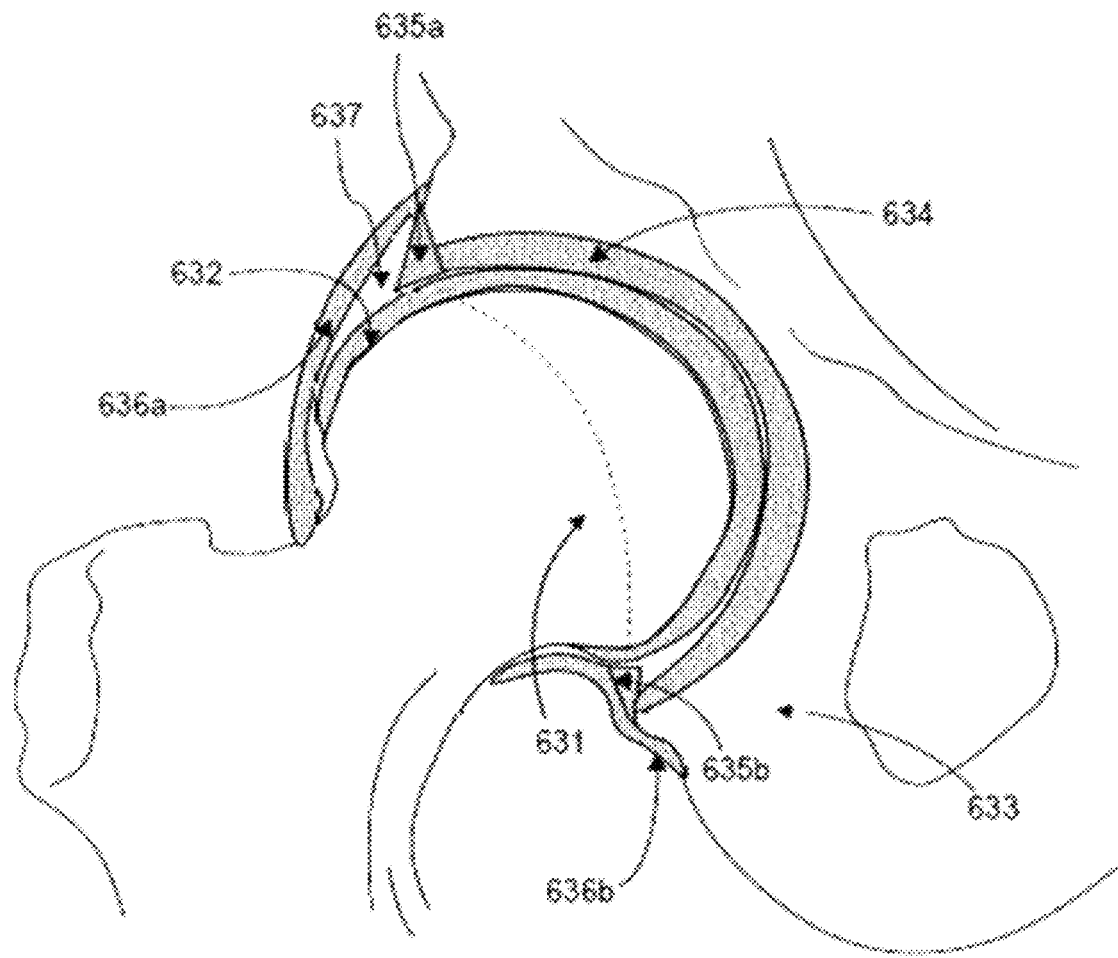
FIG. 22 shows a hip replacement system with cap-on-cup cartilage replacement implants such as the ones shown in FIG. 21, a synthetic joint capsule component, labral components and lubricant fluid in accordance with some embodiments in accordance with some embodiments.

FIGS. 21-22 illustrate placement of cap-on-cup, synthetic joint capsule and labral implants of a gradient polymer in a hip joint according to one aspect of the disclosure. FIG. 21 is a simplified version showing total cartilage replacement with convex articular component cap 632 over femoral head 631 and concave articular component cup 634 facing acetabulum 633 without a synthetic joint capsule or synthetic labral components in place. The components (e.g. cap and cup) are made from a gradient polymer alloy without a metal component.

FIG. 22 shows a total cartilage replacement device based on gradient polymer alloy components with the components shown in FIG. 21 and encapsulation of the hip joint with a capsule component 635, shown in superior cross-section 636a and inferior cross-section 636b, a labral component shown in superior cross-section 635a and inferior cross-section 635b, and containing lubricant fluid 637. In this embodiment, the capsule 635 encloses the entire joint, including the cap 632 and cup 634 described above. Capsule 635 may contact bone, joint implants or both to form its joint enclosure.

A joint capsule may be part of a gradient polymer and porous metal combination implant, or may be present in an implant having a gradient polymer without a porous metal component. A synthetic labral component may also be used in combination with the femoral and acetabular components, with or without a synthetic joint capsule component. The same holds true for the humeral head and glenoid in a shoulder joint.

The capsule's geometry and shape may similar to all or part of a natural joint capsule, which normally provides stability to the joint. In one example, a synthetic joint capsule contains a phosphate buffered saline or normal saline solution, which may serve as a lubricant fluid for a gradient polymer bearing surface(s). A synthetic capsule may be manufactured as an attached part of one or more bearing components, or may be a separate part. It may be assembled either pre-operatively or intra-operatively with another joint component(s). In another example, the capsule may be filled with a lubricant, such as a lubricating polymer (e.g. carboxymethyl cellulose, hyaluronic acid, or sodium polyacrylate).

The addition of a synthetic capsule may provide advantages, such as protection against dislocation, containment of wear debris, protection of the articular interface against host cells, or bone or cement particles, and/or creation of a one-piece device that may be implanted in a single step, much like an interpositional spacer device.

Figure 23:
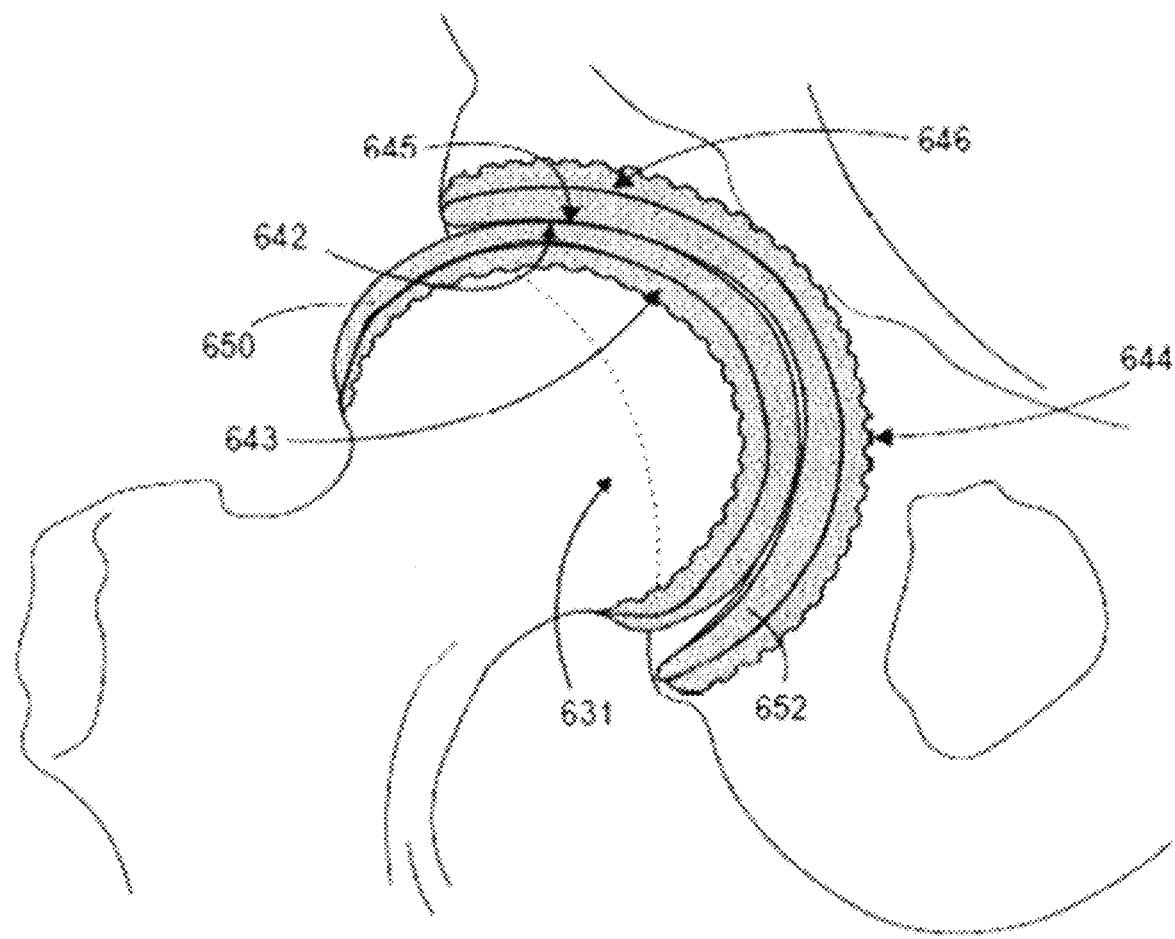
FIG. 23 shows a cartilage replacement system with cap-on-cup metal implants having gradient polymer alloy bearing surfaces in accordance with some embodiments.

A total cartilage replacement metal device with a polymer cap-on-cup surface may be placed in a joint. FIG. 23 shows a cartilage replacement device placed in a hip joint. Femoral component 650 is in place over femoral head 631. It includes has porous metal backing 643. Acetabular component 645 abuts acetabulum 644. Component surfaces 642, 645 mate to provide a joint interface. One or both component surfaces 645, 642 may be a polymer. FIG. 23 also shows porous metal backings 646, 643.

Figure 24:
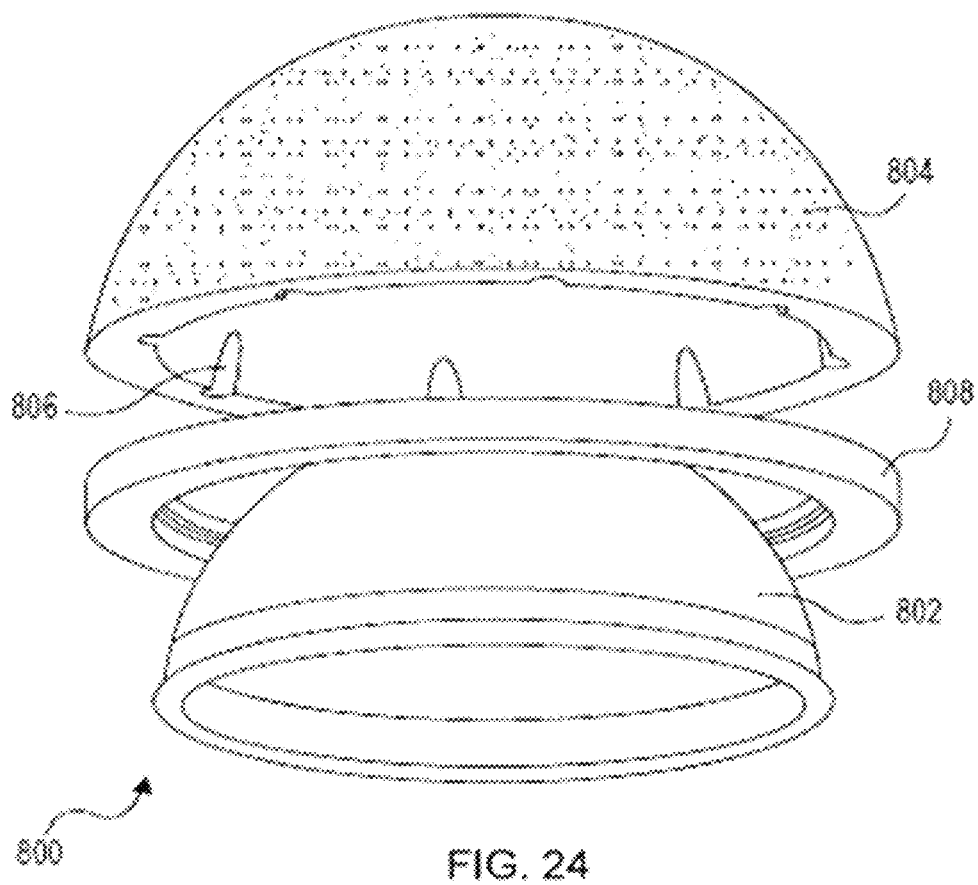
FIG. 24 shows another embodiment of a metal implant having a gradient polymer alloy bearing surface.

An implant according to the disclosure may be assembled before insertion into a joint region or two or more parts may be assembled intraoperatively while in the joint. FIG. 24 shows a metal implant and a gradient polymer liner that can be separately inserted into a joint. Metal cup 804 may be first placed in a joint, then gradient polymer liner 802 may be placed. Polymer liner 802 may be attached or adhered to metal cup 804 in any fashion. It may be held by chemical bonds or physical means. FIG. 24 shows grooves 806 for holding or flowing a material to aid in attaching a liner to a metal portion. The metal or the polymer liner may have features that change shape to aid in attachment, such as tabs. The metal cup and liner may be adhered using adhesive, cement (e.g. polymethylmethacrylate (PMMA)), epoxy, glue, or grout. FIG. 24 shows an optional ring to secure the liner to the metal. The ring may interlock or screw the liner to the metal. In one example, a liner can be removed and replaced with a new liner without removing the metal portion.

For a femoral device, a gradient IPN "cap" may be designed to fit on top of a metal femoral cap. A modular arrangement may allow a wider range of size interchangeability and tolerances in terms of the fit between a convex and concave joint surface. In addition, it may allow for various cup geometries for different pathologies. For example, it would allow for metal cups/backings with screw holes for additional fixation in the case of poor bone. It may also allow for a dysplasia cup and finned cups. A modular arrangement gives flexibility to adapt to patient needs and surgeon preference, which may be decided intra-operatively. The modularity may be enabled by mechanism. Modularity may be enabled by a locking mechanism, such as a taper, deforming tab, and a "screw-in" mechanisms. Typically, with modular systems on the market today, the liner (poly, ceramic, metal) is assembled to the metal cup as a last step. This allows the surgeon to perform a final trialing prior to final implantation. It also gives the surgeon the option to use a lipped liner for additional stability should he deem it necessary at time of surgery. Any of these mechanisms may also be used with a non-modular (e.g. preassembled) device. Modularity also provides the option of replacing just the bearing materials in the artificial joint for various reasons without disturbing the bone interfacing members.

Another aspect of the present disclosure provides methods and implants for changing a shape of an implant. A metal, especially a porous metal, may have some ability to deform (e.g. bend, crimp, expand, fold, stretch, twist) or otherwise change a shape under an applied stress. A shape change may be transient. A metal may deform by bending one or more struts or regions along a metal meshwork.

In one example, an implant may cover an area greater than 180 degrees of a bone. For example, a hip implant for a femoral cap may encompass greater than 180 degrees, as shown in FIG. 23. The deformability of the porous metal and the polymer to which it is attached allows the entire cap to deform (e.g., open, stretch or otherwise change its spatial configuration or spatial conformation) to enable it to be placed over a spherical femoral head. A tool can be used to return the device to a different or preferred shape, such as to contact more of the femoral head or femoral neck surface. Metals with good shape memory properties would be useful in this particular embodiment.

An implant having a porous metal surface and a flexible or deformable polymer may change a shape. Any metal that can change a shape may be used. Any polymer that provides a biocompatible surface useful in a joint replacement may be used in an implant. A polymer on a surface may create a slippery, a soft, and/or a smooth surface. A polymer may be a lubricious polymer. In one example, an implant polymer is a gradient polymer alloy as described herein.

One aspect of the present disclosure involves methods for inserting an orthopedic implant into a joint.

Figure 30:
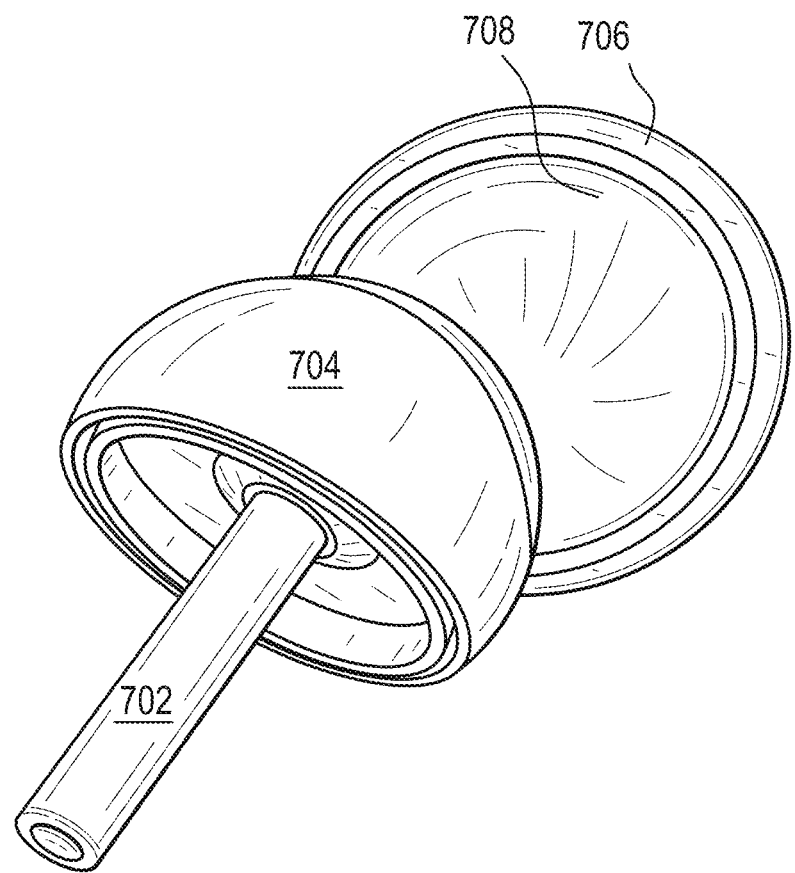
FIG. 30 illustrates a hip implant with IPN compositions in accordance with some embodiments.

In some embodiments the IPN compositions described herein can be added to a surface of a traditional orthopedic implant. FIG. 30 illustrates a hip implant with IPN compositions in accordance with some embodiments. The femoral head 702 includes an IPN composition 704 and the acetabular cup 706 includes an IPN composition 708. The IPN compositions 704, 708 provide lubricious surfaces that can articulate relative to one another.

Figure 31B:
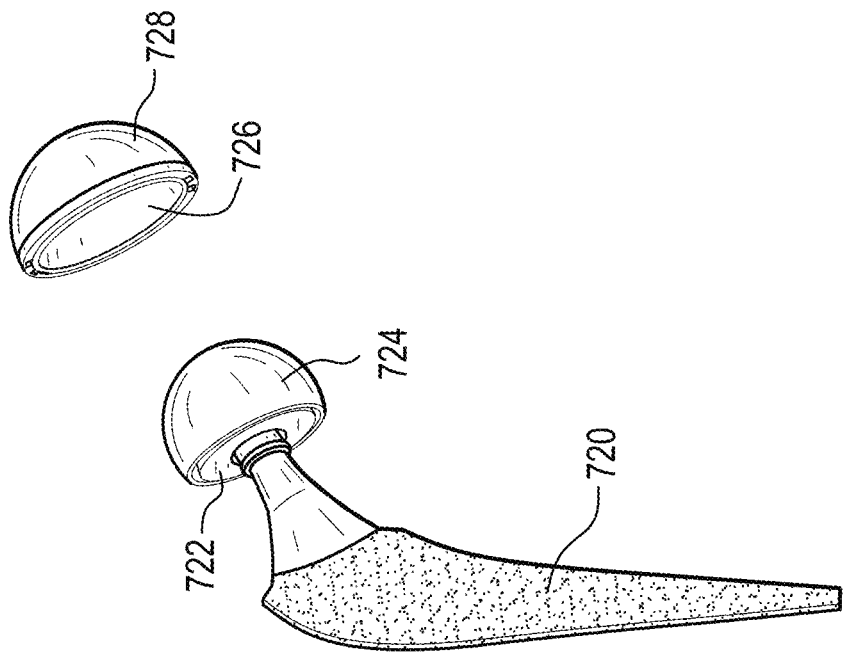
FIGS. 31A-31B illustrate an exploded view and assembled view of components of a hip implant with IPN compositions in accordance with some embodiments.
Figure 31A:
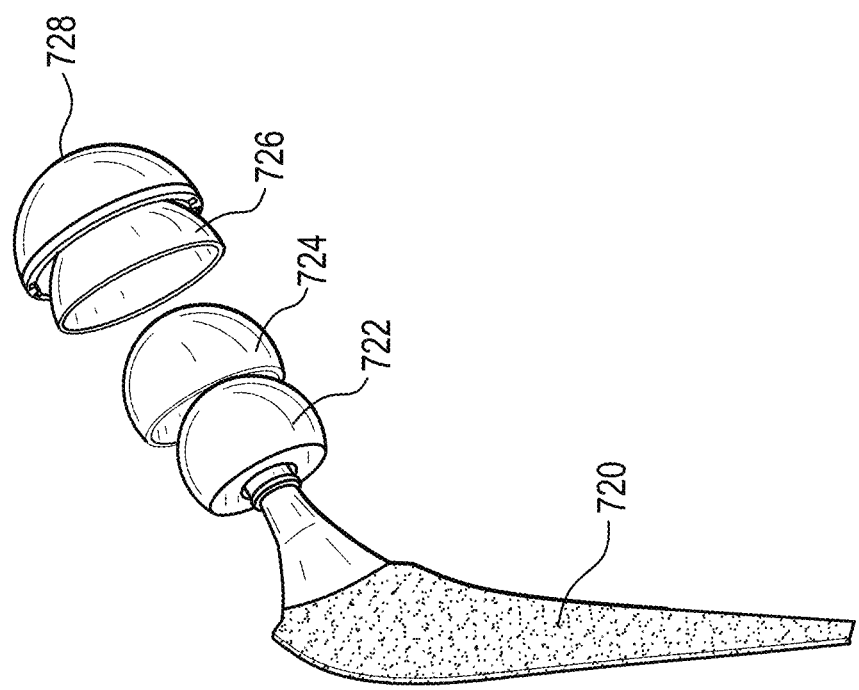

FIGS. 31A-31B illustrate an exploded view and assembled view of components of a hip implant with IPN compositions in accordance with some embodiments. The illustrated implant system includes a femoral pin 720 with a femoral head 722 and an acetabular cup 728. The femoral head 722 can include an IPN composition 724 applied over an articulating surface of the femoral head. The acetabular cup 728 can include an IPN composition 726. The IPN compositions 724, 726 provide lubricious surfaces that can articulate relative to one another.

Figure 32:
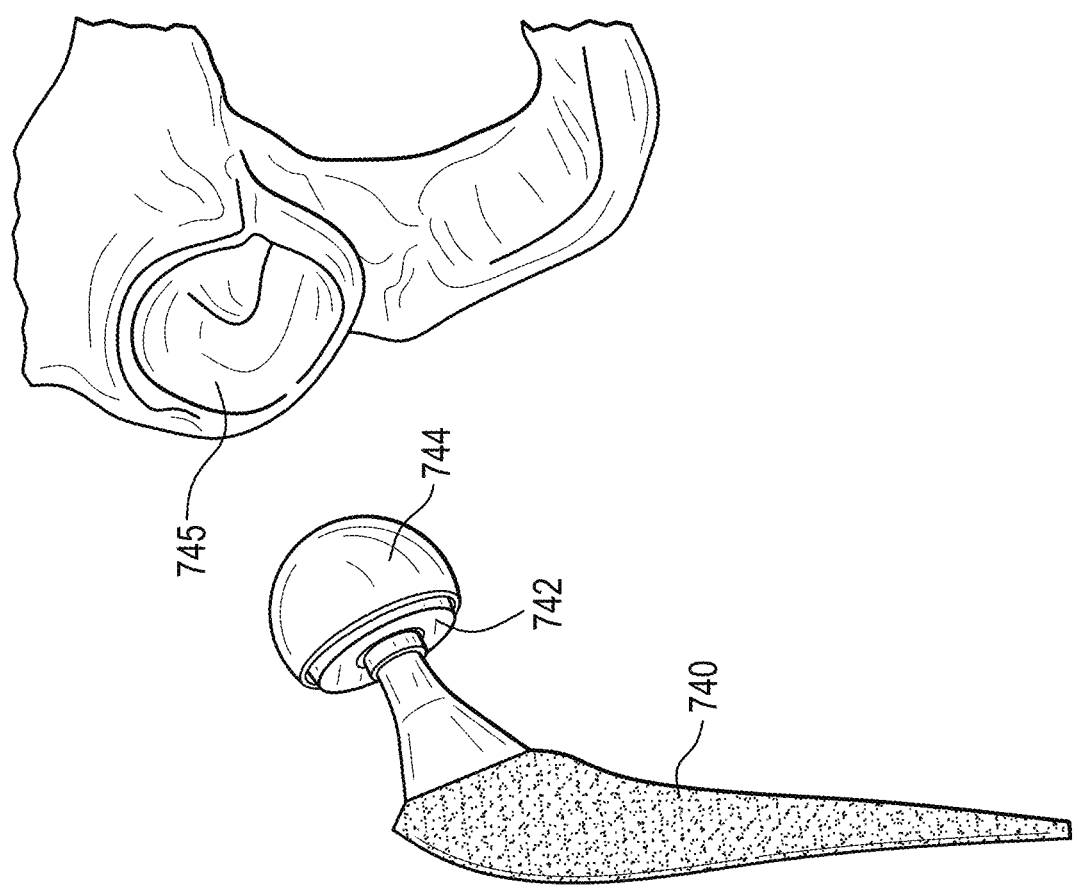
FIG. 32 illustrates a component of a hip implant having an IPN composition in accordance with some embodiments.

FIG. 32 illustrates a component of a hip implant having an IPN composition in accordance with some embodiments. The implant system illustrated in FIG. 32 can be used for a hemiarthroplasty procedure to treat hip fracture, avascular necrosis, and other medical problems. The implant can include a femoral step 740 and a femoral head 742 with an IPN composition 744 over the articulating surface of the femoral head. The IPN composition 744 can be used to articulate with natural cartilage 745 in the pelvis/hip.

A shape of an implant may be changed for any reason. A change in shape may provide an implant with a smaller size to aid in implant insertion (e.g. for arthroscopic or minimally invasive surgery). A change in shape or size may allow an implant to fit into a joint region. For example, a shape may be changed to allow an implant to fit over a femoral head. A shape of an implant may be changed so that the implant conforms to at least a portion of a shape of a joint. For example, a portion of a joint may have an irregular surface and an implant shape may be changed to abut or fit a shape of the surface.

Figure 25:
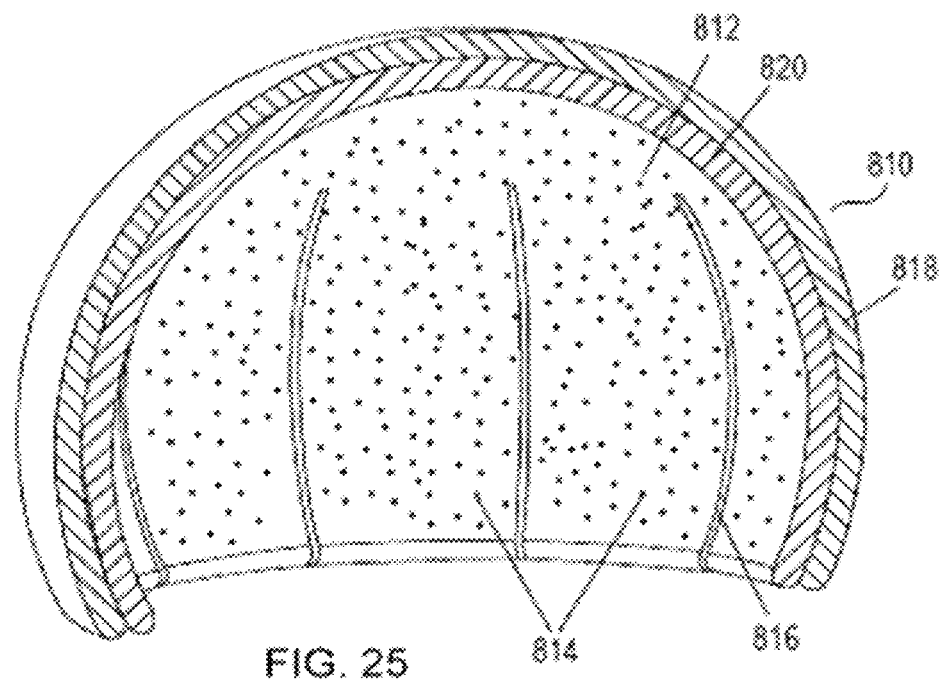
FIG. 25 shows a metal implant with expansion gaps and a deformable polymer for placement in a joint in a body in accordance with some embodiments.

FIG. 25 shows another embodiment of an orthopedic implant able to change a shape, e.g. to aid in insertion into a joint. FIG. 25 shows implant (cap) 810 with metal portion 812 attached to polymer 818. Polymer 818 may be any flexible or deformable biocompatible polymer useful for joint replacement. In one example, it is a gradient polymer as described herein. Metal portion or back 812 has two or more discontinuous segments (or leaves) 814. There may be lines of separation or gaps 816 between the segments to allow the implant to change shape. The lines of separation may run in a longitudinal direction anywhere from a few degrees from the opening (collar) to well beyond the equator. The lines may allow the device to "open" transiently in a radial direction (like a claw or petal on a flower). Individual segments may be deposited on or attached to the polymer. Metal may be laid down on the polymer, and then portions removed (e.g. by laser etching) to leave segments. In another embodiment, portions or segments may be hinged, connected, or otherwise attached at the north pole (like a clamshell) and may open as the implant stretches out while being lowered over the femoral head. The portions or segments may close after being lowered to surround the implant and femoral head. A metal may be sufficiently flexible and resilient, yet rigid enough to snap back into position after a transient deformation. In another embodiment, the metal segments or portions are mostly discontinuous, but retain some continuity through flexible connecting elements. The elements may be, for example, curves, zig-zags, or springs.

Figure 26:
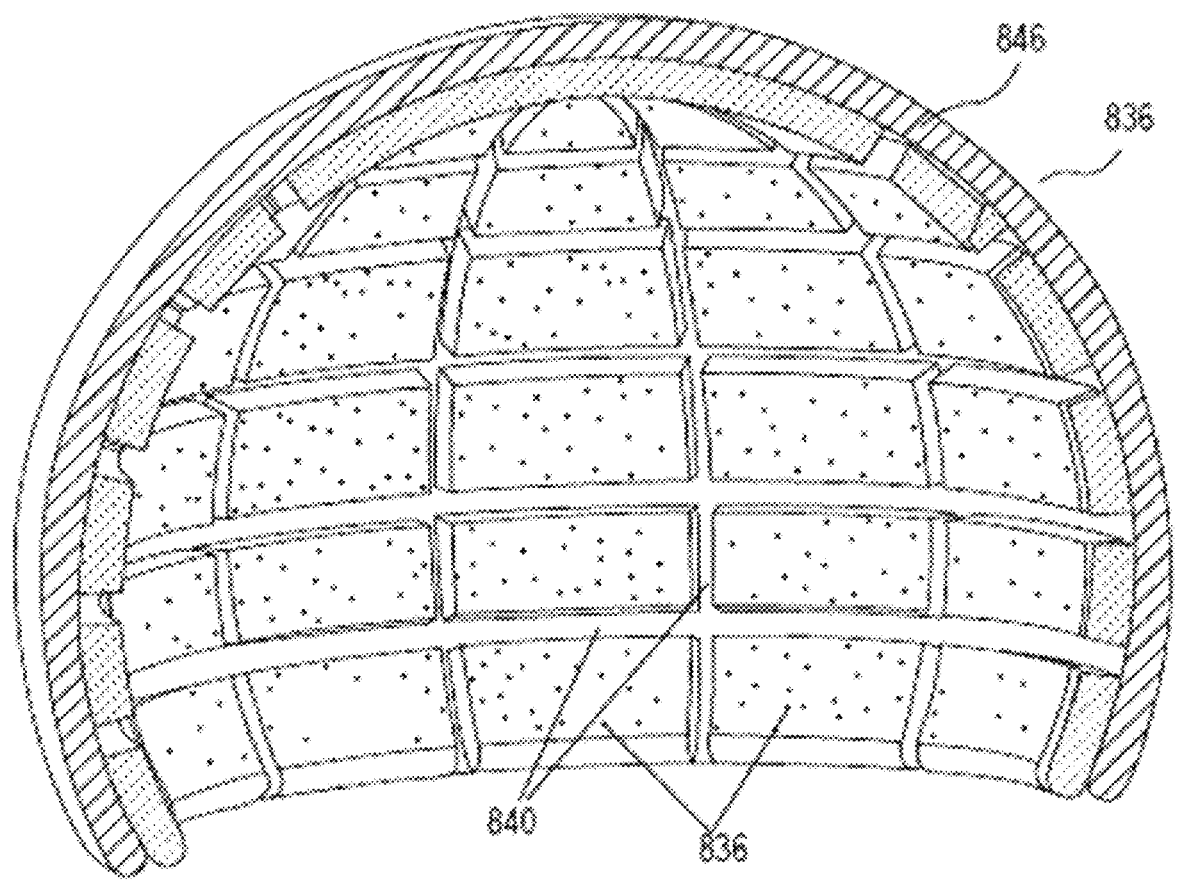
FIG. 26 shows an orthopedic implant with metal segments for placement in a joint in accordance with some embodiments.

FIG. 26 shows another embodiment of an orthopedic implant able to change a shape. Segments 836 of metal separated by gaps 840 are embedded or otherwise attached or connected with flexible polymer 846. The segments (or elements) may be substantially solid, porous. The metallic elements may be arranged in a discontinuous fashion. The gaps may be strategically placed, with specific sizes and orientations, or they may be randomly placed. The entire device may as a whole flex and in turn, minimize the stress placed on each individual structure. The gradient polymer may be stretched or deformed (e.g. to change its spatial conformation or spatial configuration), while the individual metal components move relative to one another. The exact movement may depend on how the polymer is deformed and the orientation and structure of the metal segments. Metal-free gaps (or spaces) may be strategically placed. The gaps may be chosen to allow a predetermined location and direction for a metal to expand or collapse. Gaps and metal composition may be different for different purposes. In response to a stimulus, such as being stretched (e.g. by hand, heat, placement on a joint surface) the polymer stretches to accommodate to a new shape. After placement in the joint, the polymer may return to its original or a preferred shape and size.

Figure 27:
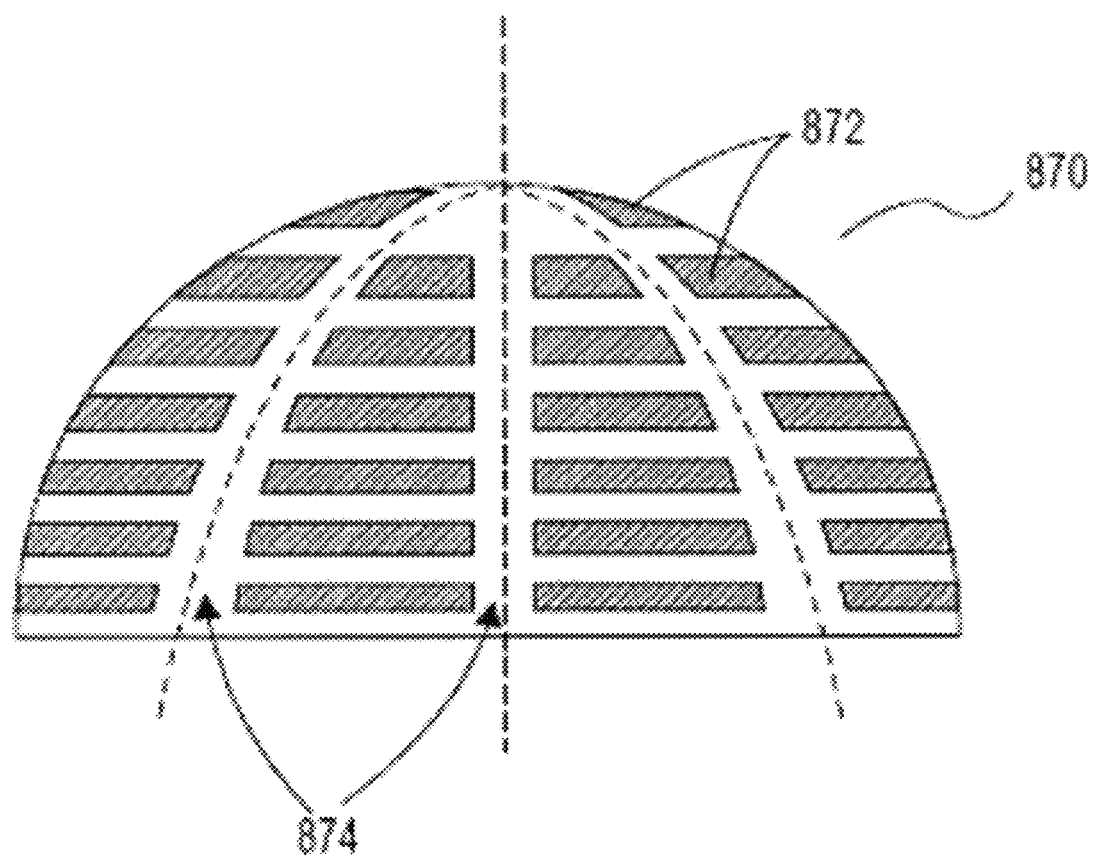
FIG. 27 shows another embodiment of an orthopedic implant with metal segments for placement in a joint.

FIG. 27 shows an acetabular component 870 with a segmented metal backing having a plurality of segments 872 attached to or embedded with a polymer member. Segments are discontinuous with slots or gaps 874 between segments to allow the implant to collapse, expand, or otherwise change its shape. The gaps in the figure are exaggerated to show how the polymer may stretch. The implant is able to flex and bend due to the gaps between the metal segments without putting undue stress or strain on the metal components themselves. The metal segments may be continuous or may have holes, pores, or slots. The implant or metal may transiently bend during placement in a body or in a joint. The metal may provide a bone contact surface for attaching to a bone. The metal may allow bone ingrowth. There may also be embodiments where there are no discontinuities, gaps, or slots, such that the metal component is continuous in all directions, and instead has a series of grooves on the interior wall and an optional central stem such that the femoral head must be prepared by chamfering and drilling to fit the bone inside the metal component.

In one aspect, a method of inserting an implant in a joint of a body may include inserting a polymer-metal implant into a joint space and changing a shape of the implant from a first shape to a second shape to conform to a shape of at least a portion of a bone forming the joint. The method may include returning the implant back to the first shape. The method may also include deforming the implant prior to the changing step from an original shape to a first shape. This may be useful, for example, to place the implant in the joint (e.g. through arthroscopic or minimally invasive surgery). For an implant configured to be placed on a femoral head of a hip joint, deforming may include expanding at least a portion of the implant to fit over the femoral head.

The various embodiments of the present disclosure are applicable to any joint in the body, including but not limited to the hand, feet, digits (of the hands and feet), ankle, intervertebral discs (cervical, thoracic, lumbar, or sacral), intervertebral facets, hip, knee, shoulder, and temporomandibular joint. The devices may be used with an acromioclavicular joint, ankle joint, condyle, elbow joint, a hand joint including a metacarpal joint, a finger joint, a thumb joint, a base of thumb joint, a glenoid, a hip joint including an acetabular joint, an intervertebral disc, a vertebral joint, including an intervertebral facet joint, a labrum, a meniscus, a foot joint, including a metatarsal joint and a toe joint, a patella, a tibial plateau, a jaw joint including a temporomandibular joint, a knee joint including a knee medial compartment joint, a patellofemoral joint, and a total knee joint, a knee meniscus, a shoulder joint including a labral joint, or a wrist joint and any portion thereof.

Any of the devices, features, materials, or methods described herein may be combined with any other devices, feature, material or method.

Figure 28:
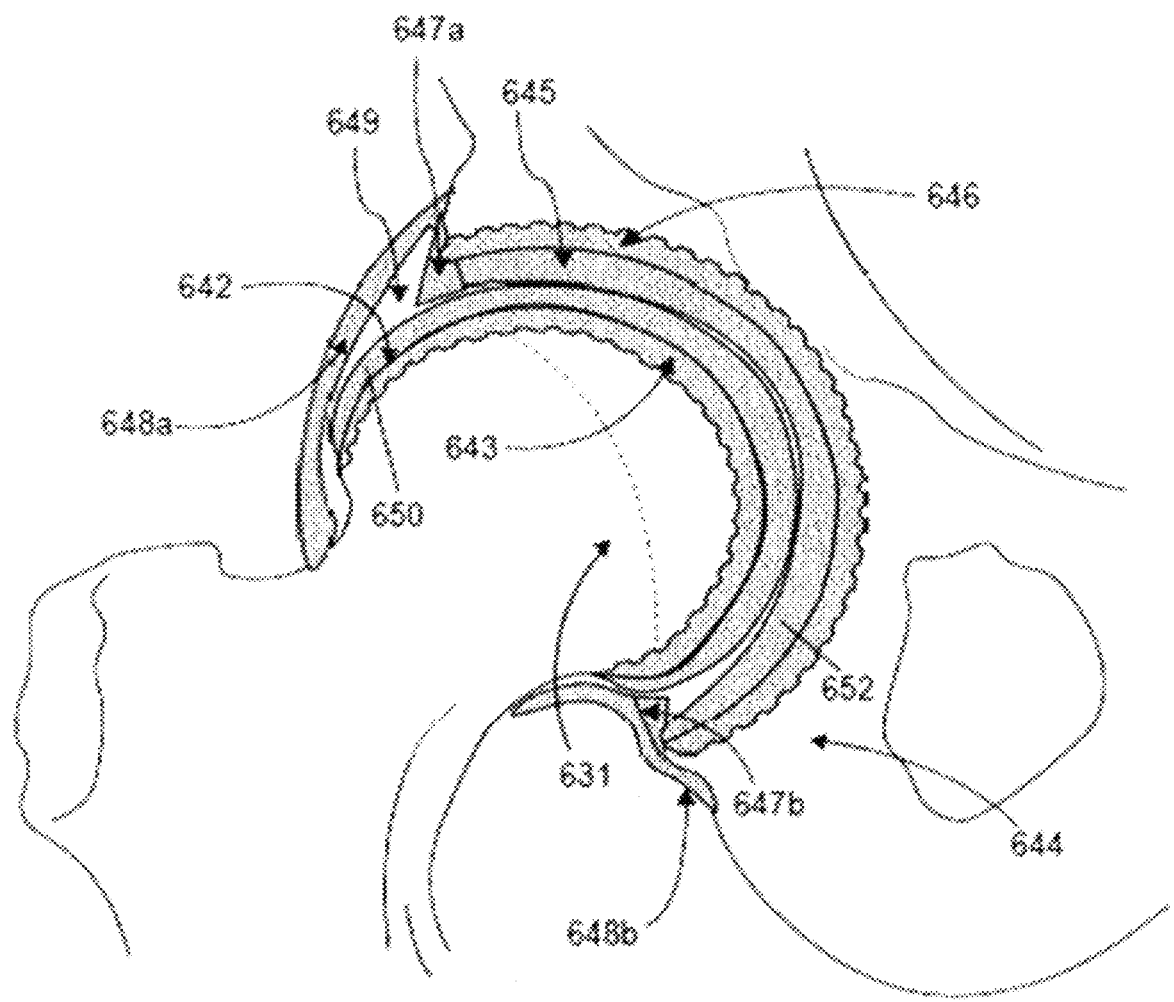
FIG. 28 shows a total cartilage replacement system, with cap-on-cup cartilage replacement implants, a synthetic joint capsule component, labral components, and lubricant fluid in accordance with some embodiments.

FIG. 28 shows a total hip cartilage and joint replacement system with gradient polymer metal alloy cap-on-cup implants according to one aspect of the disclosure. Both sides of the joint as well as labral and capsule components are replaced. The system may include femoral implant 650 and acetabular component 652. The bearing surfaces of the polymers on the two sides of the joint are configured to mate to provide a smooth, lubricious artificial joint interface. Lubricous IPN polymer 642 and lubricious IPN polymer 645 are respectively attached to metal bone interfacing members 646, 643 with porous metal backings which are in turn attached to femur 631 and acetabulum 644. The total replacement system may further include an artificial labral component shown in superior cross section 647a and inferior cross section 647b which may enclose lubricant 649. The system may also include an artificial capsule as shown in superior cross section 648a and inferior cross section 648b capsule components. A labral or capsule component may be made of any strong material with a smooth surface to provide support, stability, and/or lubriciousness to a joint. A labral or capsule component may be made from any of the IPNs or semi-IPNs described or referenced herein.

Figure 29:
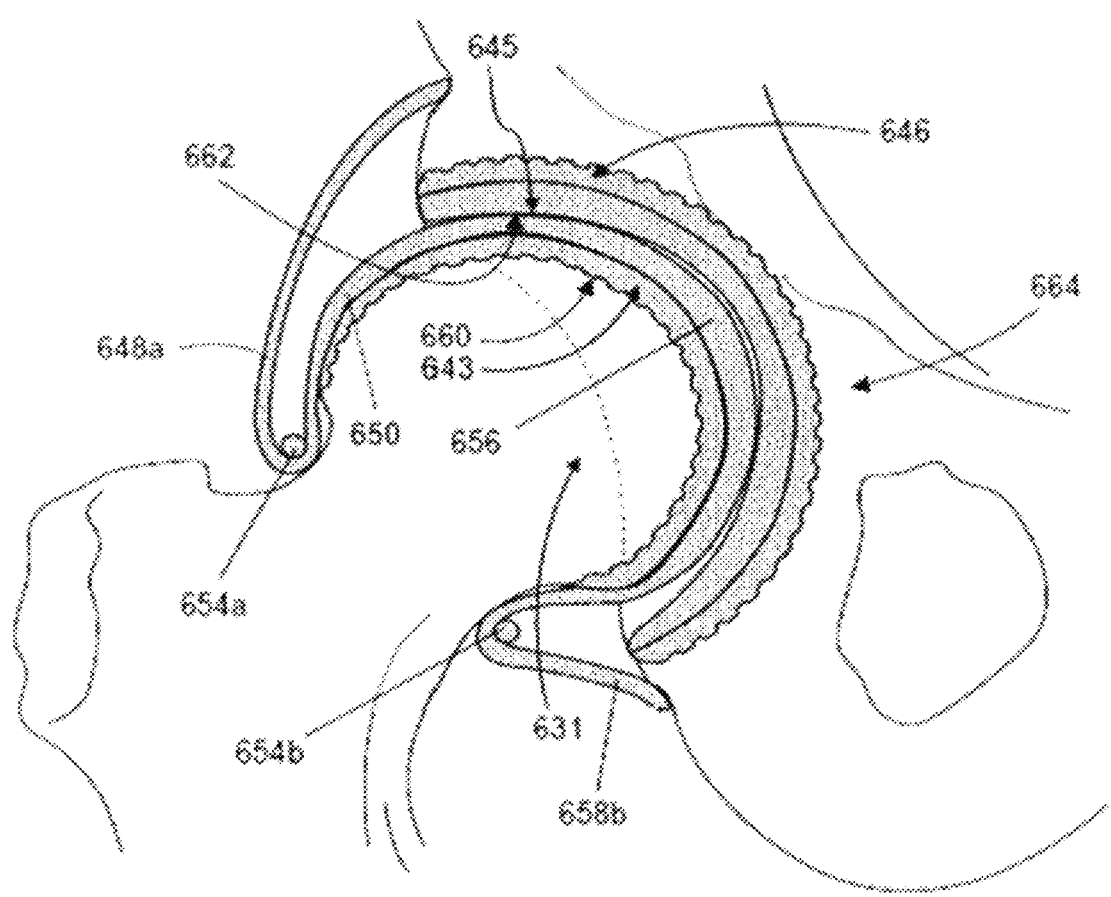
FIG. 29 shows an integrated joint and joint capsule replacement system in accordance with some embodiments.

FIG. 29 shows another embodiment of a hip total cartilage replacement system with an acetabular implant similar to the one described in FIG. 29 and with an integrated labral/femoral device. Femoral replacement implant 662 includes a femoral contacting portion and a labral replacement portion shown in superior cross section 648a and inferior cross section 619b continuous with the femoral contacting portion 650 and extending proximally toward the acetabular rim. The system may include an acetabular component. The bearing surfaces of the polymers on the femoral and acetabular side are configured to mate to provide a smooth, lubricious artificial joint interface. The devices may be attached to metal bone interfacing members 646, 643 with porous metal backings which are in turn attached to femur 631 and acetabulum 644. Features 660 may aid the implant in attaching to a bone. Features may be any structure that aid in placing or attaching an implant into a joint, such as cones, depressions, grooves, pegs, pillars, pins, and pyramids. An implant may have one feature or may have many (2-5, up to 10, up to 100, up to a 1000, or more) features. A feature(s) may be present on a bone contact surface of a metal or other bone interface member to aid in attaching an implant (e.g. a metal implant) to a bone. A feature(s) may be present on a surface or zone of a bone interface member that attaches to an attachment zone of an IPN or semi-IPN. The labral implant or portion of a labral implant may be fixed to bone through any means (e.g. screws, bone anchors, sutures, and/or welded polymer rivets). Superior 654a and inferior 654b collar sections are also shown in cross section. A collar may provide support or otherwise maintain a labral portion in a desired position. A collar may cinch over a labral portion. The ends of the labral portions may also (or instead) be continuous with an acetabular portion (not shown in this view).

Any of the implants described herein may be configured to correct large or small cartilage defects.

EXAMPLES

The following are some exemplary embodiments of processes used to synthesize sulfonated IPNs according to the present disclosure.

Example 1

Polyether urethane sheets (2 mm thick) were soaked in the following solution: 10% acrylic acid (AA) mixed with a non-ionizable (charge neutral) monomer solution, 5000 ppm Bisacrylamide Crosslinker, and 1000 ppm 2-hydroxy-2-methylpropiophenone photoinitiator at 60 C for 12 h. Any of the non-ionizable (charge neutral) monomers disclosed herein can be used. The samples were then photocured in a UV oven for 10 minutes. They were then soaked in the following solution: 40% AMPS in H2O, 5000 ppm Bisacrylamide Crosslinker and 1000 ppm 2-hydroxy-2-methylpropiophenone photoinitiator at 37 C for 12 h. Samples were then photocured in a UV oven for 10 minutes. The samples were then washed in saline and neutralized using an NaOH titrator.

Example 2

Polyether urethane sheets (2 mm thick) were soaked in the following solution: mixed with a non-ionizable (charge neutral) monomer solution, 5000 ppm Bisacrylamide Crosslinker and 1000 ppm 2-hydroxy-2-methylpropiophenone photoinitiator at 60 C for 12 h. Samples were then photocured in a UV oven for 10 minutes. Any of the non-ionizable (charge neutral) monomers disclosed herein can be used. They were then soaked in the following solution: 40% AMPS in H2O+5000 ppm Bisacrylamide Crosslinker and 1000 ppm 2-hydroxy-2-methylpropiophenone photoinitiator at 37 C for 12 h. They were then placed between glasses and photocure in UV oven for 10 minutes. The samples were then washed in saline and neutralized using an NaOH titrator.

Example 3

Polyether urethane sheets (2 mm thick) were soaked in the following solution: a non-ionizable (charge neutral) monomer solution, 5000 ppm Bisacrylamide Crosslinker and 1000 ppm 2-hydroxy-2-methylpropiophenone photoinitiator at 60 C for 12 h. Any of the non-ionizable (charge neutral) monomers disclosed herein can be used. They were then photocured in a UV oven for 10 minutes. They were then soaked in the following solution: 40% AMPS 10% AA 50% H2O (w/w)+5000 ppm Bisacrylamide Crosslinker and 1000 ppm 2-hydroxy-2-methylpropiophenone photoinitiator at 37 C for 12 h. They were then photocured in a UV oven for 10 minutes. The samples were then washed in saline and neutralized using an NaOH titrator.

Example 4

A wide range of triple IPN network formulations were synthesized that include PEU in the first network, PVP in the second network, and PAMPS in the third network.

Polyether urethane (PEU) sheets (2 mm thick) were submerged in a solution of N-vinylpyrrolidone (NVP) and water (65:35) containing 2000 ppm of N-N'-Methylenebis (acrylamide) and 2000 ppm of 2-Hydroxy-2-methylpropiophenone. The specimens were soaked at 37° C. for 3 days with gentle agitation. After NVP-water soaking, the specimens were photopolymerized under ultraviolet irradiation for 400 seconds to form the secondary network of PVP. The PEU-PVP specimens were washed in a bath of deionized water at 37° C. for 3 days. The washed PEU-PVP specimens were then submerged in 2-Acrylamido-2-methylpropane sulfonic acid (AMPS)-water solution (50:50) containing 2000 ppm of N-N'-Methylenebis(acrylamide) and 2000 ppm of 2-Hydroxy-2-methylpropiophenone. The specimens were soaked at 37° C. for 3 days using gentle agitation. After the AMPS-water soaking step, the specimens were polymerized under ultraviolet irradiation for 400 seconds to form the tertiary network of PAMPS. The PEU-PVP-PAMPS specimens were washed in a bath of deionized water for 3 days at 37° C. Finally, the specimens were fully neutralized using NaOH to yield the final IPN polymer PEU-PVP-NaPAMPS.

Figure 5A:
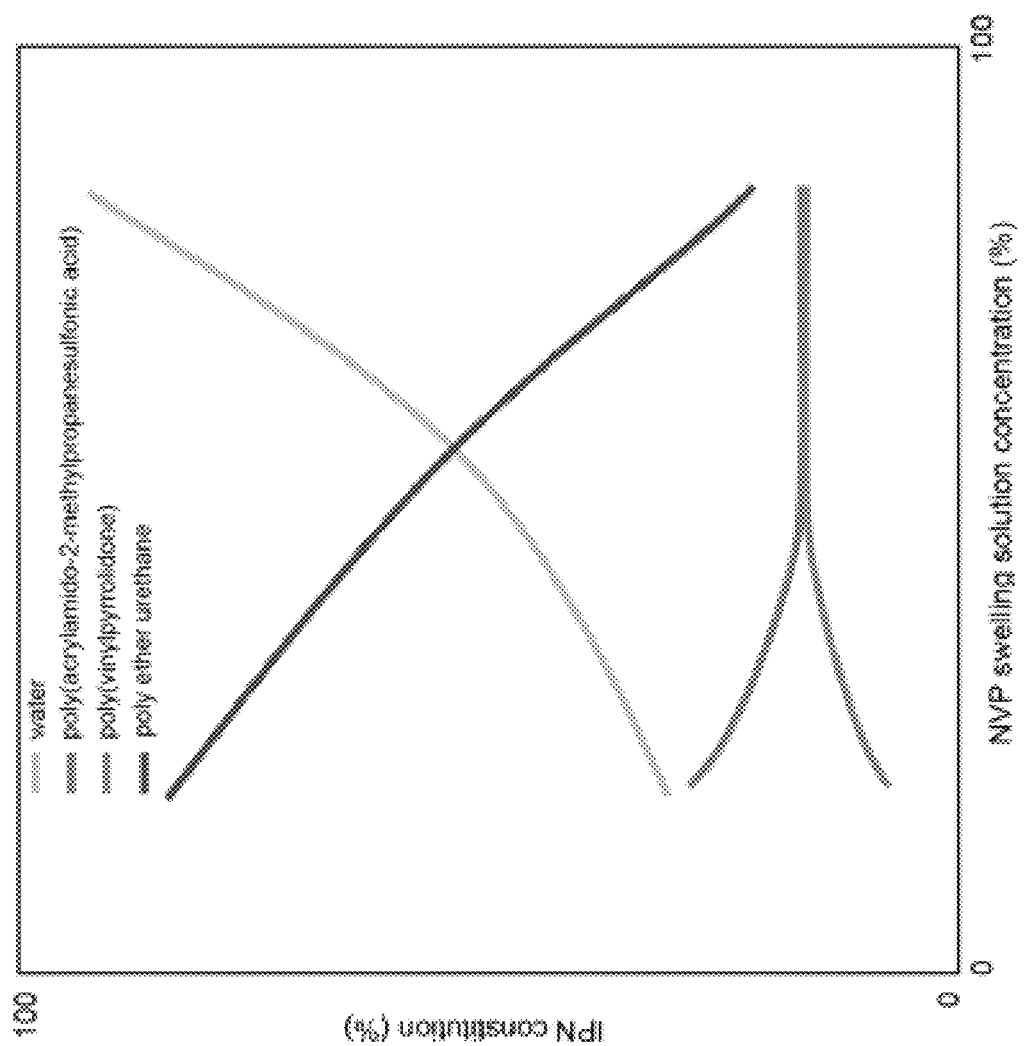
FIG. 5A is a graph showing the NVP swelling solution concentration relative to the IPN constitution for different IPN components.

FIG. 5A depicts the relationship between the concentration of the NVP solution to swell the PEU network plotted against the percentage of constituents of the final triple network IPN containing PEU, PVP, and PAMPS. With increasing NVP concentration, the number of AMPS molecules of the tertiary network increase up to the point that the two polymers, poly(AMPS) and PVP, have equimolar concentrations. The water content of the triple network rises dramatically with increased NVP incorporation into the PEU, while the polymer content of PEU decreases. Of note, at lower NVP concentrations, there is a higher proportion of PVP incorporated into the triple IPN compared to NVP. The water content values here range from about 19% to about 66%, while the PEU content ranges from about 13% to about 50%.

Figure 5B:
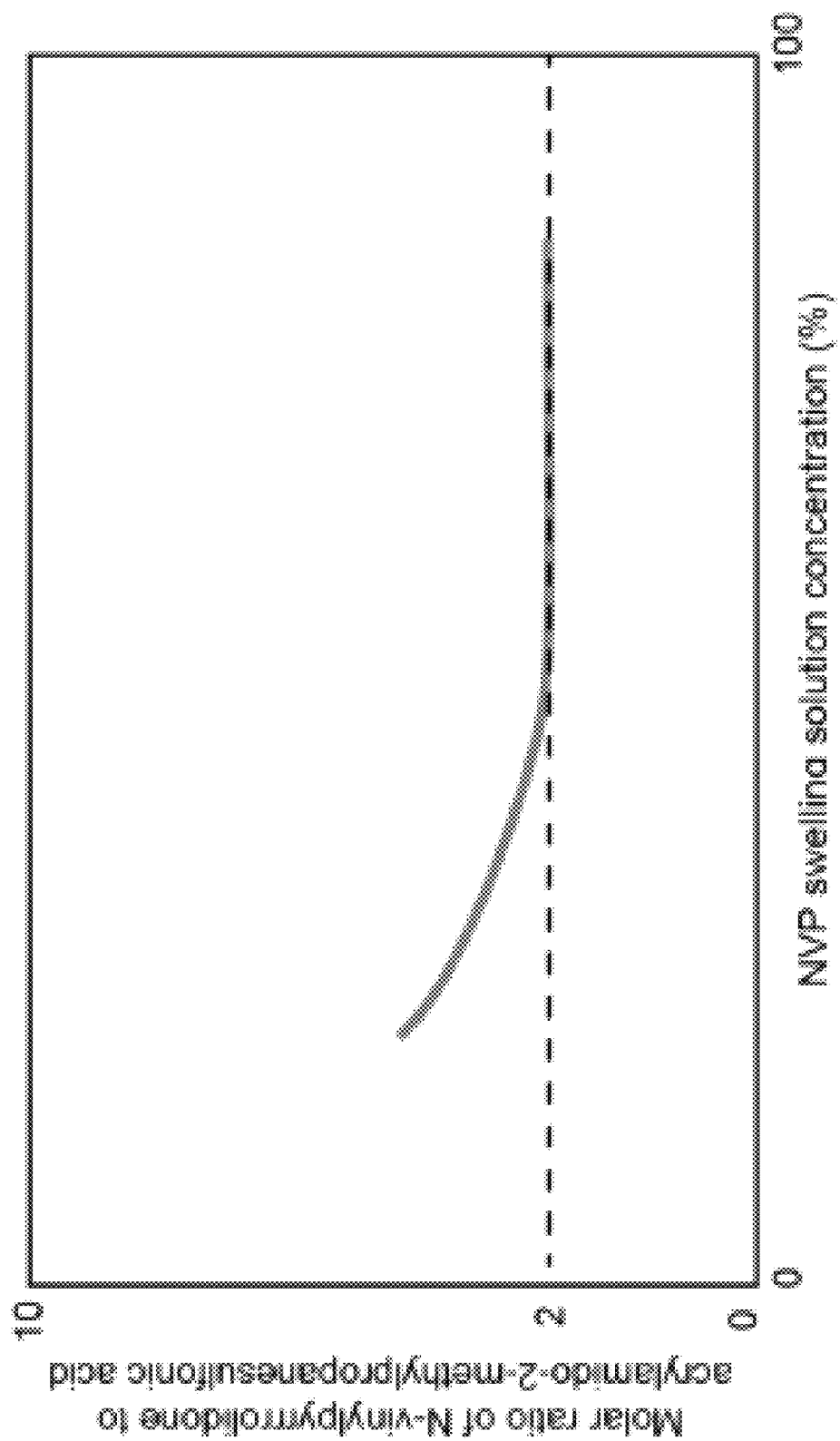
FIG. 5B is a graph showing the NVP swelling solution concentration relative to the molar ratio of NVP to AMPS.

In some embodiments, a triple IPN network formulation can be chosen, for example for use as part of an orthopedic implant, that maximizes the concentration of AMPS while minimizing the concentration of NVP. FIG. 5B demonstrates that the molar ratio of NVP molecules over AMPS decreases with increasing concentration of NVP until it reaches the plateau of about 2.

Figure 5C:
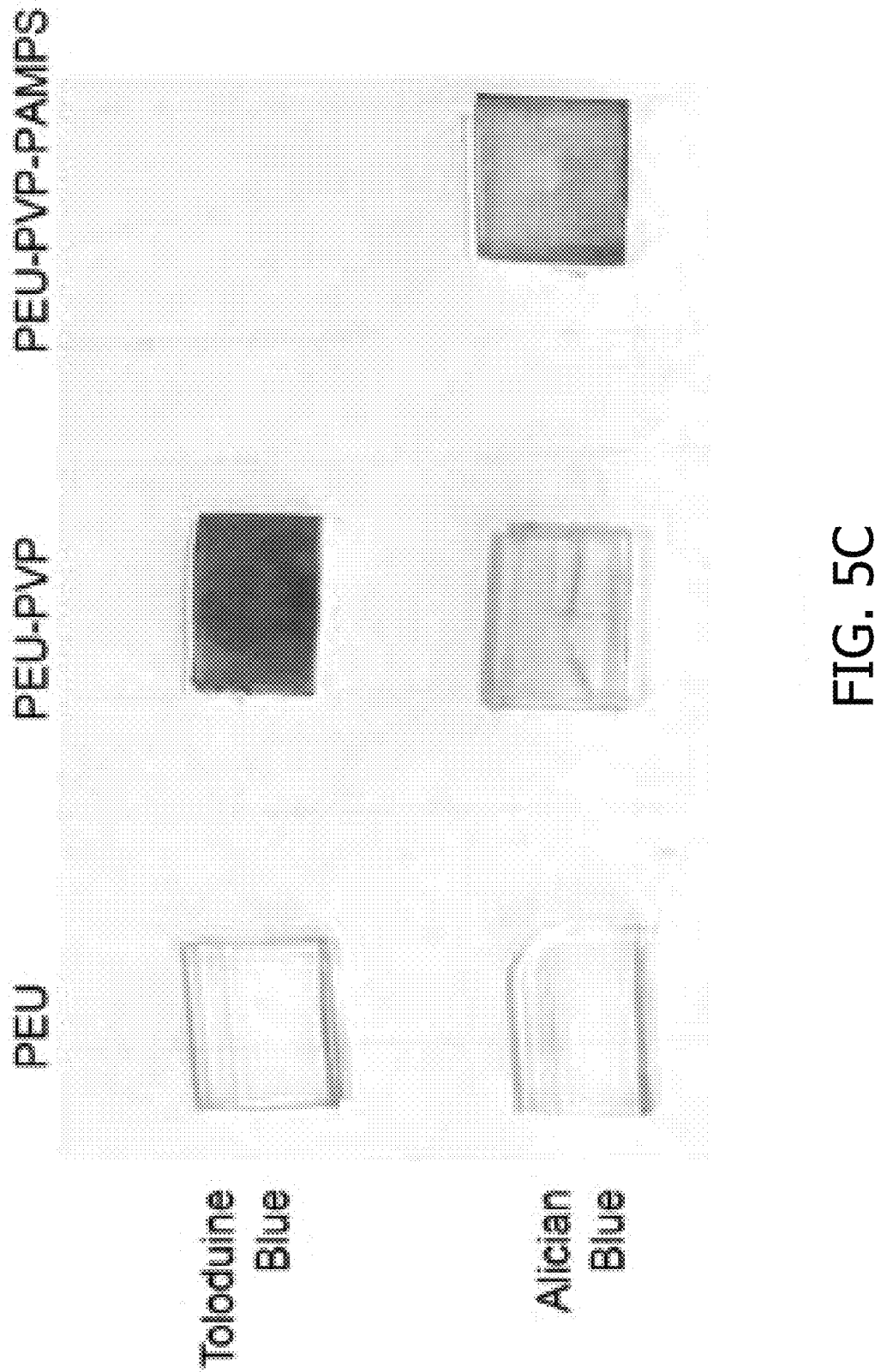
FIG. 5C shows the staining of various polymer networks to identify the presence or absence of PAMPS in the triple network.

FIG. 5C depicts the staining of various polymer networks to identify the presence or absence of PAMPS in the triple IPN. Toluidine blue stains the secondary network of NVP. Alician Blue, which is widely used to stain charged sulfated proteoglycans, stains only the poly(AMPS) network, and does not stain the PEU-PVP two-network IPN. This experiment shows that PVP can act advantageously act as an intermediary network to facilitate the incorporation of AMPS into a PEU-based IPN.

Example 5

A range of triple IPN formulations were synthesized using PEU in the first network, polymerized dimethylacrylamide (poly-DMAA) in the second network, and PAMPS in the third network.

Polyether urethane (PEU) sheets (2 mm thick) were submerged in a solution of N,N-dimethylacrylamide (DMAA) and water (75:25) containing 2000 ppm of N-N'-Methylenebis(acrylamide) and 2000 ppm of 2-Hydroxy-2-methylpropiophenone. The specimens were soaked at 60° C. for 3 days with gentle agitation. After NVP-water soaking, specimens were photopolymerized under ultraviolet irradiation for 400 seconds to form the secondary network of pDMAA. The PEU-pDMAA specimens were washed in a bath of deionized water at 37° C. for 3 days. The washed PEU-pDMAA specimens were submerged in 2-Acrylamido-2-methylpropane sulfonic acid (AMPS)-water solution (50:50) containing 2000 ppm of N-N'-Methylenebis(acrylamide) and 2000 ppm of 2-Hydroxy-2-methylpropiophenone. The specimens were soaked at 37° C. for 3 days with gentle agitation. After AMPS-water soaking, the specimens were polymerized under ultraviolet irradiation for 400 seconds to form the tertiary network of PAMPS. The polymerized specimens were washed in a bath of deionized water for 3 days at 37° C. Finally, the specimens were fully neutralized using NaOH to yield the final IPN polymer PEU-pDMAA-NaPAMPS.

In some resulting cases, PEU was swollen in 60% DMAA while in other cases PEU was swollen in 75% DMAA. In this set of experiments, the water content ranged from 13% to 52%, the PEU content ranged from 22%-72%, the poly-DMAA content ranged from 11%-16% and the PAMPS ranged from 1%-15% of the total IPN content, with an exemplary embodiment being comprised of 30% PEU, 16% polyDMAA, 10% PAMPS, and 44% water. In another embodiment, the IPN was comprised of 64% PEU, 13% polyDMAA, 5% PAMPS, and 19% water.

Example 6

PEU was used in the first network, co-polymerized dimethylacrylamide (DMAA) and AMPS were used in the second network, and PAMPS was used in the third network to form a sequential, co-polymeric IPN containing PAMPS in both the second network and third network.

Polyether urethane (PEU) sheets (2 mm thick) were submerged in a solution of N,N-dimethylacrylamide (DMAA), sodium 2-Acrylamido-2-methylpropane sulfonate (NaAMPS) and water (70:15:15) containing 3000 ppm of N-N'-Methylenebis(acrylamide), 1500 ppm of 2-Hydroxy-2-methylpropiophenone, and 75 ppm of hydroquinone. The specimens were soaked for 4 days at 60° C. using gentle agitation. After soaking, the specimens were photopolymerized under ultraviolet irradiation for 400 seconds to form the secondary copolymer network of poly(DMAA-NaAMPS). The specimens were then washed in a bath of deionized water at 37° C. for 3 days. The washed PEU-poly(DMAA-NaAMPS) specimens were submerged in a solution of sodium 2-Acrylamido-2-methylpropane sulfonate (NaAMPS) and water (50:50) containing 3000 ppm of N-N'-Methylenebis(acrylamide), 1500 ppm of 2-Hydroxy-2-methylpropiophenone and 300 ppm of hydroquinone. The specimens were soaked at 37° C. for 3 days using gentle agitation. After the NaAMPS-water soaking step, the specimens were polymerized under ultraviolet irradiation for 400 seconds to form the tertiary network of NaPAMPS. The polymerized specimens were washed in a bath of deionized water for 3 days at 37° C. giving rise to the final IPN polymer PEU-poly(DMAA-NaPAMPS)-NaPAMPS In some resulting cases, the relative concentrations by weight of the polymeric constituents were as follows: 19% PEU, 14% poly(DMAA-AMPS) co-polymer, 10% PAMPS homopolymer, and 57% water.

Example 7

PEU was used in the first network, co-polymerized N-vinyl pyrrolidone (NVP) and AMPS were used in the second network, and PAMPS was used in the third network to form a sequential, co-polymeric IPN containing PAMPS in both the second network and third network.

Polyether urethane (PEU) sheets (2 mm thick) were submerged in a solution of N of N-vinylpyrrolidone (NVP), sodium 2-Acrylamido-2-methylpropane sulfonate (NaAMPS) and water (62:19:19) containing 3000 ppm of N-N'-Methylenebis(acrylamide), 1500 ppm of 2-Hydroxy-2-methylpropiophenone and 300 ppm of hydroquinone. The specimens were soaked for 4 days at 60° C. using gentle agitation. After soaking, the specimens were photopolymerized under ultraviolet irradiation for 400 seconds to form the secondary copolymer network of poly(NVP-NaAMPS). The specimens were then washed in a bath of deionized water at 37° C. for 3 days. The washed PEU-poly(NVP-NaAMPS) specimens were submerged in a solution of sodium 2-Acrylamido-2-methylpropane sulfonate (NaAMPS) and water (50:50) containing 3000 ppm of N-N'-Methylenebis(acrylamide), 1500 ppm of 2-Hydroxy-2-methylpropiophenone, and 300 ppm of hydroquinone. The specimens were soaked at 37° C. for 3 days using gentle agitation. After NaAMPS-water soaking, the specimens were polymerized under ultraviolet irradiation for 400 seconds to form the tertiary network of NaPAMPS. The polymerized specimens were washed in a bath of deionized water for 3 days at 37° C. giving rise to the final IPN polymer PEU-poly(NVP-NaPAMPS)-NaPAMPS.

Figure 5D:
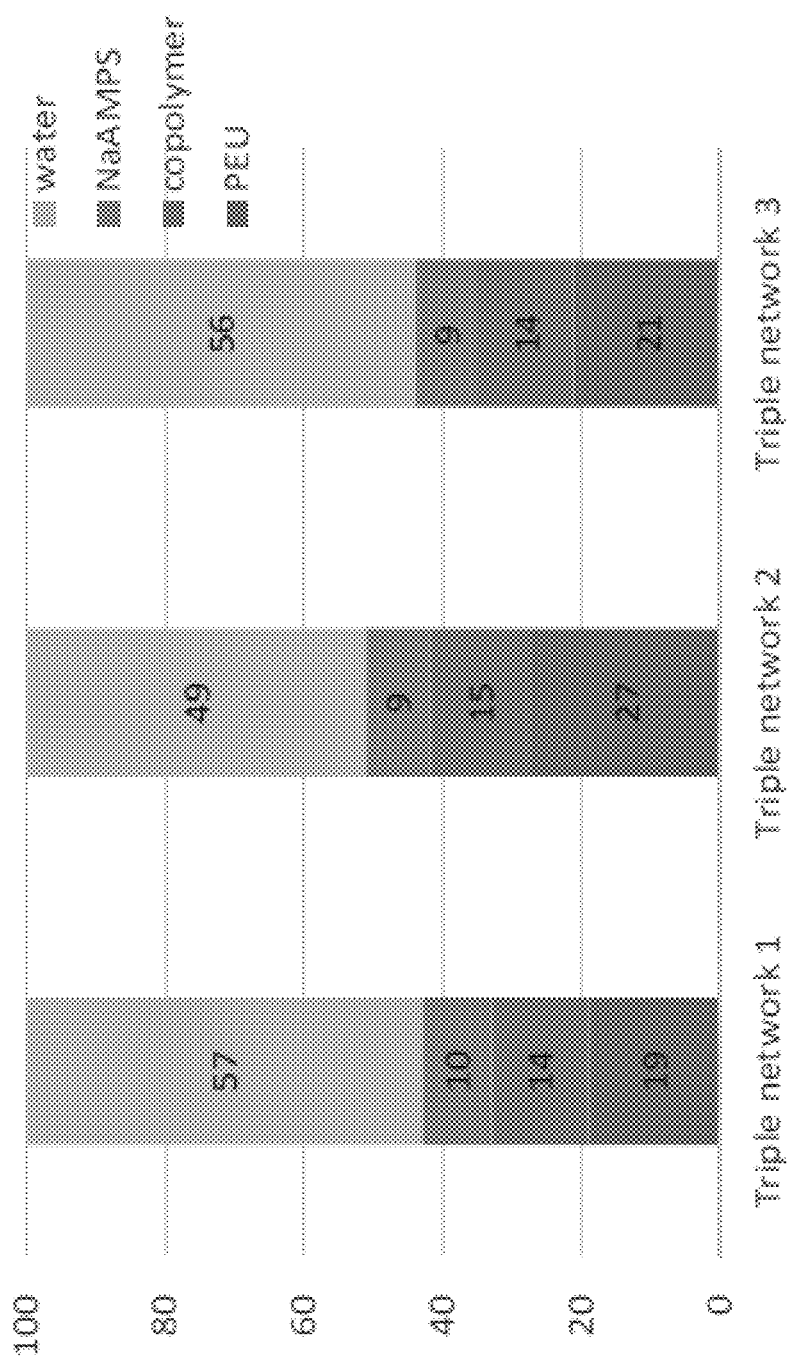
FIG. 5D shows exemplary compositional data of IPNs having as secondary network a co-polymer of either NVP and AMPS or DMAA and AMPS.

FIG. 5D shows exemplary compositional data from additional examples. In one example where a copolymer of NVP and NaAMPS (poly(co-(NVP-NaAMPS)) was synthesized, the relative concentrations by weight of the polymeric constituents were as follows: 19% PEU, 14% poly(NVP-NaAMPS) co-polymer, 10% PAMPS homopolymer, and 57% water. In the example where DMAA and NaAMPS were co-polymerized in the second network (poly(co-(DMAA-NaAMPS)), the relative concentrations by weight of polymeric constituents were as follows: 27% PEU, 15% poly(DMAA-NaAMPS) co-polymer, 9% PAMPS homopolymer, and 49% water, and in another example, it was 21% PEU, 14% poly(DMAA-NaAMPS) co-polymer, 9% PAMPS homopolymer, and 56% water.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Further embodiments of the present disclosure are described in the following enumerated aspects:

Aspect 1. An orthopedic implant comprising: a bone interface member having a bone contact surface; and a water swellable, water permeable interpenetrating polymer network (IPN) or semi-IPN member having a bearing surface and an attachment zone, the attachment zone being attached to the bone interface member, the water swellable IPN or semi-IPN member comprising a first polymer network comprising a hydrophobic thermoset or thermoplastic polymer, a second polymer network comprising a non-ionic polymer, and a third polymer network comprising an ionic polymer containing sulfonic acid functional groups, the water swellable, water permeable IPN or semi-IPN member including a compositional gradient between the bearing surface and the attachment zone.

Aspect 2. The implant of aspect 1, wherein the second network comprising the non-ionic polymer includes polymerized monomers comprising one or more of: dimethylacrylamide, acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide, and combinations thereof.

Aspect 3. The implant of aspect 2, wherein the second polymer network comprising the non-ionic polymer includes polymerized hydroxyethyl methacrylate.

Aspect 4. The implant of any of the preceding aspects, wherein the third polymer network comprising an ionic polymer containing sulfonic acid groups includes polymerized monomers comprising one or more of: 2-acrylamido 2-methyl propane sulfonic acid (AMPS), 2-Propene-1-sulfonic acid, 2-Methyl-2-propene-1-sulfonic acid, 1,3-Propanesulfone, 1,4 butane sulfone, vinyl sulfonic acid, anetholesulfonic acid, and styrenesulfonic acid.

Aspect 5. The implant of aspect 4, wherein the third polymer network comprising the ionic polymer containing sulfonic acid groups includes polymerized 2-acrylamido 2-methyl propane sulfonic acid (AMPS).

Aspect 6. The implant of aspect 4, wherein the third polymer network comprising the ionic polymer containing sulfonic acid groups includes polymerized acrylic acid and vinyl sulfonic acid.

Aspect 7. The implant of aspect 1, wherein the second polymer network comprising the non-ionic polymer includes polymerized hydroxyethyl methacrylate and the third polymer network comprising the ionic polymer containing sulfonic acid groups includes polymerized 2-acrylamido 2-methyl propane sulfonic acid (AMPS).

Aspect 8. The implant of any of the preceding aspects, wherein the third polymer network comprising the ionic polymer containing sulfonic acid groups includes polymerized 2-acrylamido 2-methyl propane sulfonic acid (AMPS) and acrylic acid.

Aspect 9. The implant of any of the preceding aspects, wherein the third polymer network comprising the ionic polymer containing sulfonic acid groups comprises about 1% to about 100% sulfonic acid groups relative to a total number of functional groups of the third polymer network.

Aspect 10. The composition of any of the preceding aspects, wherein the bearing surface has a coefficient of friction of less than about 0.1.

Aspect 11. The composition of any of the preceding aspects, wherein the bearing surface has a coefficient of friction of less than about 0.01.

Aspect 12. The composition of any of the preceding aspects, wherein the bearing surface has a coefficient of friction of less than about 0.005.

Aspect 13. The implant of any of the preceding aspects, wherein the compositional gradient forms a stiffness gradient.

Aspect 14. The implant of any of the preceding aspects, wherein one of the second and third polymer networks forms a composition and hydration gradient from a first portion of the implant to a second portion of the implant.

Aspect 15. The implant of any of the preceding aspects, wherein the bone interface member comprises a metal.

Aspect 16. The implant of aspect 15 wherein the metal comprises a porous metal.

Aspect 17. The implant of aspect 16, wherein the attachment zone is attached to the porous metal of the bone interface member with a bone cement.

Aspect 18. The implant of aspect 16, wherein the attachment zone is attached to the porous metal of the bone interface member through interdigitation.

Aspect 19. The implant of any of the preceding aspects, wherein the bone interface member comprises a ceramic or a polymer.

Aspect 20. The implant of any of the preceding aspects, wherein at least a portion of the orthopedic implant is configured to change a shape during implant placement in a joint.

Aspect 21. The implant of any of the preceding aspects, wherein at least a portion of the implant is configured to transiently deform during implant placement in a joint.

Aspect 22. The implant of any of the preceding aspects, wherein an attachment of the attachment zone to the bone interface member is created by an adhesive.

Aspect 23. The implant of any of the preceding aspects, wherein the third polymer network comprises a fixed charge.

Aspect 24. The implant of any of the proceeding aspects, wherein the ionic polymer comprises a majority of sulfonic groups relative to other functional groups.

Aspect 25. The implant of any of the preceding aspects, wherein the implant has a shape selected from the group consisting of: a cap, a cup, a plug, a mushroom, a cylinder, a patch, and a stem.

Aspect 26. The implant of any of the preceding aspects, wherein the implant is adapted to fit an acromioclavicular joint, an ankle joint, a condyle, an elbow joint, a hand joint including a metacarpal joint, a finger joint, a thumb joint, a base of thumb joint, a glenoid, a hip joint including an acetabular joint, an intervertebral disc, a vertebral joint, including an intervertebral facet joint, a labrum, a meniscus, a foot joint, including a metatarsal joint and a toe joint, a patella, a tibial plateau, a jaw joint including a temporomandibular joint, a knee joint including a knee medial compartment joint, a patellofemoral joint, and a total knee joint, a knee meniscus, a shoulder joint including a labral joint, or a wrist joint and any portion thereof.

Aspect 27. The implant of any of the preceding aspects, wherein the first polymer network comprises polyurethane.

Aspect 28. The implant of any of the preceding aspects, further comprising: an additive within the water swellable, water permeable IPN or semi-IPN member, the additive including one or more of: a steroid, anti-inflammatory agent, antioxidant, antibiotic, and anti-microbial agent.

Aspect 29. The implant of any of the preceding aspects, further comprising an adhesive gradient between the attachment zone and the bearing surface, the adhesive gradient having a highest concentration of adhesive at the attachment zone.

Aspect 30. The implant of aspect 29, wherein the adhesive gradient comprises a polymerized bone cement.

Aspect 31. The implant of aspect 29, wherein the adhesive gradient comprises a urethane dimethacrylate-methyl methacrylate copolymer comprising a plurality of first polymer regions based on urethane dimethacrylate and a plurality of second polymer regions based on methyl methacrylate.

Aspect 32. The implant of aspect 31, wherein the first polymer regions based on urethane dimethacrylate comprise about 60%-99% (w/w) of the copolymer and the second polymer regions based on methyl methacrylate comprise about 1%-40% (w/w) of the copolymer.

Aspect 33. The implant of aspect 31, wherein the first polymer regions based on urethane dimethacrylate comprise about 60%-80% (w/w) of the copolymer and the second polymer regions based on methyl methacrylate comprise from about 20%-40% (w/w) of the copolymer.

Aspect 34. The implant of aspect 31, wherein the first polymer regions based on urethane dimethacrylate comprise soft segments based on poly(tetramethyl) glycol, the soft segments having a molecular weight between about 100 Da and about 5000 Da.

Aspect 35. The implant of aspect 31, wherein the urethane dimethacrylate-methyl methacrylate copolymer defines a compressive modulus between about 30 MPa and about 2000 MPa.

Aspect 36. The implant of aspect 31, wherein the urethane dimethacrylate-methyl methacrylate copolymer defines a tensile modulus between about 30 MPa and 2000 MPa.

Aspect 37. The implant of aspect 31, wherein the urethane dimethacrylate-methyl methacrylate copolymer defines a failure strain between about 25% and about 200%.

Aspect 38. A composition comprising: a water swellable, water permeable interpenetrating polymer network (IPN) or semi-IPN member comprising a first polymer network comprising a hydrophobic thermoset or thermoplastic polymer, a second polymer network comprising a non-ionic polymer, and a third polymer network comprising an ionic polymer containing sulfonic acid functional groups, the water swellable, water permeable IPN or semi-IPN member including a compositional gradient between a first surface and a second surface.

Aspect 39. The composition of aspect 38, wherein the first surface includes a lubricious surface.

Aspect 40. The composition of aspect 39, wherein the lubricious surface has a coefficient of friction of less than about 0.1.

Aspect 41. The composition of aspect 39, wherein the lubricious surface has a coefficient of friction of less than about 0.01.

Aspect 42. The composition of aspect 39, wherein the lubricious surface has a coefficient of friction of less than about 0.005.

Aspect 43. The composition of any of aspects 38-42, wherein the second network comprising the non-ionic polymer includes polymerized monomers comprising one or more of: dimethylacrylamide, acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide, and combinations thereof.

Aspect 44. The composition of aspect 43, wherein the second polymer network comprising the non-ionic polymer includes polymerized hydroxyethyl methacrylate.

Aspect 45. The composition of any of aspects 38-42, wherein the third polymer network comprising an ionic polymer containing sulfonic acid groups includes polymerized monomers comprising one or more of: 2-acrylamido 2-methyl propane sulfonic acid (AMPS), 2-Propene-1-sulfonic acid, 2-Methyl-2-propene-1-sulfonic acid, 1,3-Propanesulfone, 1,4 butane sulfone, vinyl sulfonic acid, anetholesulfonic acid, and styrenesulfonic acid.

Aspect 46. The composition of aspect 45, wherein the third polymer network comprising the ionic polymer containing sulfonic acid groups includes polymerized 2-acrylamido 2-methyl propane sulfonic acid (AMPS).

Aspect 47. The composition of any of aspects 38-40, wherein the second polymer network comprising the non-ionic polymer includes polymerized hydroxyethyl methacrylate and the third polymer network comprising the ionic polymer containing sulfonic acid groups includes polymerized 2-acrylamido 2-methyl propane sulfonic acid (AMPS).

Aspect 48. The composition of any of aspects 38-47, wherein the third polymer network comprising the ionic polymer containing sulfonic acid groups includes polymerized 2-acrylamido 2-methyl propane sulfonic acid (AMPS) and acrylic acid.

Aspect 49. The composition of any of aspects 38-48, wherein the first polymer network comprises polyurethane.

Aspect 50. The composition of any of aspects 38-49, wherein the third polymer network comprising the ionic polymer containing sulfonic acid groups comprises about 1% to about 100% sulfonic acid groups relative to a total number of functional groups of the third polymer network.

Aspect 51. The composition of any of aspects 38-50, wherein the compositional gradient forms a stiffness gradient.

Aspect 52. The composition of any of aspects 38-51, wherein one of the second or third polymer networks forms a hydration gradient from a first portion of the implant to a second portion of the implant.

Aspect 53. The composition of any of aspects 38-52, adapted for use as a bearing.

Aspect 54. A method of forming an interpenetrating polymer network (IPN) in a polymer composition comprising: contacting the polymer composition comprising a first polymer network of a hydrophobic thermoset or thermoplastic polymer with a non-ionic monomer solution; polymerizing the non-ionic monomer to form a second polymer network comprising the polymerized non-ionic monomer in the polymer composition; contacting the polymer composition with a solution of an ionic monomer containing sulfonic acid functional groups; and polymerizing the ionic monomer to form a third polymer network comprising the polymerized ionic monomer in the polymer composition.

Aspect 55. The method of aspect 54, wherein the non-ionic monomer comprises one or more of: dimethylacrylamide, acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide, and combinations thereof.

Aspect 56. The method of any of aspects 54-55, wherein the non-ionic monomer comprises hydroxyethyl methacrylate.

Aspect 57. The method of any of aspects 54-56, wherein the ionic monomer containing sulfonic acid groups comprises one or more of: 2-acrylamido 2-methyl propane sulfonic acid (AMPS), vinyl sulfonic acid, anetholesulfonic acid, and styrenesulfonic acid.

Aspect 58. The method of any of aspects 54-57, wherein the ionic monomer containing sulfonic acid groups comprises polymerized 2-acrylamido 2-methyl propane sulfonic acid (AMPS).

Aspect 59. The method of any of aspects 54-58, wherein the non-ionic monomer includes hydroxyethyl methacrylate and the ionic monomer containing sulfonic acid groups includes 2-acrylamido 2-methyl propane sulfonic acid (AMPS).

Aspect 60. The method of any of aspects 54-59, wherein the ionic polymer containing sulfonic acid groups comprises 2-acrylamido 2-methyl propane sulfonic acid (AMPS) and acrylic acid.

Aspect 61. The method of any of aspects 54-60, wherein the polymerized ionic polymer containing sulfonic acid groups comprises about 1% to about 100% sulfonic acid groups relative to a total number of functional groups of the third polymer network.

Aspect 62. The method of any of aspects 54-61, wherein the first polymer network comprises polyurethane.

Aspect 63. The method of any of aspects 54-62, further comprising: providing a photo-initiator with the non-ionic monomer and polymerizing the photo-initiator with the non-ionic monomer to crosslink the second polymer network.

Aspect 64. The method of any of aspects 54-63, further comprising: providing a photo-initiator with the ionic monomer and polymerizing the photo-initiator with the ionic monomer to crosslink the third polymer network.

Aspect 65. The method of any of aspects 54-64, wherein the polymer composition includes a bearing surface and an attachment zone being adapted to be attached to a bone interface member having a bone contact surface.

Aspect 66. The method of aspect 65, further comprising: forming a compositional gradient between the bearing surface and the attachment zone.

Aspect 67. The method of aspect 66, wherein the compositional gradient forms a stiffness gradient.

Aspect 68. The method of aspect 66, wherein one of the second or third polymer networks forms a hydration gradient between the bearing surface and the attachment zone.

Aspect 69. The method of any of aspects 54-66, wherein the composition gradient includes an adhesive gradient, the adhesive gradient having a highest concentration of adhesive at the attachment zone.

Aspect 70. The method of aspect 69, wherein the adhesive gradient is formed by polymerizing a bone cement within the polymer composition.

Aspect 71. The method of aspect 70, wherein the adhesive gradient comprises a urethane dimethacrylate-methyl methacrylate copolymer comprising a plurality of first polymer regions based on urethane dimethacrylate and a plurality of second polymer regions based on methyl methacrylate.

Aspect 72. The method of any of aspects 65-71, wherein the bone interface member comprises a metal.

Aspect 73. The method of aspect 72, wherein the metal comprises a porous metal.

Aspect 74. The method of any of aspects 65-73, wherein the bone interface member comprises a ceramic or a polymer.

Aspect 75. The method of any of aspects 65-74, further comprising: creating an attachment of the attachment zone to the bone interface member using an adhesive.

Aspect 76. The method of any of aspects 54-75, further comprising: shaping or forming the polymer composition to a desired shape.

Aspect 77. The method of aspect 76, wherein the desired shape is selected from the group consisting of: a cap, a cup, a plug, a mushroom, a cylinder, a patch, and a stem.

Aspect 78. The method of aspect 76, wherein the desired shape is adapted to fit an acromioclavicular joint, an ankle joint, a condyle, an elbow joint, a hand joint including a metacarpal joint, a finger joint, a thumb joint, a base of thumb joint, a glenoid, a hip joint including an acetabular joint, an intervertebral disc, a vertebral joint, including an intervertebral facet joint, a labrum, a meniscus, a foot joint, including a metatarsal joint and a toe joint, a patella, a tibial plateau, a jaw joint including a temporomandibular joint, a knee joint including a knee medial compartment joint, a patellofemoral joint, and a total knee joint, a knee meniscus, a shoulder joint including a labial joint, or a wrist joint and any portion thereof.

Aspect 79. The method of any of aspects 54-78, further comprising: adding an additive to the polymer composition, the additive comprising: one or more of: a steroid, anti-inflammatory agent, antioxidant, antibiotic, and anti-microbial agent.

Aspect 80. A system comprising: an orthopedic implant according to any of the aspects 1-37; and an adhesive kit.

Aspect 81. The system of aspect 80, wherein the adhesive kit comprises: a first reservoir comprising a first mixture comprising at least one of a urethane dimethacrylate monomer and a methyl methacrylate monomer; at least one of a photoinitiator and a thermal initiator; and an inhibitor; a second reservoir comprising a second mixture comprising at least one of a urethane dimethacrylate monomer and a methyl methacrylate monomer; and an accelerator; and an instruction for use; wherein at least one of the first reservoir and the second reservoir comprises a urethane dimethacrylate monomer and at least one of the first reservoir and the second reservoir comprises a methyl methacrylate monomer.

Aspect 82. The system of aspect 81, wherein both the first reservoir and the second reservoir comprise a urethane dimethacrylate monomer and a methyl methacrylate monomer.

Aspect 83. The system of any of aspects 81-82, wherein the second reservoir further comprises an inhibitor.

Aspect 84. The system of any of aspects 81-83, further comprising poly(methyl methacrylate).

Aspect 85. The system of any of aspects 81-84, further comprising a third reservoir comprising a poly(methyl methacrylate) powder.

Aspect 86. The system of any of aspects 81-85, wherein the first mixture, the second mixture and the poly(methyl methacrylate) define a component weight, and a weight of the poly(methyl methacrylate) powder comprises from about 1% to about 70% of the component weight.

Aspect 87. The system of any of aspects 81-86, further comprising a polystyrene.

Aspect 88. The system of any of aspects 81-87, further comprising a photoinitiator and a thermal initiator.

Aspect 89. The system of any of aspects 81-88, wherein the first reservoir comprises a first chamber in a syringe and the second reservoir comprises a second chamber in the syringe, wherein the syringe is configured to combine the first mixture with the second mixture to create an adhesive mixture.

Aspect 90. The system of aspect 89, further comprising a nozzle connected with the syringe configured to dispense the adhesive mixture.

Aspect 91. The system of any of aspects 81-90, wherein the first reservoir and the second reservoir each comprise from about 60% (w/w) to about 80% (w/w) urethane dimethacrylate monomer.

Aspect 92. The system of any of aspects 81-91, wherein the first reservoir and the second reservoir each comprise from about 20% (w/w) to about 40% (w/w) methyl methacrylate.

Aspect 93. The system of any of aspects 81-92, wherein the at least one initiator comprises a photoinitiator comprising between 0% (w/w) and about 1% (w/w) camphorquinone.

Aspect 94. The system of any of aspects 81-93, wherein the at least one initiator comprises a thermal initiator comprising between 0% (w/w) and about 1% (w/w) benzoyl peroxide.

Aspect 95. The system of any of aspects 81-94, wherein the accelerator comprises between 0% (w/w) and about 1% (w/w) N,N-dimethyl-p-toluidine.

Aspect 96. The system of any of aspects 81-95, wherein the inhibitor comprises between 0% (w/w) and about 0.1% (w/w) hydroquinone.

Aspect 97. The system of any of aspects 81-96, further comprising an additive configured to prevent an infection.

Aspect 98. The system of any of aspects 81-97, further comprising an antibiotic.

Aspect 99. The system of any of aspects 81-98, further comprising a radiopaque material.

Aspect 100. The system of any of aspects 81-99, wherein the first mixture defines a viscosity between about 1 Pa·S and 5000 Pa·S.

Aspect 101. A method of attaching an orthopedic implant within a human body comprising: providing a water swellable, water permeable interpenetrating polymer network (IPN) or semi-IPN member having a bearing surface and an attachment zone, the water swellable IPN or semi-IPN member comprising a first polymer network comprising a hydrophobic thermoset or thermoplastic polymer, a second polymer network comprising a non-ionic polymer, and a third polymer network comprising an ionic polymer containing sulfonic acid functional groups; providing a bone cement composition to the attachment zone; and curing the bone cement composition to attach the attachment zone to a surface of a bone or a portion of an orthopedic implant engaged with a surface of a bone within the human body.

Aspect 102. The method of aspect 101, wherein the second network comprising the non-ionic polymer includes polymerized monomers comprising one or more of: dimethylacrylamide, acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide, and combinations thereof.

Aspect 103. The method of aspect 101, wherein the second polymer network comprising the non-ionic polymer includes polymerized hydroxyethyl methacrylate.

Aspect 104. The method of any of aspects 101-103, wherein the third polymer network comprising an ionic polymer containing sulfonic acid groups includes polymerized monomers comprising one or more of: 2-acrylamido 2-methyl propane sulfonic acid (AMPS), vinyl sulfonic acid, anetholesulfonic acid, and styrenesulfonic acid.

Aspect 105. The method of any of aspects 101-104, wherein the third polymer network comprising the ionic polymer containing sulfonic acid groups includes polymerized 2-acrylamido 2-methyl propane sulfonic acid (AMPS).

Aspect 106. The method of any of aspects 101-105, further comprising: forming an adhesive gradient between the attachment zone and the bearing surface, the adhesive gradient having a highest concentration of adhesive at the attachment zone when curing the bone cement.

Aspect 107. The method of any of aspects 101-106, wherein curing the bone cement composition is performed by providing a light source to the bone cement composition.

Aspect 108. The method of any of aspects 106-107, wherein the adhesive gradient comprises a urethane dimethacrylate-methyl methacrylate copolymer comprising a plurality of first polymer regions based on urethane dimethacrylate and a plurality of second polymer regions based on methyl methacrylate.

Aspect 109. The method of aspect 108, wherein the first polymer regions based on urethane dimethacrylate comprise about 60%-99% (w/w) of the copolymer and the second polymer regions based on methyl methacrylate comprise about 1%-40% (w/w) of the copolymer.

Aspect 110. The method of aspect 108, wherein the first polymer regions based on urethane dimethacrylate comprise about 60%-80% (w/w) of the copolymer and the second polymer regions based on methyl methacrylate comprise from about 20%-40% (w/w) of the copolymer.

Aspect 111. The method of aspect 108, wherein the first polymer regions based on urethane dimethacrylate comprise soft segments based on poly(tetramethyl) glycol, the soft segments having a molecular weight between about 100 Da and about 5000 Da.

Aspect 112. The method of aspect 108, wherein the urethane dimethacrylate-methyl methacrylate copolymer defines a compressive modulus between about 30 MPa and about 2000 MPa.

Aspect 113. The method of aspect 108, wherein the urethane dimethacrylate-methyl methacrylate copolymer defines a tensile modulus between about 30 MPa and 2000 MPa.

Aspect 114. The method of aspect 108, wherein the urethane dimethacrylate-methyl methacrylate copolymer defines a failure strain between about 25% and about 200%.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An interpenetrating polymer network (IPN) or semi-IPN member comprising a first polymer network including a hydrophobic thermoset or thermoplastic polymer including multiple subsets of polymer segments, a second polymer network comprising a polymerized non-ionic monomer, and a third polymer network including an ionic polymer containing sulfonic acid groups, wherein the second network is non-ionic, the third network is ionic, the second and third polymer networks are each formed within the same subset of polymer segments of the hydrophobic thermoset or thermoplastic polymer, and the first, second, and third polymer networks are not bonded to each other covalently.

2. The IPN or semi-IPN member of claim 1, wherein the IPN or semi-IPN member comprises a lubricious surface having a coefficient of friction of less than about 0.1.

3. The IPN or semi-IPN member of claim 1, wherein the first polymer network comprises a polyurethane.

4. The IPN or semi-IPN member of claim 1, wherein the second polymer network comprises one or more polymerized non-ionic monomers selected from dimethylacrylamide (DMAA), acrylamide, N-isopropyl acrylamide (NIPAAm), hydroxyethyl acrylate, hydroxyethyl methacrylate, vinyl alcohol, methyl acrylate, hydroxyethyl acrylamide, hydroxyethyl methacrylamide, and N-vinyl pyrrolidone.

5. The IPN or semi-IPN member of claim 1, wherein the second polymer network comprises a plurality of different monomers.

6. The IPN or semi-IPN member of claim 1, wherein the ionic polymer containing sulfonic acid groups comprises a polymerized monomer having sulfonic acid functional groups.

7. The IPN or semi-IPN member of claim 1, wherein the ionic polymer containing sulfonic acid groups comprises a polymerized macromer having sulfonic acid functional groups.

8. The IPN or semi-IPN member of claim 1, wherein the ionic polymer containing sulfonic acid groups comprises a polymerized sulfonate-containing monomer selected from acrylamide methyl propane sulfonic acid (AMPS), 2-Propene-1-sulfonic acid, 1,3-Propanesulfone, 1,4 butane sulfone, anetholesulfonic acid, styrenesulfonic acid, vinyl sulfonic acid, 3-sulfopropyl acrylate, 3-sulfopropyl methacrylate, or 2-methyl-2-propene-1-sulfonic acid.

9. The IPN or semi-IPN member of claim 1, wherein the second polymer network, the third polymer network, or both is polymerized in the presence of a cross-linker.

10. The IPN or semi-IPN member of claim 9, wherein the cross-linker is selected from ethylene glycol dimethacrylate, ethylene glycol diacrylate, diethylene glycol dimethacrylate (or diacrylate), triethylene glycol dimethacrylate (or diacrylate), tetraethylene glycol dimethacrylate (or diacrylate), polyethylene glycol dimethacrylate, or polyethylene glycol diacrylate, methylene bisacrylamide, N,N'-(1,2-dihydroxyethylene) bisacrylamide, derivatives, or combinations thereof.

11. An orthopedic implant comprising the IPN or semi-IPN of claim 1.

12. The orthopedic implant of claim 11, wherein the orthopedic implant is adapted to fit an acromioclavicular joint, an ankle joint, a condyle, an elbow joint, a hand joint including a metacarpal joint, a finger joint, a thumb joint, a base of thumb joint, a glenoid, a hip joint including an acetabular joint, an intervertebral disc, a vertebral joint, including an intervertebral facet joint, a labrum, a meniscus, a foot joint, including a metatarsal joint and a toe joint, a patella, a tibial plateau, a jaw joint including a temporomandibular joint, a knee joint including a knee medial compartment joint, a patellofemoral joint, and a total knee joint, a knee meniscus, a shoulder joint including a labral joint, or a wrist joint and any portion thereof.

13. The orthopedic implant of claim 11, wherein the orthopedic implant is selected from cartilage replacement devices, joint replacement devices, meniscal replacements, interpositional spaces, tendon or ligament replacement or augmentation devices, cartilage scaffolds, cartilage replacement plugs, cartilage stimulation plugs, bone filler implants to stimulate cartilage regeneration, and facet or vertebral disc implants.

14. The orthopedic implant of claim 11, wherein the IPN or semi-IPN member comprises a bearing surface and an attachment zone.

15. The orthopedic implant of claim 14, wherein the bearing surface has a coefficient of friction of less than about 0.1.

16. The orthopedic implant of claim 15, comprising a bone interface member attached to the attachment zone.

17. The orthopedic implant of claim 16, wherein the bone interface member comprises a metal.

* * * * *